United States Patent [19]

Maynard et al.

[11] Patent Number: 5,998,439
[45] Date of Patent: Dec. 7, 1999

[54] SUBSTITUTED N-METHYL-N-(4-(PIPERIDIN-1-YL)-2-(ARYL)BUTYL)BENZAMIDES USEFUL FOR THE TREATMENT OF ALLERGIC DISEASES

[75] Inventors: George P. Maynard, Westbrook, Conn.; John M. Kane, Cincinnati, Ohio; Larry D. Bratton, Whitmore Lake, Mich.; Elizabeth M. Kudlacz, Groton, Conn.

[73] Assignee: Hoescht Marion Roussel, Inc., Bridgewater, N.J.

[21] Appl. No.: 09/079,692

[22] Filed: May 15, 1998

Related U.S. Application Data

[63] Continuation-in-part of application No. 08/771,544, Dec. 23, 1996, abandoned
[60] Provisional application No. 60/037,569, Feb. 21, 1996.

[51] Int. Cl.⁶ ........................ C07D 401/06; A61K 31/445
[52] U.S. Cl. ........................ 514/318; 514/321; 514/322; 514/327; 546/194; 546/199; 546/198; 546/221
[58] Field of Search ..................... 514/318, 321, 514/322, 327; 546/194, 199, 198, 221

[56] References Cited

U.S. PATENT DOCUMENTS

| | | | |
|---|---|---|---|
| 3,282,947 | 11/1966 | Grogan | 514/15 |
| 3,862,173 | 1/1975 | Carr | 514/255 |
| 4,254,129 | 3/1981 | Carr | 546/239 |
| 4,254,130 | 3/1981 | Carr | 546/237 |
| 4,285,958 | 8/1981 | Carr | 546/237 |
| 4,550,116 | 10/1985 | Soto | 514/326 |
| 4,598,079 | 7/1986 | Beyerle | 514/252 |
| 4,666,905 | 5/1987 | Downs | 514/222 |
| 4,835,161 | 5/1989 | Janssens | 514/255 |
| 4,908,372 | 3/1990 | Carr | 514/322 |
| 4,960,776 | 10/1990 | Walsh | 514/252 |

(List continued on next page.)

FOREIGN PATENT DOCUMENTS

| | | |
|---|---|---|
| 1591692 | 5/1991 | Australia . |
| 1490095 | 9/1995 | Australia . |
| 0145037 | 6/1985 | European Pat. Off. . |
| 0184257 | 6/1986 | European Pat. Off. . |
| 0282133 | 9/1988 | European Pat. Off. . |
| 0378254 | 7/1990 | European Pat. Off. . |
| 0428434 | 11/1990 | European Pat. Off. . |
| 0512902 | 5/1991 | European Pat. Off. . |
| 0482539 | 10/1991 | European Pat. Off. . |
| 0464927 | 1/1992 | European Pat. Off. . |
| 0533344 | 8/1992 | European Pat. Off. . |
| 0559538 | 3/1993 | European Pat. Off. . |
| 0625509 | 5/1994 | European Pat. Off. . |
| 0630887 | 5/1994 | European Pat. Off. . |
| 0517589 | 6/1991 | France . |
| 2601262 | 7/1976 | Germany . |
| 4297492 | 2/1991 | Jordan . |
| 9206086 | 10/1990 | WIPO . |
| 9222569 | 6/1991 | WIPO . |
| 9314113 | 1/1992 | WIPO . |
| 9201687 | 2/1992 | WIPO . |
| 9201697 | 2/1992 | WIPO . |
| 9300330 | 1/1993 | WIPO . |
| 9407495 | 4/1994 | WIPO . |
| 9426735 | 11/1994 | WIPO . |
| 9505377 | 2/1995 | WIPO . |
| 9508549 | 3/1995 | WIPO . |
| 9606094 | 2/1996 | WIPO . |
| 9610568 | 4/1996 | WIPO . |

OTHER PUBLICATIONS

Barnes, et al., TIPS 11:185–189 (May 1990).
Ichinose, et al., The Lancet 340:1248–1251 (Nov. 21, 1992).
Hagiwara, et al., "Studies on Neurokinin Antagonists 2.", Journal of Medicinal Chemistry, vol. 35, No. 17, 3184–3191, 1992.
Hagiwara, et al., Studies on Neurokinin Antagonists 1., J. Med. Chem, 35, 2015–2025, 1992.
Janssens, et al., J. Med. Chem. 28:1934–1943, (1985).
Janssens, et al., Drug Development Research 8:27–36, (1986).
Jannssens, et al., J. Med. Chem., 28 (12): 1925–1933, (1985).
Iemura, et al., Chem. Pharm. Bull., 37(4):967–972, (1989).
Janssens, et al., J. Med. Chem., 28(12):1943–1947, (1985).
Carr et al., The J. Organic Chem., 55(4): 1399–1401, (1990).
Iemura, et al., Chem. Pharm. Buul., 37(4):962–966, (1989).
Maynard, Biorganic and Medicinal Chemistry Letters, vol. 3 (4), 753–756, 1993).
Wahlgren, J. Heterocyclic Chem., 26, 541–543, 1989.
Iemura, Chem. Pharm. Bull., 37(4), 967–972, 1989.
Iemura, J. Heterocyclic Che., 24, 31–37, 1987.
Iemura, et al., J. Med. Chem., 29(7):1178–1183, (1986).
Hagiwara, et al., Studies on Neurokinin Antagonists 3., J. Med. Chem, 36, 2266–2278, 1993.
Emonds–Alt, et al., Life Sciences, 56(1):27–32, (1995).
Melloni, et al., Eur. J. Med. Chem., 26, 207–213 (1991).
Armour, et al, Biorganic & Med. Chem Ltrs, 6(9), 1015, 1020 (1996).
Ward, et al, J. Med. Chem., 38, 4985–4992 (1995).

*Primary Examiner*—Jane Fan
*Attorney, Agent, or Firm*—Erik K. Voelk; Barabara E. Kurys

[57] ABSTRACT

The present invention relates to novel substituted N-methyl-N-(4-(piperidin-1-yl)-2-(aryl)butyl)benzamide derivatives of the formula

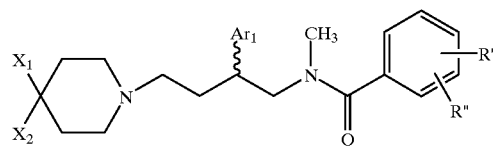

stereoisomers thereof, and pharmaceutically acceptable salts thereof which are useful as histamine receptor antagonists and tachykinin receptor antagonists. Such antagonists are useful in the treatment of allergic rhinitis, including seasonal rhinitis and sinusitis; inflammatory bowel diseases, including Crohn's disease and ulcerative colitis; asthma; bronchitis; and emesis.

21 Claims, No Drawings

U.S. PATENT DOCUMENTS

| | | | |
|---|---|---|---|
| 4,988,689 | 1/1991 | Janssens | 514/212 |
| 5,023,256 | 6/1991 | Roberto | 514/253 |
| 5,064,850 | 11/1991 | Carr | 514/322 |
| 5,166,136 | 11/1992 | Ward | 514/15 |
| 5,182,399 | 1/1993 | Kane | 546/199 |
| 5,212,187 | 5/1993 | Alisch | 514/336 |
| 5,214,040 | 5/1993 | Cuberes-Altisent | 514/218 |
| 5,236,921 | 8/1993 | Emonds-Alt | 514/252 |
| 5,272,150 | 12/1993 | Janssens | 514/258 |
| 5,317,020 | 5/1994 | Emonds-Alt | 514/255 |
| 5,322,850 | 6/1994 | Orjales-Venero | 514/322 |
| 5,350,852 | 9/1994 | Sanofi | 544/336 |
| 5,371,093 | 12/1994 | Carr | 514/321 |
| 5,411,971 | 5/1995 | Sanofi | 514/318 |
| 5,434,158 | 7/1995 | Shah | 514/278 |
| 5,534,525 | 7/1996 | Miller | 514/316 |

SUBSTITUTED N-METHYL-N-(4-(PIPERIDIN-1-YL)-2-(ARYL)BUTYL)BENZAMIDES USEFUL FOR THE TREATMENT OF ALLERGIC DISEASES

This application is a continuation-in-part of application Ser. No. 08/771,544, filed Dec. 23, 1996, now abandoned which is hereby incorporated by reference, which claims the benefit of provisional application 60/037,569, filed Feb. 21, 1996.

The present invention relates to novel substituted N-methyl-N-(4-(piperidin-1-yl)-2-(aryl)butyl)benzamide derivatives (herein referred to as a compound or compounds of formula (1)) and their use as histamine receptor antagonists and tachykinin receptor antagonists. Such antagonists are useful in the treatment of asthma; bronchitis; inflammatory bowel diseases, including Crohn's disease and ulcerative colitis; allergic rhinitis, including seasonal rhinitis and sinusitis; allergies; and emesis.

The compounds of the present invention are useful in their pharmacological activities, such as histamine receptor antagonism and tachykinin receptor antagonism. Antagonism of histamine responses can be elicited through blocking of histamine receptors. Antagonism of tachykinin responses can be elicited through blocking of tachykinin receptors. One object of the present invention is to provide new and useful antagonists of histamine. A further object of the present invention is to provide new and useful antagonists of tachykinins. A particular object of the present invention are those compounds that exhibit both $H_1$ and $NK_1$ receptor antagonism.

SUMMARY OF THE INVENTION

The present invention provides novel substituted N-methyl-N-(4-(piperidin-1-yl)-2-(aryl)butyl)benzamide derivatives of the formula:

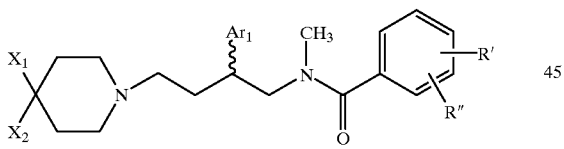

formula (1)

wherein

R' is from 1 to 3 substituents each independently chosen from the group consisting of hydrogen, halogen, $C_1$–$C_6$ alkyl, and $C_1$–$C_6$ alkoxy;

R" is hydrogen or a radical chosen from the group consisting of

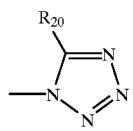 and 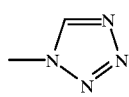

wherein
$R_{20}$ is selected from the group consisting of hydrogen, $C_1$–$C_4$ alkyl, and —$CF_3$;

$Ar_1$ is a radical chosen from the group consisting of

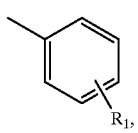 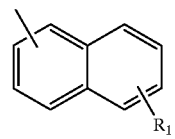

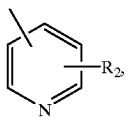 and 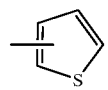

wherein $R_1$ is from 1 to 3 substituents each independently chosen from the group consisting of hydrogen, halogen, hydroxy, —$CF_3$, $C_1$–$C_6$ alkyl, and $C_1$–$C_6$ alkoxy;

$R_2$ is from 1 to 2 substituents each independently chosen from the group consisting of hydrogen, halogen, $C_1$–$C_6$ alkyl, and $C_1$–$C_6$ alkoxy;

$X_1$ and $X_2$ are as defined in one of parts A), B), or C):
A) $X_1$ is hydrogen;
$X_2$ is a radical chosen from the group consisting of

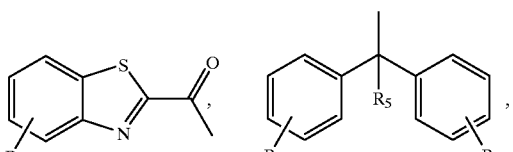

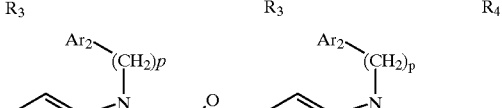

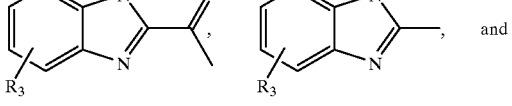 and

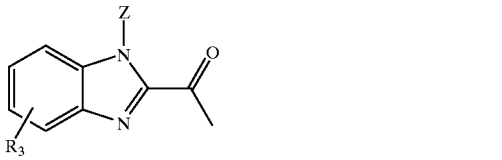

wherein
p is 1 or 2;
$R_3$ is from 1 to 3 substituents each independently chosen from the group consisting of hydrogen, halogen, —$CF_3$, $C_1$–$C_6$ alkyl, and $C_1$–$C_6$ alkoxy;
$R_4$ is from 1 to 3 substituents each independently chosen from the group consisting of hydrogen, halogen, —$CF_3$, $C_1$–$C_6$ alkyl, and $C_1$–$C_6$ alkoxy;
$R_5$ is hydrogen or hydroxy;
$Ar_2$ is a radical chosen from the group consisting of

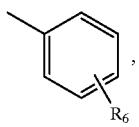 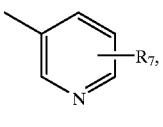 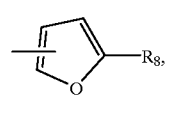

-continued

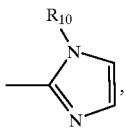 and 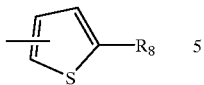

wherein
R$_6$ is from 1 to 3 substituents each independently chosen from the group consisting of hydrogen, halogen, —CF$_3$, C$_1$–C$_6$ alkyl, C$_1$–C$_6$ alkoxy, and —CO$_2$R$_9$ wherein R$_9$ is chosen from the group consisting of hydrogen and C$_1$–C$_4$ alkyl;

R$_7$ is from 1 to 2 substituents each independently chosen from the group consisting of hydrogen, halogen, C$_1$–C$_6$ alkyl, and C$_1$–C$_6$ alkoxy;

R$_8$ is chosen from the group consisting of hydrogen, —CH$_3$, and —CH$_2$OH;

R$_{10}$ is chosen from the group consisting of hydrogen, C$_1$–C$_4$ alkyl, and benzyl;

Z is chosen from the group consisting of hydrogen, C$_1$–C$_6$ alkyl, —(CH$_2$)$_w$—O—(CH$_2$)$_t$—Y, —(CH$_2$)$_f$A, —(CH$_2$)$_u$CO$_2$R$_{11}$, —(CH$_2$)$_u$C(O)NR$_{12}$R$_{13}$, —(CH$_2$)$_g$C(O)(CH$_2$)$_h$CH$_3$, —(CH$_2$)$_w$—O—Ar$_3$, —CH$_2$CH$_2$OCF$_3$, —CH$_2$CF$_3$, —CH$_2$CH$_2$CH$_2$CF$_3$, —(CH$_2$)$_2$CH=CH$_2$, —CH$_2$CH=CH$_2$, —CH$_2$CH=CHCH$_3$, —CH$_2$CH=CHCH$_2$CH$_3$, —CH$_2$CH=C(CH$_3$)$_2$, and —CH$_2$OCH$_2$CH$_2$Si(CH$_3$)$_3$ wherein
w is an integer from 2 to 5;
t is an integer from 1 to 3;
f is 2 or 3;
u is an integer from 1 to 4;
g is an integer from 1 to 3;
h is an integer from 0 to 3;
w is an integer from 2 to 4;
y is chosen from the group consisting of hydrogen, —CF$_3$, —CH=CH$_2$, —CH=C(CH$_3$)$_2$, and —CO$_2$R$_{14}$ wherein R$_{14}$ is chosen from the group consisting of hydrogen and C$_1$–C$_4$ alkyl;

A is chosen from the group consisting of —NR$_{15}$R$_{16}$, acetylamino, and morpholino wherein R$_{15}$ is chosen from the group consisting of hydrogen and C$_1$–C$_4$ alkyl and R$_{16}$ is C$_1$–C$_4$ alkyl;

R$_{11}$ is chosen from the group consisting of hydrogen and C$_1$–C$_4$ alkyl;

R$_{12}$ is chosen from the group consisting of hydrogen, C$_1$–C$_4$ alkyl, and benzyl;

R$_{13}$ is chosen from the group consisting of hydrogen and C$_1$–C$_4$ alkyl;

Ar$_3$ is a radical chosen from the group consisting of

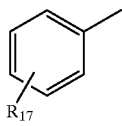 and 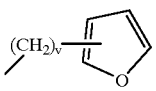

wherein
v is an integer from 1 to 3;
R$_{17}$ is chosen from the group consisting of hydrogen and —CO$_2$R$_{18}$ wherein R$_{18}$ is chosen from the group consisting of hydrogen and C$_1$–C$_4$ alkyl;

B) X$_1$ is hydroxy;

X$_2$ is a radical chosen from the group consisting of

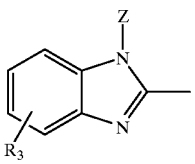 and 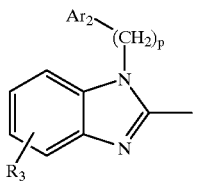

wherein p, R$_3$, Z, and Ar$_2$ are as previously defined;

C) X$_2$ is a radical of the formula;

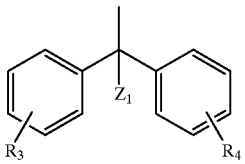

wherein R$_3$ and R$_4$ are as previously defined; and
X$_1$ and Z$_1$ taken together form a second bond between the carbon atoms bearing X$_1$ and Z$_1$;

and stereoisomers and pharmaceutically acceptable salt thereof.

As is appreciated by one of ordinary skill in the art the compounds of the formula (1) may exist as stereoisomersN-methyl-N-(4-(piperidin-1-yl)-2-(aryl)butyl)benzamide. Specifiacally, it is recognized that the the present N-methyl-N-(4-(piperidin-1-yl)-2-(aryl)butyl)benzamides exist as stereoisomers at the 2-position of the butyl, that is, at the point of attachment of the aryl substituent. Any reference in this application to one of the compounds of the formula (1) is meant to encompass either specific stereoisomers or a mixture of stereoisomers.

The specific stereoisomers can be prepared by stereospecific synthesis using enantiomerically pure or enantiomerically enriched starting materials. The specific stereoisomers of either starting materials or products can be resolved and recovered by techniques known in the art, such as chromatography on chiral stationary phases, enzymatic resolution, or fractional recrystallization of addition salts formed by reagents used for that purpose. Useful methods of resolving and recovering specific stereoisomers are known in the art and described in *Stereochemistry of Organic Compounds*, E. L. Eliel and S. H. Wilen, Wiley (1994) and *Enantiomers, Racemates, and Resolutions*, J. Jacques, A. Collet, and S. H. Wilen, Wiley (1981).

As used in this application:
a) the term "halogen" refers to a fluorine atom, chlorine atom, bromine atom, or iodine atom;
b) the term "C$_1$–C$_6$ alkyl" refers to a branched or straight chained alkyl radical containing from 1 to 6 carbon atoms, such as methyl, ethyl, n-propyl, isopropyl, n-butyl, isobutyl, t-butyl, pentyl, hexyl, cyclopentyl, cyclohexyl, etc;
c) the term "C$_1$–C$_6$ alkoxy" refers to a straight or branched alkoxy group containing from 1 to 6 carbon atoms, such as methoxy, ethoxy, n-propoxy, isopropoxy, n-butoxy, isobutoxy, t-butoxy, pentoxy, hexoxy, cyclopentoxy, cyclohexoxy, etc;
d) the designations —C(O)— or —(O)C— refer to a carbonyl group of the formula:

e) the designation "⌇" refers to a bond for which the stereochemistry is not designated;

f) as used in the examples and preparations, the following terms have the meanings indicated: "kg" refers to kilograms, "g" refers to grams, "mg" refers to milligrams, "µg" refers to micrograms, "mol" refers to moles, "mmol" refers to millimoles, "nmole" refers to nanomoles, "L" refers to liters, "mL" or "ml" refers to milliliters, "µL" refers to microliters, "° C." refers to degrees Celsius, "$R_f$" refers to retention factor, "mp" refers to melting point, "dec" refers to decomposition, "bp" refers to boiling point, "mm of Hg" refers to pressure in millimeters of mercury, "cm" refers to centimeters, "nm" refers to nanometers, "$[\alpha]^{20}_D$" refers to specific rotation of the D line of sodium at 20° C. obtained in a 1 decimeter cell, "c" refers to concentration in g/mL, "THF" refers to tetrahydrofuran, "DMF" refers to dimethylformamide, "brine" refers to a saturated aqueous sodium chloride solution, "M" refers to molar, "mM" refers to millimolar, "µM" refers to micromolar, "nM" refers to nanomolar, "psi" refers to pounds per square inch, "TLC" refers to thin layer chromatography, "HPLC" refers to high performance liquid chromatography, "HRMS" refers to high resolution mass spectrum, "µCi" refers to microcuries, "i.p." refers to intraperitoneally, "i.v." refers to intravenously, and "DPM" refers to disintegrations per minute;

g) the designation

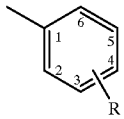

refers to a phenyl or a substituted phenyl and it is understood that the radical is attached at the 1-position and the substituent or substituents represented by R can be attached in any of the 2, 3, 4, 5, or 6 positions;

h) the designation

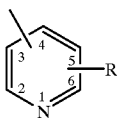

refers to a pyridine, substituted pyridine, pyridyl or substituted pyridyl and it is understood that the radical can be attached at either the 2-position, the 3-position, or the 4-position, it is further understood that when the radical is attached at the 2-position the substituent or substituents represented by R can be attached in any of the 3, 4, 5, or 6 positions, that when the radical is attached at the 3-position the substituent or substituents represented by R can be attached in any of the 2, 4, 5, or 6 positions, and that when the radical is attached at the 4-position the substituent or substituents represented by R can be attached in any of the 2, 3, 5, or 6 positions;

i) the designation

refers to a thienyl or thiophene and it is understood that the radical is attached at the 2 or 3-positions;

j) the designation

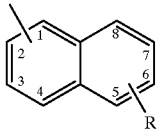

refers to a naphthyl or substituted naphthyl and it is understood that the radical can be attached at either the 1-position or the 2-position, it is further understood that when the radical is attached at the 1-position the substituent or substituents represented by R can be attached in any of the 2, 3, 4, 5, 6, 7, or 8 positions and that when the radical is attached at the 2-position the substituent or substituents represented by R can be attached in any of the 1, 3, 4, 5, 6, 7, or 8 positions;

k) the term "enantiomeric excess" or "ee" refers to the percent by which one enantiomer, E1, is in excess in a mixture of the two enantiomers, E1 plus E2, such that $$\{(E1-E2) \div (E1+E2)\} \times 100\% = ee,$$

with the designation "(+)-" refers to the plus enantiomer, "(−)-" refers to the minus enantiomer;

l) the term "$C_1$–$C_4$ alkyl" refers to a saturated straight or branched chain alkyl group containing from 1–4 carbon atoms and includes methyl, ethyl, propyl, isopropyl, n-butyl, isobutyl, and t-butyl;

m) the designations —$CO_2R$ and —C(O)OR refer to a group of the formula:

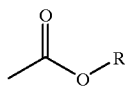

n) the designation —C(O)NRR refers to a group of the formula:

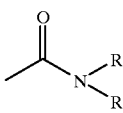

o) the designation

refers to a furyl or furan and it is understood that the radical is attached at either the 2- or 3-position;

p) the term "pharmaceutically acceptable salts thereof refers to either an acid addition salt or a basic addition salt.

The expression "pharmaceutically acceptable acid addition salts" is intended to apply to any non-toxic organic or inorganic acid addition salt of the base compounds represented by formula (1) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

Preferred embodiments of formula (1) are given below: 1) Compounds wherein $X_1$ is hydrogen are preferred;

2) Compounds wherein $X_2$ is a radical of the formula

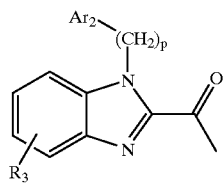

are preferred;

3) Compounds wherein $X_2$ is a radical of the formula

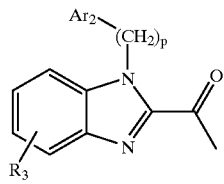

wherein p is 1 and $Ar_2$ is 4-fluorophenyl, pyrid-2-yl, fur-2-yl, or fur-3-yl are more preferred;

4) Compounds wherein $X_2$ is a radical of the formula

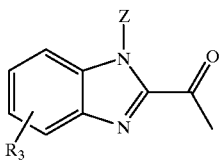

are preferred; and

5) Compounds wherein $X_2$ is a radical of the formula

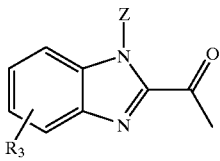

wherein Z is —$(CH_2)_w$—O—$(CH_2)_t$—Y wherein w is 2 are more preferred, with compounds wherein Z is 2-ethoxyethyl being most preferred.

Examples of compounds encompassed by the present invention include the following. It is understood that the examples encompass both the (+)-isomer and the (−)-isomer of the compound and mixtures thereof. This list is meant to be representative only and is not intended to limit the scope of the invention in any way:

N-Methyl-N-(4-(4-(1H-benzimidazole-2-carbonyl) piperidin-1-yl)-2-phenylbutyl)benzamide;

N-Methyl-N-(4-(4-(1H-benzimidazole-2-carbonyl) piperidin-1-yl)-2-phenylbutyl)-3,4,5-trimethoxybenzamide;

N-Methyl-N-(4-(4-(1H-benzimidazole-2-carbonyl) piperidin-1-yl)-2-(4-fluorophenyl)butyl)benzamide;

N-Methyl-N-(4-(4-(1H-benzimidazole-2-carbonyl) piperidin-1-yl)-2-(4-fluorophenyl)butyl)-3,4,5-trimethoxybenzamide;

N-Methyl-N-(4-(4-(1H-benzimidazole-2-carbonyl) piperidin-1-yl)-2-(3,4-difluorophenyl)butyl)benzamide;

N-Methyl-N-(4-(4-(1H-benzimidazole-2-carbonyl) piperidin-1-yl)-2-(3,4-difluorophenyl)butyl)-3,4,5-trimethoxybenzamide;

N-Methyl-N-(4-(4-(1H-benzimidazole-2-carbonyl) piperidin-1-yl)-2-(3-chlorophenyl)butyl)benzamide;

N-Methyl-N-(4-(4-(1H-benzimidazole-2-carbonyl) piperidin-1-yl)-2-(3-chlorophenyl)butyl)-3,4,5-trimethoxybenzamide;

N-Methyl-N-(4-(4-(1H-benzimidazole-2-carbonyl) piperidin-1-yl)-2-(4-chlorophenyl)butyl)benzamide;

N-Methyl-N-(4-(4-(1H-benzimidazole-2-carbonyl) piperidin-1-yl)-2-(4-chlorophenyl)butyl)-3,4,5-trimethoxybenzamide;

N-Methyl-N-(4-(4-(1H-benzimidazole-2-carbonyl) piperidin-1-yl)-2-(3,4-dichlorophenyl)butyl)benzamide;

N-Methyl-N-(4-(4-(1H-benzimidazole-2-carbonyl) piperidin-1-yl)-2-(3,4-dichlorophenyl)butyl)-3,4,5-trimethoxybenzamide;

N-Methyl-N-(4-(4-(1H-benzimidazole-2-carbonyl) piperidin-1-yl)-2-(4-methoxyphenyl)butyl)benzamide;

N-Methyl-N-(4-(4-(1H-benzimidazole-2-carbonyl) piperidin-1-yl)-2-(4-methoxyphenyl)butyl)-3,4,5-trimethoxybenzamide;

N-Methyl-N-(4-(4-(1H-benzimidazole-2-carbonyl) piperidin-1-yl)-2-(3-methoxyphenyl)butyl)benzamide;

N-Methyl-N-(4-(4-(1H-benzimidazole-2-carbonyl) piperidin-1-yl)-2-(3-methoxyphenyl)butyl)-3,4,5-trimethoxybenzamide;

N-Methyl-N-(4-(4-(1H-benzimidazole-2-carbonyl) piperidin-1-yl)-2-(3,4-dimethoxyphenyl)butyl) benzamide;

N-Methyl-N-(4-(4-(1H-benzimidazole-2-carbonyl) piperidin-1-yl)-2-(3,4-dimethoxyphenyl)butyl)-3,4,5-trimethoxybenzamide;

N-Methyl-N-(4-(4-(1-(4-fluorobenzyl)-1H-benzoimidazol-2-yl)-4-hydroxypiperidin-1-yl)-2-phenylbutyl) benzamide;

N-Methyl-N-(4-(4-(1-(4-fluorobenzyl)-1H-benzoimidazol-2-yl)-4-hydroxypiperidin-1-yl)-2-phenylbutyl)-3,4,5-trimethoxybenzamide;

N-Methyl-N-(4-(4-(1-(4-fluorobenzyl)-1H-benzoimidazol-2-yl)-4-hydroxypiperidin-1-yl)-2-(4-fluorophenyl)butyl) benzamide;

N-Methyl-N-(4-(4-(1-(4-fluorobenzyl)-1H-benzoimidazol-2-yl)-4-hydroxypiperidin-1-yl)-2-(3,4-dichlorophenyl) butyl)benzamide;

N-Methyl-N-(4-(4-(1-(2-(fur-2-ylmethoxy)ethyl)-1H-benzimidazole-2-carbonyl)piperidin-1-yl)-2-phenylbutyl) benzamide;

N-Methyl-N-(4-(4-(1-(2-(fur-2-ylmethoxy)ethyl)-1H-benzimidazole-2-carbonyl)piperidin-1-yl)-2-phenylbutyl)-3,4,5-trimethoxybenzamide;

N-Methyl-N-(4-(4-(1-(2-(fur-2-ylmethoxy)ethyl)-1H-benzimidazole-2-carbonyl)piperidin-1-yl)-2-(4-fluorophenyl)butyl)benzamide;

N-Methyl-N-(4-(4-(1-(2-(fur-2-ylmethoxy)ethyl)-1H-benzimidazole-2-carbonyl)piperidin-1-yl)-2-(4-fluorophenyl)butyl)-3,4,5-trimethoxybenzamide;

N-Methyl-N-(4-(4-(1-(2-(fur-2-ylmethoxy)ethyl)-1H-benzimidazole-2-carbonyl)piperidin-1-yl)-2-(3,4-difluorophenyl)butyl)benzamide;

N-Methyl-N-(4-(4-(1-(2-(fur-2-ylmethoxy)ethyl)-1H-benzimidazole-2-carbonyl)piperidin-1-yl)-2-(3,4-difluorophenyl)butyl)-3,4,5-trimethoxybenzamide;

N-Methyl-N-(4-(4-(1-(2-(fur-2-ylmethoxy)ethyl)-1H-benzimidazole-2-carbonyl)piperidin-1-yl)-2-(3-chlorophenyl)butyl)benzamide;

N-Methyl-N-(4-(4-(1-(2-(fur-2-ylmethoxy)ethyl)-1H-benzimidazole-2-carbonyl)piperidin-1-yl)-2-(3-chlorophenyl)butyl)-3,4,5-trimethoxybenzamide;

N-Methyl-N-(4-(4-(1-(2-(fur-2-ylmethoxy)ethyl)-1H-benzimidazole-2-carbonyl)piperidin-1-yl)-2-(4-chlorophenyl)butyl)benzamide;

N-Methyl-N-(4-(4-(1-(2-(fur-2-ylmethoxy)ethyl)-1H-benzimidazole-2-carbonyl)piperidin-1-yl)-2-(4-chlorophenyl)butyl)-3,4,5-trimethoxybenzamide;

N-Methyl-N-(4-(4-(1-(2-(fur-2-ylmethoxy)ethyl)-1H-benzimidazole-2-carbonyl)piperidin-1-yl)-2-(3,4-dichlorophenyl)butyl)benzamide;

N-Methyl-N-(4-(4-(1-(2-(fur-2-ylmethoxy)ethyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(2-(fur-2-ylmethoxy)ethyl)-1H-benzimidazole-2-carbonyl)piperidin-1-yl)-2-(4-methoxyphenyl)butyl)benzamide;

N-Methyl-N-(4-(4-(1-(2-(fur-2-ylmethoxy)ethyl)-1H-benzimidazole-2-carbonyl)piperidin-1-yl)-2-(4-methoxyphenyl)butyl)-3,4,5-trimethoxybenzamide;

N-Methyl-N-(4-(4-(1-(2-(fur-2-ylmethoxy)ethyl)-1H-benzimidazole-2-carbonyl)piperidin-1-yl)-2-(3-methoxyphenyl)butyl)benzamide;

N-Methyl-N-(4-(4-(1-(2-(fur-2-ylmethoxy)ethyl)-1H-benzimidazole-2-carbonyl)piperidin-1-yl)-2-(3-methoxyphenyl)butyl)-3,4,5-trimethoxybenzamide;

N-Methyl-N-(4-(4-(1-(2-(fur-2-ylmethoxy)ethyl)-1H-benzimidazole-2-carbonyl)piperidin-1-yl)-2-(3,4-dimethoxyphenyl)butyl)benzamide;

N-Methyl-N-(4-(4-(1-(2-(fur-2-ylmethoxy)ethyl)-1H-benzimidazole-2-carbonyl)piperidin-1-yl)-2-(3,4-dimethoxyphenyl)butyl)-3,4,5-trimethoxybenzamide;

N-Methyl-N-(4-(4-(1-(3-(4-fluorophenoxy)propyl)-1H-benzimidazole-2-carbonyl)piperidin-1-yl)-2-phenylbutyl)-3,4,5-trimethoxybenzamide;

N-Methyl-N-(4-(4-(1-(3-(4-fluorophenoxy)propyl)-1H-benzimidazole-2-carbonyl)piperidin-1-yl)-2-(3-chlorophenyl)butyl)-3,4,5-trimethoxybenzamide;

N-Methyl-N-(4-(4-(1-(3-(4-fluorophenoxy)propyl)-1H-benzimidazole-2-carbonyl)piperidin-1-yl)-2-(3,4-dichlorophenyl)butyl)benzamide;

N-Methyl-N-(4-(4-(1-(2-ethoxyethyl)-1H-benzimidazole-2-carbonyl)piperidin-1-yl)-2-phenylbutyl)benzamide;

N-Methyl-N-(4-(4-(1-(2-ethoxyethyl)-1H-benzimidazole-2-carbonyl)piperidin-1-yl)-2-phenylbutyl)-3,4,5-trimethoxybenzamide;

N-Methyl-N-(4-(4-(1-(2-ethoxyethyl)-1H-benzimidazole-2-carbonyl)piperidin-1-yl)-2-(4-fluorophenyl)butyl)benzamide;

N-Methyl-N-(4-(4-(1-(2-ethoxyethyl)-1H-benzimidazole-2-carbonyl)piperidin-1-yl)-2-(4-fluorophenyl)butyl)-3,4,5-trimethoxybenzamide;

N-Methyl-N-(4-(4-(1-(2-ethoxyethyl)-1H-benzimidazole-2-carbonyl)piperidin-1-yl)-2-(3,4-difluorophenyl)butyl)benzamide;

N-Methyl-N-(4-(4-(1-(2-ethoxyethyl)-1H-benzimidazole-2-carbonyl)piperidin-1-yl)-2-(3,4-difluorophenyl)butyl)-3,4,5-trimethoxybenzamide;

N-Methyl-N-(4-(4-(1-(2-ethoxyethyl)-1H-benzimidazole-2-carbonyl)piperidin-1-yl)-2-(3-chlorophenyl)butyl)benzamide;

N-Methyl-N-(4-(4-(1-(2-ethoxyethyl)-1H-benzimidazole-2-carbonyl)piperidin-1-yl)-2-(3-chlorophenyl)butyl)-3,4,5-trimethoxybenzamide;

N-Methyl-N-(4-(4-(1-(2-ethoxyethyl)-1H-benzimidazole-2-carbonyl)piperidin-1-yl)-2-(4-chlorophenyl)butyl)benzamide;

N-Methyl-N-(4-(4-(1-(2-ethoxyethyl)-1H-benzimidazole-2-carbonyl)piperidin-1-yl)-2-(4-chlorophenyl)butyl)-3,4,5-trimethoxybenzamide;

N-Methyl-N-(4-(4-(1-(2-ethoxyethyl)-1H-benzimidazole-2-carbonyl)piperidin-1-yl)-2-(3,4-dichlorophenyl)butyl)benzamide;

N-Methyl-N-(4-(4-(1-(2-ethoxyethyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(2-ethoxyethyl)-1H-benzimidazole-2-carbonyl)piperidin-1-yl)-2-(4-methoxyphenyl)butyl)benzamide;

N-Methyl-N-(4-(4-(1-(2-ethoxyethyl)-1H-benzimidazole-2-carbonyl)piperidin-1-yl)-2-(4-methoxyphenyl)butyl)-3,4,5-trimethoxybenzamide;

N-Methyl-N-(4-(4-(1-(2-ethoxyethyl)-1H-benzimidazole-2-carbonyl)piperidin-1-yl)-2-(3-methoxyphenyl)butyl)benzamide;

N-Methyl-N-(4-(4-(1-(2-ethoxyethyl)-1H-benzimidazole-2-carbonyl)piperidin-1-yl)-2-(3-methoxyphenyl)butyl)-3,4,5-trimethoxybenzamide;

N-Methyl-N-(4-(4-(1-(2-ethoxyethyl)-1H-benzimidazole-2-carbonyl)piperidin-1-yl)-2-(3,4-dimethoxyphenyl)butyl)benzamide;

N-Methyl-N-(4-(4-(1-(2-ethoxyethyl)-1H-benzimidazole-2-carbonyl)piperidin-1-yl)-2-(3,4-dimethoxyphenyl)butyl)-3,4,5-trimethoxybenzamide;

N-Methyl-N-(4-(4-(1-(2-ethoxyethyl)-1H-benzimidazole-2-carbonyl)piperidin-1-yl)-2-phenylbutyl)-2-methoxy-5-(1H-tetrazol-1-yl)benzamide;

N-Methyl-N-(4-(4-(1-(2-ethoxyethyl)-1H-bennzimidazole-2-carbonyl)piperidin-1-yl)-2-(3,4-difluorophenyl)butyl)-2-methoxy-5-(1H-tetrazol-1-yl) benzamide;

N-Methyl-N-(4-(4-(1-(2-ethoxyethyl)-1H-benzimidazole-2-carbonyl)piperidin-1-yl)-2-(3,4-dichlorophenyl)butyl)-2-methoxy-5-(1H-tetrazol-1-yl) benzamide;

N-Methyl-N-(4-(4-(1-(2-ethoxyethyl)-1H-benzimidazole-2-carbonyl)piperidin-1-yl)-2-(3-methoxyphenyi)butyl)-2-methoxy-5-(1H-tetrazol-1-yl)benzamide;

N-Methyl-N-(4-(4-(1-(2-ethoxyethyl)-1H-benzimidazole-2-carbonyl)piperidin-1-yl)-2-phenylbutyl)-2-methoxy-5-(4H-triazol-4-yl)benzamide;

N-Methyl-N-(4-(4-(1-(2-ethoxyethyl)-1H-berzimidazole-2-carbonyl)piperidin-1-yl)-2-(3,4-difluorophenyl)butyl)-2-methoxy-5-(4H-triazol-4-yl)benzamide;

N-Methyl-N-(4-(4-(1-(2-ethoxyethyl)-1H-benzlmidazole-2-carbon-yl)piperidin-1-yl)-2-(3,4-dichlorophenyl)butyl)-2-methoxy-5-(4H-triazol-4-yl)benzamide;

N-Methyl-N-(4-(4-(1-(2-ethoxyethyl)-1H-benzamidazole-2-carbonyl)piperidin-1-yl)-2-(3-methoxyphenyl)butyl)-2-methoxy-5-(4H-triazol-4-yl)benzamide;

N-Methyl-N-(4-(4-(1-(fur-2-ylmethyl)-1H-benzimidazole-2-carbonyl)piperdin-1-yl-2-phenylbutyl)benzamide;

N-Methyl-N-(4-(4-(1-(fur-2-ylmethyl)-1H-benzimidazole-2-carbonyl)piperidin-1-yl)-2-phenylbutyl)-3,4,5-trimethoxybenzamide;

N-Methy-N-(4-(4-(1-(fur-2-ylmethyl)-1H-benzimidazole-2-carbonyl)piperidin-1-yl)-2-(4-fluorophenyl)butyl)benzamide;

N-Methyl-N-(4-(4-(1-(fur-2-ylmethyl)-1H-benzimidazole-2-carbonyl)piperidin-1-yl)-2-(4-fluorophenyl)butyl)-3,4,5-trimethoxybenzamide;

N-Methyl-N-(4-(4-(1-(fur-2-ylmethyl)-1H-benzimidazole-2-carbonyl)piperidin-1-yl)-2-(3,4-difluorophenyl)butyl)benzamide;

N-Methyl-N-(4-(4-(1-(fur-2-ylmethyl)-1H-benzimidazole-2-carbonyl)piperidin-1-yl)-2-(3,4-difluorophenyl)butyl)-3,4,5-trimethoxybenzamide;

N-Methyl-N-(4-(4-(1-(fur-2-ylmethyl)-1H-benzimidazole-2-carbonyl)piperidin-1-yl)-2-(3-chlorophenyl)butyl)benzamide;

N-Methyl-N-(4-(4-(1-(fur-2-ylmethyl)-1H-benzimidazole-2-carbonyl)piperidin-1-yl)-2-(3-chlorophenyl)butyl)-3,4,5-trimethoxybenzamide;

N-Methyl-N-(4-(4-(1-(fur-2-ylmethyl)-1H-benzimidazole-2-carbonyl)piperidin-1-yl)-2-(4-chlorophenyl)butyl)benzamide;

N-Methyl-N-(4-(4-(1-(fur-2-ylmethyl)-1H-benzimidazole-2-carbonyl)piperidin-1-yl)-2-(4-chlorophenyl)butyl)-3,4,5-trimethoxybenzamide;

N-Methyl-N-(4-(4-(1-(fur-2-ylmethyl)-1H-benzimidazole-2-carbonyl)piperidin-1-yl)-2-(3,4-dichlorophenyl)butyl)benzamide;

N-Methyl-N-(4-(4-(1-(fur-2-ylmethyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(fur-2-ylmethyl)-1H-benzimidazole-2-carbonyl)piperidin-1-yl)-2-(4-methoxyphenyl)butyl)-3,4,5-trimethoxybenzamide;

N-Methyl-N-(4-(4-(1-(fur-2-ylmethyl)-1H-benzimidazole-2-carbonyl)piperidin-1-yl)-2-(3-methoxyphenyl)butyl)benzamide;

N-Methyl-N-(4-(4-(1-(fur-2-ylmethyl)-1H-benzimidazole-2-carbonyl)piperidin-1-yl)-2-(3-methoxyphenyl)butyl)-3,4,5-trimethoxybenzamide;

N-Methyl-N-(4-(4-(1-(fur-2-ylmethyl)-1H-benzimidazole-2-carbonyl)piperidin-1-yl)-2-(3,4-dimethoxyphenyl)butyl)benzamide;

N-Methyl-N-(4-(4-(1-(fur-2-ylmethyl)-1H-benzimidazole-2-carbonyl)piperidin-1-yl)-2-(3,4-dimethoxyphenyl)butyl)-3,4,5-trimethoxybenzamide;

N-Methyl-N-(4-(4-(1-(fur-3-ylmethyl)-1H-benzimidazole-2-carbonyl)piperidin-1-yl)-2-phenylbutyl)benzamide;

N-Methyl-N-(4-(4-(1-(fur-3-ylmethyl)-1H-benzimidazole-2-carbonyl)piperidin-1-yl)-2-phenylbutyl)-3,4,5-trimethoxybenzamide;

N-Methyl-N-(4-(4-(1-(fur-3-ylmethyl)-1H-benzimidazole-2-carbonyl)piperidin-1-yl)-2-(4-fluorophenyl)butyl)benzamide;

N-Methyl-N-(4-(4-(1-(fur-3-ylmethyl)-1H-benzimidazole-2-carbonyl)piperidin-1-yl)-2-(4-fluorophenyl)butyl)-3,4,5-trimethoxybenzamide;

N-Methyl-N-(4-(4-(1-(fur-3-ylmethyl)-1H-benzimidazole-2-carbonyl)piperidin-1-yl)-2-(3,4-difluorophenyl)butyl)benzamide;

N-Methyl-N-(4-(4-(1-(fur-3-ylmethyl)-1H-benzimidazole-2-carbonyl)piperidin-1-yl)-2-(3,4-difluorophenyl)butyl)-3,4,5-trimethoxybenzamide;

N-Methyl-N-(4-(4-(1-(fur-3-ylmethyl)-1H-benzimidazole-2-carbonyl)piperidin-1-yl)-2-(3-chlorophenyl)butyl)benzamide;

N-Methyl-N-(4-(4-(1-(fur-3-ylmethyl)-1H-benzimidazole-2-carbonyl)piperidin-1-yl)-2-(3-chlorophenyl)butyl)-3,4,5-trimethoxybenzamide;

N-Methyl-N-(4-(4-(1-(fur-3-ylmethyl)-1H-benzimidazole-2-carbonyl)piperidin-1-yl)-2-(4-chlorophenyl)butyl)benzamide;

N-Methyl-N-(4-(4-(1-(fur-3-ylmethyl)-1H-benzimidazole-2-carbonyl)piperidin-1-yl)-2-(4-chlorophenyl)butyl)-3,4,5-trimethoxybenzamide;

N-Methyl-N-(4-(4-(1-(fur-3-ylmethyl)-1H-benzimidazole-2-carbonyl)piperidin-1-yl)-2-(3,4-dichlorophenyl)butyl)benzamide;

N-Methyl-N-(4-(4-(1-(fur-3-ylmethyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(fur-3-ylmethyl)-1H-benzimidazole-2-carbonyl)piperidin-1-yl)-2-(4-methoxyphenyl)butyl)-3,4,5-trimethoxybenzamide;

N-Methyl-N-(4-(4-(1-(fur-3-ylmethyl)-1H-benzimidazole-2-carbonyl)piperidin-1-yl)-2-(3-methoxyphenyl)butyl)benzamide;

N-Methyl-N-(4-(4-(1-(fur-3-ylmethyl)-1H-benzimidazole-2-carbonyl)piperidin-1-yl)-2-(3-methoxyphenyl)butyl)-3,4,5-trimethoxybenzamide;

N-Methyl-N-(4-(4-(1-(fur-3-ylmethyl)-1H-benzimidazole-2-carbonyl)piperidin-1-yl)-2-(3,4-dimethoxyphenyl)butyl)benzamide;

N-Methyl-N-(4-(4-(1-(fur-3-ylmethyl)-1H-benzimidazole-2-carbonyl)piperidin-1-yl)-2-(3,4-dimethoxyphenyl)butyl)-3,4,5-trimethoxybenzamide;

N-Methyl-N-(4-(4-(1-(pyrid-2-ylmethyl)-1H-benzimidazole-2-carbonyl)piperidin-1-yl)-2-phenylbutyl)benzamide;

N-Methyl-N-(4-(4-(1-(pyrid-2-ylmethyl)-1H-benzimidazole-2-carbonyl)piperidin-1-yl)-2-phenylbutyl)-3,4,5-trimethoxybenzamide;

N-Methyl-N-(4-(4-(1-(pyrid-2-ylmethyl)-1H-benzimidazole-2-carbonyl)piperidin-1-yl)-2-(4-fluorophenyl)butyl)benzamide;

N-Methyl-N-(4-(4-(1-(pyrid-2-ylmethyl)-1H-benzimidazole-2-carbonyl)piperidin-1-yl)-2-(4-fluorophenyl)butyl)-3,4,5-trimethoxybenzamide;

N-Methyl-N-(4-(4-(1-(pyrid-2-ylmethyl)-1H-benzimidazole-2-carbonyl)piperidin-1-yl)-2-(3,4-difluorophenyl)butyl)benzamide;

N-Methyl-N-(4-(4-(1-(pyrid-2-ylmethyl)-1H-benzimidazole-2-carbonyl)piperidin-1-yl)-2-(3,4-difluorophenyl)butyl)-3,4,5-trimethoxybenzamide;

N-Methyl-N-(4-(4-(1-(pyrid-2-ylmethyl)-1H-benzimidazole-2-carbonyl)piperidin-1-yl)-2-(3-chlorophenyl)butyl)benzamide;

N-Methyl-N-(4-(4-(1-(pyrid-2-ylmethyl)-1H-benzimidazole-2-carbonyl)piperidin-1-yl)-2-(3-chlorophenyl)butyl)-3,4,5-trimethoxybenzamide;

N-Methyl-N-(4-(4-(1-(pyrid-2-ylmethyl)-1H-benzimidazole-2-carbonyl)piperidin-1-yl)-2-(4-chlorophenyl)butyl)benzamide;

N-Methyl-N-(4-(4-(1-(pyrid-2-ylmethyl)-1H-benzimidazole-2-carbonyl)piperidin-1-yl)-2-(4-chlorophenyl)butyl)-3,4,5-trimethoxybenzamide;

N-Methyl-N-(4-(4-(1-(pyrid-2-ylmethyl)-1H-benzimidazole-2-carbonyl)piperidin-1-yl)-2-(3,4-dichlorophenyl)butyl)benzamide;

N-Methyl-N-(4-(4-(1-(pyrid-2-ylmethyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(pyrid-2-ylmethyl)-1H-benzimidazole-2-carbonyl)piperidin-1-yl)-2-(4-methoxyphenyl)butyl)benzamide;

N-Methyl-N-(4-(4-(1-(pyrid-2-ylmethyl)-1H-benzimidazole-2-carbonyl)piperidin-1-yl)-2-(4-methoxyphenyl)butyl)-3,4,5-trimethoxybenzamide;

N-Methyl-N-(4-(4-(1-(pyrid-2-ylmethyl)-1H-benzimidazole-2-carbonyl)piperidin-1-yl)-2-(3-methoxyphenyl)butyl)benzamide;

N-Methyl-N-(4-(4-(1-(pyrid-2-ylmethyl)-1H-benzimidazole-2-carbonyl)piperidin-1-yl)-2-(3-methoxyphenyl)butyl)-3,4,5-trimethoxybenzamide;

N-Methyl-N-(4-(4-(1-(pyrid-2-ylmethyl)-1H-benzimidazole-2-carbonyl)piperidin-1-yl)-2-(3,4-dimethoxyphenyl)butyl)benzamide;

N-Methyl-N-(4-(4-(1-(pyrid-2-ylmethyl)-1H-benzimidazole-2-carbonyl)piperidin-1-yl)-2-(3,4-dimethoxyphenyl)butyl)-3,4,5-trimethoxybenzamide;

N-Methyl-N-(4-(4-(1-(2-oxoxbutyl)-1H-benzimidazole-2-carbonyl)piperidin-1-yl)-2-phenylbutyl)benzamide;

N-Methyl-N-(4-(4-(1-(2-oxoxbutyl)-1H-benzimidazole-2-carbonyl)piperidin-1-yl)-2-phenylbutyl)-3,4,5-trimethoxybenzamide;

N-Methyl-N-(4-(4-(1-(2-oxoxbutyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(2-oxoxbutyl)-1H-benzimidazole-2-carbonyl)piperidin-1-yl)-2-(4-methoxyphenyl)butyl)benzamide;

N-Methyl-N-(4-(4-(1-methyl-1H-benzimidazole-2-carbonyl)piperidin-1-yl)-2-phenylbutyl)benzamide;

N-Methyl-N-(4-(4-(1-methyl-1H-benzimidazole-2-carbonyl)piperidin-1-yl)-2-(3-chlorophenyl)butyl)-3,4,5-trimethoxybenzamide;

N-Methyl-N-(4-(4-(1-methyl-1H-benzimidazole-2-carbonyl)piperidin-1-yl)-2-(4-methoxyphenyl)butyl)benzamide;

N-Methyl-N-(4-(4-(1-(3-(4-carboxyphenyl)propyl)-1H-benzimidazole-2-carbonyl)piperidin-1-yl)-2-(3-chlorophenyl)butyl)-3,4,5-trimethoxybenzamide;

N-Methyl-N-(4-(4-(1-(3-(4-carboxyphenyl)propyl)-1H-benzimidazole-2-carbonyl)piperidin-1-yl)-2-(3,4-dichlorophenyl)butyl)benzamide;

N-Methyl-N-(4-(4-(1-(3-(4-carboxyphenyl)propyl)-1H-benzimidazole-2-carbonyl)piperidin-1-yl)-2-(4-methoxyphenyl)butyl)-3,4,5-trimethoxybenzamide N-Methyl-N-(4-(4-(1-(2-oxopropyl)-1H-benzimidazole-2-carbonyl)piperidin-1-yl)-2-phenylbutyl)benzamide;

N-Methyl-N-(4-(4-(1-(2-oxopropyl)-1H-benzimidazole-2-carbonyl)piperidin-1-yl)-2-phenylbutyl)-3,4,5-trimethoxybenzamide;

N-Methyl-N-(4-(4-(1-(2-oxopropyl)-1H-benzimidazole-2-carbonyl)piperidin-1-yl)-2-(3-chlorophenyl)butyl)-3,4,5-trimethoxybenzamide;

N-Methyl-N-(4-(4-(1-(2-oxopropyl)-1H-benzimidazole-2-carbonyl)piperidin-1-yl)-2-(3,4-dichlorophenyl)butyl)benzamide;

N-Methyl-N-(4-(4-(1-(5-methylfur-2-ylmethyl)-1H-benzimidazole-2-carbonyl)piperidin-1-yl)-2-(4-fluorophenyl)butyl)-3,4,5-trimethoxybenzamide;

N-Methyl-N-(4-(4-(1-(5-methylfur-2-ylmethyl)-1H-benzimidazole-2-carbonyl)piperidin-1-yl)-2-(3-chlorophenyl)butyl)benzamide;

N-Methyl-N-(4-(4-(1-(5-methylfur-2-ylmethyl)-1H-benzimidazole-2-carbonyl)piperidin-1-yl)-2-(3-chlorophenyl)butyl)-3,4,5-trimethoxybenzamide;

N-Methyl-N-(4-(4-(1-(5-methylfur-2-ylmethyl)-1H-benzimidazole-2-carbonyl)piperidin-1-yl)-2-(4-methoxyphenyl)butyl)-3,4,5-trimethoxybenzamide;

N-Methyl-N-(4-(4-(1-(5-hydroxymethylfur-2-ylmethyl)-1H-benzimidazole-2-carbonyl)piperidin-1-yl)-2-phenylbutyl)benzamide;

N-Methyl-N-(4-(4-(1-(5-hydroxymethylfur-2-ylmethyl)-1H-benzimidazole-2-carbonyl)piperidin-1-yl)-2-phenylbutyl)-3,4,5-trimethoxybenzamide;

N-Methyl-N-(4-(4-(1-(5-hydroxymethylfur-2-ylmethyl)-1H-benzimidazole-2-carbonyl)piperidin-1-yl)-2-(3-chlorophenyl)butyl)-3,4,5-trimethoxybenzamide;

N-Methyl-N-(4-(4-(1-(5-hydroxymethylfur-2-ylmethyl)-1H-benzimidazole-2-carbonyl)piperidin-1-yl)-2-(3,4-dichlorophenyl)butyl)benzamide;

N-Methyl-N-(4-(4-(1-(5-hydroxymethylfur-2-ylmethyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(4-carboxybenzyl)-1H-benzimidazole-2-carbonyl)piperidin-1-yl)-2-phenylbutyl)benzamide;

N-Methyl-N-(4-(4-(1-(4-carboxybenzyl)-1H-benzimidazole-2-carbonyl)piperidin-1-yl)-2-(4-fluorophenyl)butyl)benzamide;

N-Methyl-N-(4-(4-(1-(4-carboxybenzyl)-1H-benzimidazole-2-carbonyl)piperidin-1-yl)-2-(4-fluorophenyl)butyl)-3,4,5-trimethoxybenzamide;

N-Methyl-N-(4-(4-(1-(4-carboxybenzyl)-1H-benzimidazole-2-carbonyl)piperidin-1-yl)-2-(3-chlorophenyl)butyl)benzamide;

N-Methyl-N-(4-(4-(1-(4-carboxybenzyl)-1H-benzimidazole-2-carbonyl)piperidin-1-yl)-2-(3,4-dichlorophenyl)butyl)benzamide;

N-Methyl-N-(4-(4-(1-(4-carboxybenzyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(4-methoxycarbonylbenzyl)-1H-benzimidazole-2-carbonyl)piperidin-1-yl)-2-phenylbutyl)-3,4,5-trimethoxybenzamide;

N-Methyl-N-(4-(4-(1-(4-methoxycarbonylbenzyl)-1H-benzimidazole-2-carbonyl)piperidin-1-yl)-2-(4-fluorophenyl)butyl)benzamide;

N-Methyl-N-(4-(4-(1-(4-methoxycarbonylbenzyl)-1H-benzimidazole-2-carbonyl)piperidin-1-yl)-2-(3-chlorophenyl)butyl)benzamide;

N-Methyl-N-(4-(4-(1-(4-methoxycarbonylbenzyl)-1H-benzimidazole-2-carbonyl)piperidin-1-yl)-2-(4-methoxyphenyl)butyl)benzamide;

N-Methyl-N-(4-(4-(1-(3-ethyoxycarbonylpropyl)-1H-benzimidazole-2-carbonyl)piperidin-1-yl)-2-phenylbutyl)benzamide;

N-Methyl-N-(4-(4-(1-(3-ethyoxycarbonylpropyl)-1H-benzimidazole-2-carbonyl)piperidin-1-yl)-2-(4-fluorophenyl)butyl)-3,4,5-trimethoxybenzamide;

N-Methyl-N-(4-(4-(1-(3-ethyoxycarbonylpropyl)-1H-benzimidazole-2-carbonyl)piperidin-1-yl)-2-(4-methoxyphenyl)butyl)-3,4,5-trimethoxybenzamide;

N-Methyl-N-(4-(4-(1-(2-(morpholin-4-yl)ethyl)-1H-benzimidazole-2-carbonyl)piperidin-1-yl)-2-(4-methoxyphenyl)butyl)benzamide;

N-Methyl-N-(4-(4-benzhydrylidenepiperidin-1-yl)-2-phenylbutyl)-3,4,5-trimethoxybenzamide;

N-Methyl-N-(4-(4-benzhydrylidenepiperidin-1-yl)-2-(3,4-dichlorophenyl)butyl)-3,4,5-trimethoxybenzamide;

N-Methyl-N-(4-(4-(1-(fur-3-ylmethyl)-1H-benzimidazole-2-carbonyl)piperidin-1-yl)-2-phenylbutyl)-3,4,5-trimethoxybenzamide N-Methyl-N-(4-(4-(1-(fur-3-ylmethyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-ethyl-1H-benzimidazole-2-carbonyl)piperidin-1-yl)-2-(4-fluorophenyl)butyl)benzamide;

N-Methyl-N-(4-(4-(1-propyl-1H-benzimidazole-2-carbonyl)piperidin-1-yl)-2-(3,4-dichlorophenyl)butyl)benzamide;

N-Methyl-N-(4-(4-(1-butyl-1H-benzimidazole-2-carbonyl)piperidin-1-yl)-2-(3,4-dichlorophenyl)butyl)-3,4,5-trimethoxybenzamide;

N-Methyl-N-(4-(4-(1-(2-carboxyethyl)-1H-benzimidazole-2-carbonyl)piperidin-1-yl)-2-phenylbutyl)benzamide;

N-Methyl-N-(4-(4-(1-(thien-2-ylmethyl)-1H-benzimidazole-2-carbonyl)piperidin-1-yl)-2-(4-fluorophenyl)butyl)benzamide;

N-Methyl-N-(4-(4-(1-(2-(dimethylamino)ethyl)-1H-benzimidazole-2-carbonyl)piperidin-1-yl)-2-(3-chlorophenyl)butyl)benzamide;

N-Methyl-N-(4-(4-(1-(2-phenoxyethyl)-1H-benzimidazole-2-carbonyl)piperidin-1-yl)-2-(3,4-dichlorophenyl)butyl)benzamide;

N-Methyl-N-(4-(4-(1-(imidazol-2-ylmethyl)-1H-benzimidazole-2-carbonyl)piperidin-1-yl)-2-(3-chlorophenyl)butyl)-3,4,5-trimethoxybenzamide;

N-Methyl-N-(4-(4-(1-(2-(3,3-dimethyallyloxy)ethyl)-1H-benzimidazole-2-carbonyl)piperidin-1-yl)-2-(4-fluorophenyl)butyl)-3,4,5-trimethoxybenzamide;

N-Methyl-N-(4-(4-(1-(2-allyloxyethyl)-1H-benzimidazole-2-carbonyl)piperidin-1-yl)-2-phenylbutyl)benzamide;

N-Methyl-N-(4-(4-(1-(2-allyloxyethyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-phenylbutyl)benzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-phenylbutyl)-3,4,5-trimethoxybenzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(4-fluorophenyl)butyl)benzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(4-fluorophenyl)butyl)-3,4,5-trimethoxybenzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(3,4-difluorophenyl)butyl)benzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(3,4-difluorophenyl)butyl)-3,4,5-trimethoxybenzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(3-chlorophenyl)butyl)benzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(3-chlorophenyl)butyl)-3,4,5-trimethoxybenzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(4-chlorophenyl)butyl)benzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(4-chlorophenyl)butyl)-3,4,5-trimethoxybenzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(3,4-dichlorophenyl)butyl)benzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(4-methoxyphenyl)butyl)benzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(4-methoxyphenyl)butyl)-3,4,5-trimethoxybenzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(3-methoxyphenyl)butyl)benzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(3-methoxyphenyl)butyl)-3,4,5-trimethoxybenzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(3,4-dimethoxyphenyl)butyl)benzamide;

N-Methyl-N-(4-(4-(1-(2-(2,2,2-trifluoroethoxy)ethyl)-1H-benzimidazole-2-carbonyl)-1H-benzimidazole-2-carbonyl)piperidin-1-yl)-2-(3,4-dimethoxyphenyl)butyl)-3,4,5-trimethoxybenzamide;

N-Methyl-N-(4-(4-(1-(2-(2,2,2-trifluoroethoxy)ethyl)-1H-benzimidazole-2-carbonyl)piperidin-1-yl)-2-phenylbutyl)-2-methoxy-5-(4H-triazol-4-yl)benzamide;

N-Methyl-N-(4-(4-(1-(2-(2,2,2-trifluoroethoxy)ethyl)-1H-benzimidazole-2-carbonyl)piperidin-1-yl)-2-(3,4-difluorophenyl)butyl)-2-methoxy-5-(4H-triazol-4-yl)benzamide;

N-Methyl-N-(4-(4-(1-(2-(2,2,2-trifluoroethoxy)ethyl)-1H-benzimidazole-2-carbonyl)piperidin-1-yl)-2-(3,4-dichlorophenyl)butyl)-2-methoxy-5-(4H-triazol-4-yl)benzamide;

N-Methyl-N-(4-(4-(1-(2-(2,2,2-trifluoroethoxy)ethyl)-1H-benzimidazole-2-carbonyl)piperidin-1-yl)-2-(3-methoxyphenyl)butyl)-2-methoxy-5-(4H-triazol-4-yl)benzamide;

N-Methyl-N-(4-(4-(1-(2-(2,2,2-trifluoroethoxy)ethyl)-1H-benzimidazole-2-carbonyl)piperidin-1-yl)-2-phenylbutyl)-2-methoxy-5-(1H-tetrazol-1-yl)benzamide;

N-Methyl-N-(4-(4-(1-(2-(2,2,2-trifluoroethoxy)ethyl)-1H-benzimidazole-2-carbonyl)piperidin-1-yl)-2-(3,4-difluorophenyl)butyl)-2-methoxy-5-(1H-tetrazol-1-yl)benzamide;

N-Methyl-N-(4-(4-(1-(2-(2,2,2-trifluoroethoxy)ethyl)-1H-benzimidazole-2-carbonyl)piperidin-1-yl)-2-(3,4-dichlorophenyl)butyl)-2-methoxy-5-(1H-tetrazol-1-yl)benzamide;

N-Methyl-N-(4-(4-(1-(2-(2,2,2-trifluoroethoxy)ethyl)-1H-benzimidazole-2-carbonyl)piperidin-1-yl)-2-(3-methoxyphenyl)butyl)-2-methoxy-5-(1H-tetrazol-1-yl)benzamide;

N-Methyl-N-(4-(4-(1-(2,2,2-trifluoroethyl)-1H-benzimidazole-2-carbonyl)-1H-benzimidazole-2-carbonyl)piperidin-1-yl)-2-phenylbutyl)benzamide;

N-Methyl-N-(4-(4-(1-(2,2,2-trifluoroethyl)-1H-benzimidazole-2-carbonyl)-1H-benzimidazole-2-carbonyl)piperidin-1-yl)-2-phenylbutyl)-3,4,5-trimethoxybenzamide;

N-Methyl-N-(4-(4-(1-(2,2,2-trifluoroethyl)-1H-benzimidazole-2-carbonyl)-1H-benzimidazole-2-carbonyl)piperidin-1-yl)-2-(3,4-difluorophenyl)butyl)-3,4,5-trimethoxybenzamide;

N-Methyl-N-(4-(4-(1-(2,2,2-trifluoroethyl)-1H-benzimidazole-2-carbonyl)-1H-benzimidazole-2-carbonyl)piperidin-1-yl)-2-(3,4-dichlorophenyl)butyl)benzamide;

N-Methyl-N-(4-(4-(1-(2,2,2-trifluoroethyl)-1H-benzimidazole-2-carbonyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(2,2,2-trifluoroethyl)-1H-benzimidazole-2-carbonyl)piperidin-1-yl)-2-phenylbutyl)-2-methoxy-5-(4H-triazol-4-yl)benzamide;

N-Methyl-N-(4-(4-(1-(2,2,2-trifluoroethyl)-1H-benzimidazole-2-carbonyl)piperidin-1-yl)-2-(3,4-difluorophenyl)butyl)-2-methoxy-5-(4H-triazol-4-yl)benzamide;

N-Methyl-N-(4-(4-(1-(2,2,2-trifluoroethyl)-1H-benzimidazole-2-carbonyl)piperidin-1-yl)-2-(3,4-dichlorophenyl)butyl)-2-methoxy-5-(4H-triazol-4-yl)benzamide;

N-Methyl-N-(4-(4-(1-(2,2,2-trifluoroethyl)-1H-benzimidazole-2-carbonyl)piperidin-1-yl)-2-phenylbutyl)-2-methoxy-5-(1H-tetrazol-1-yl)benzamide;

N-Methyl-N-(4-(4-(1-(2,2,2-trifluoroethyl)-1H-benzimidazole-2-carbonyl)piperidin-1-yl)-2-(3,4-difluorophenyl)butyl)-2-methoxy-5-(1H-tetrazol-1-yl)benzamide;

N-Methyl-N-(4-(4-(1-(2,2,2-trifluoroethyl)-1H-benzimidazole-2-carbonyl)piperidin-1-yl)-2-(3,4-dichlorophenyl)butyl)-2-methoxy-5-(1H-tetrazol-1-yl)benzamide;

N-Methyl-N-(4-(4-(1-(4,4,4-trifluorobutyl)-1H-benzimidazole-2-carbonyl)-1H-benzimidazole-2-carbonyl)piperidin-1-yl)-2-phenylbutyl)benzamide;

N-Methyl-N-(4-(4-(1-(4,4,4-trifluorobutyl)-1H-benzimidazole-2-carbonyl)-1H-benzimidazole-2-carbonyl)piperidin-1-yl)-2-phenylbutyl)-3,4,5-trimethoxybenzamide;

N-Methyl-N-(4-(4-(1-(4,4,4-trifluorobutyl)-1H-benzimidazole-2-carbonyl)-1H-benzimidazole-2-carbonyl)piperidin-1-yl)-2-(3,4-difluorophenyl)butyl)-3,4,5-trimethoxybenzamide;

N-Methyl-N-(4-(4-(1-(4,4,4-trifluorobutyl)-1H-benzimidazole-2-carbonyl)-1H-benzimidazole-2-carbonyl)piperidin-1-yl)-2-(3,4-dichlorophenyl)butyl)benzamide;

N-Methyl-N-(4-(4-(1-(4,4,4-trifluorobutyl)-1H-benzimidazole-2-carbonyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(4,4,4-trifluorobutyl)-1H-benzimidazole-2-carbonyl)piperidin-1-yl)-2-phenylbutyl)-2-methoxy-5-(4H-triazol-4-yl)benzamide;

N-Methyl-N-(4-(4-(1-(4,4,4-trifluorobutyl)-1H-benzimidazole-2-carbonyl)piperidin-1-yl)-2-(3,4-difluorophenyl)butyl)-2-methoxy-5-(4H-triazol-4-yl)benzamide;

N-Methyl-N-(4-(4-(1-(4,4,4-trifluorobutyl)-1H-benzimidazole-2-carbonyl)piperidin-1-yl)-2-(3,4-dichlorophenyl)butyl)-2-methoxy-5-(4H-triazol-4-yl)benzamide;

N-Methyl-N-(4-(4-(1-(4,4,4-trifluorobutyl)-1H-benzimidazole-2-carbonyl)piperidin-1-yl)-2-phenylbutyl)-2-methoxy-5-(1H-tetrazol-1-yl)benzamide;

N-Methyl-N-(4-(4-(1-(4,4,4-trifluorobutyl)-1H-benzimidazole-2-carbonyl)piperidin-1-yl)-2-(3,4-difluorophenyl)butyl)-2-methoxy-5-(1H-tetrazol-1-yl)benzamide;

N-Methyl-N-(4-(4-(1-(4,4,4-trifluorobutyl)-1H-benzimidazole-2-carbonyl)piperidin-1-yl)-2-(3,4-dichlorophenyl)butyl)-2-methoxy-5-(1H-tetrazol-1-yl)benzamide;

N-Methyl-N-(4-(4-(1-(allyl)-1H-benzimidazole-2-carbonyl)-1H-benzimidazole-2-carbonyl)piperidin-1-yl)-2-phenylbutyl)benzamide;

N-Methyl-N-(4-(4-(1-(allyl)-1H-benzimidazole-2-carbonyl)-1H-benzimidazole-2-carbonyl)piperidin-1-yl)-2-phenylbutyl)-3,4,5-trimethoxybenzamide;

N-Methyl-N-(4-(4-(1-(allyl)-1H-benzimidazole-2-carbonyl)-1H-benzimidazole-2-carbonyl)piperidin-1-yl)-2-(3,4-dichlorophenyl)butyl)benzamide;

N-Methyl-N-(4-(4-(1-(allyl)-1H-benzimidazole-2-carbonyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(allyl)-1H-benzimidazole-2-carbonyl)piperidin-1-yl)-2-(3,4-dichlorophenyl)butyl)-2-methoxy-5-(4H-triazol-4-yl)benzamide;

N-Methyl-N-(4-(4-(1-(allyl)-1H-benzimidazole-2-carbonyl)piperidin-1-yl)-2-(3,4-dichlorophenyl)butyl)-2-methoxy-5-(1H-tetrazol-1-yl)benzamide;

N-Methyl-N-(4-(4-(1-(but-2-en-1-yl)-1H-benzimidazole-2-carbonyl)-1H-benzimidazole-2-carbonyl)piperidin-1-yl)-2-phenylbutyl)benzamide;

N-Methyl-N-(4-(4-(1-(but-2-en-1-yl)-1H-benzimidazole-2-carbonyl)-1H-benzimidazole-2-carbonyl)piperidin-1-yl)-2-phenylbutyl)-3,4,5-trimethoxybenzamide;

N-Methyl-N-(4-(4-(1-(but-2-en-1-yl)-1H-benzirnidazole-2-carbonyl)-1H-benzimidazole-2-carbonyl)piperidin-1-yl)-2-(3,4-dichlorophenyl)butyl)benzamide;

N-Methyl-N-(4-(4-(1-(but-2-en-1-yl)-1H-benzimidazole-2-carbonyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(but-2-en-1-yl)-1H-benzimidazole-2-carbonyl)piperidin-1-yl)-2-(3,4-dichlorophenyl)butyl)-2-methoxy-5-(4H-triazol-4-yl)benzamide;

N-Methyl-N-(4-(4-(1-(but-2-en-1-yl)-1H-benzimidazole-2-carbonyl)piperidin-1-yl)-2-(3,4-dichlorophenyl)butyl)-2-methoxy-5-(1H-tetrazol-1-yl)benzamide;

N-Methyl-N-(4-(4-(1-(3-methylbut-2-en-1-yl)-1H-benzimidazole-2-carbonyl)-1H-benzimidazole-2-carbonyl)piperidin-1-yl)-2-phenylbutyl)benzamide;

N-Methyl-N-(4-(4-(1-(3-methylbut-2-en-1-yl)-1H-benzimidazole-2-carbonyl)-1H-benzimidazole-2-carbonyl)piperidin-1-yl)-2-phenylbutyl)-3,4,5-trimethoxybenzamide;

N-Methyl-N-(4-(4-(1-(3-methylbut-2-en-1-yl)-1H-benzimidazole-2-carbonyl)-1H-benzimidazole-2-carbonyl)piperidin-1-yl)-2-(3,4-dichlorophenyl)butyl)benzamide;

N-Methyl-N-(4-(4-(1-(3-methylbut-2-en-1-yl)-1H-benzimidazole-2-carbonyl)-1H-benzimidazole-2-carbonyl)piperidin-1-yl)-2-(3,4-dichlorophenyl)butyl)-3,4,5-trimethoxybenzamide;

N-Methyl-N-(4-(4-(1-(3-methylbut-2-en-1-yl)-1H-benzimidazole-2-carbonyl)piperidin-1-yl)-2-(3,4-dichlorophenyl)butyl)-2-methoxy-5-(4H-triazol-4-yl)benzamide;

N-Methyl-N-(4-(4-(1-(3-methylbut-2-en-1-yl)-1H-benzimidazole-2-carbonyl)piperidin-1-yl)-2-(3,4-dichlorophenyl)butyl)-2-methoxy-5-(1H-tetrazol-1-yl)benzamide.

A general synthetic procedure for preparing these compounds of formula (1) is set forth in Reaction Scheme A. The reagents and starting materials are readily available to one of ordinary skill in the art. In Reaction Scheme A, all substituents, unless otherwise indicated, are as previously defined.

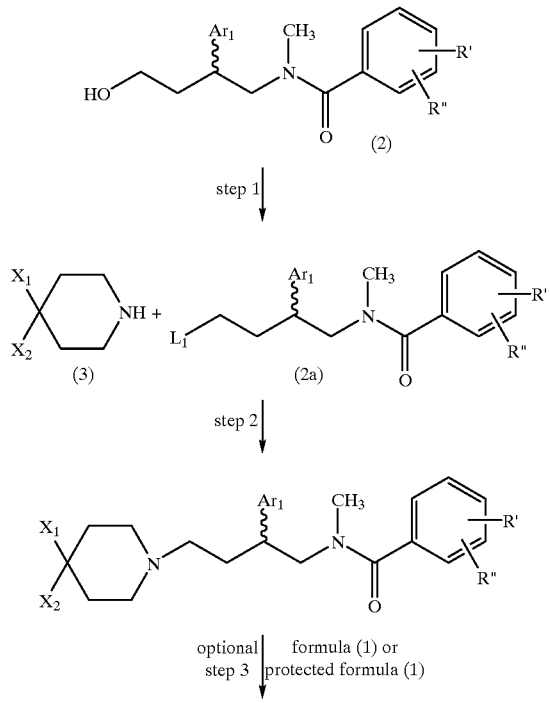

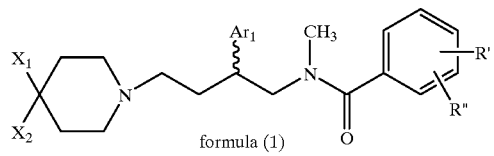

In Reaction Scheme A, step 1, the hydroxy group of an appropriate alcohol of structure 2 is converted to an appropriate leaving group to give a compound of structure 2a. An appropriate alcohol of structure 2 is one in which the stereochemistry is as desired in the final product of formula (1) and R', R", and Ar$_1$ are as desired in the final product of formula (1). Alternately, an appropriate alcohol of structure 2 can be one in which the stereochemistry gives rise after resolution to stereochemistry as desired in the final product of formula (1) and R', R', and Ar$_1$ are as desired in the final product of formula (1). An appropriate alcohol of structure 2 can also be one in which the stereochemistry and R' and R' are as desired in the final product of formula (1) and Ar$_1$ gives rise upon deprotection to Ar$_1$ as desired in the final product of formula (1). Alternately, an appropriate alcohol of structure 2 can also be one in which the stereochemistry gives rise after resolution to stereochemistry as desired in the final product of formula (1), R' and R" are as desired in the final product of formula (1), and Ar$_1$ gives rise upon deprotection to Ar$_1$ as desired in the final product of formula (1).

An appropriate alcohol of structure 2 can be prepared by methods described herein and by methods which are well known and appreciated in the art, such as U.S. Pat. Nos. 5,317,020 and 5,236,921, which are hereby incorporated by reference; European Patent Application Nos. 0 428 434, published May 22, 1991, 0 630 887, published Dec. 28, 1994, and 0 559 538, published Sep. 8, 1993; PCT Application Nos. WO 9417045, published Aug. 4, 1994 and WO 95415961, published Jun. 15, 1995; and *Biooraanic & Medicinal Chemistry Letters*, 3, 925–930 (1993).

An appropriate alcohol of structure 2 can also be prepared by reduction of the aldehyde prepared from a homologous alkene by formation of the cis-diol followed by oxidative cleavage, as described in *Bioorganic & Medicinal Chemistry Letters*, 3, 319–322 (1993) or by methods analogous thereto, such as described in *J. Am. Chem. Soc.*, 104, 1737 (1982) and *Tet.*, 44, 5525 (1988) or by the action of ozone on a homologous alkene by methods well known in the art. Reagents for such reductions of aldehydes to an alcohols, are well known and appreciated in the art, such as soduim borohydride.

An appropriate leaving group, L$_1$, is one which can be displaced by a piperidine of structure 3 to give rise to a compound of formula (1). Appropriate leaving groups, L$_1$, include but are not limited to chloro, bromo, iodo, mesylate, tosylate, benzenesulfonate, and the like. The conversion of hydroxy groups to leaving groups such as chloro, bromo, iodo, mesylate, tosylate, and benzenesulfonate is well known and appreciated in the art.

For example, compounds in which L$_1$ is bromo are formed by contacting an appropriate alcohol of structure 2 with 1.0 to 1.5 molar equivalents of carbon tetrabromide and 1.0 to 1.75 molar equivalents triphenylphosphine. (P. J. Kocienski et al. *J. Org. Chem.*, 42, 353–355 (1977)). The reaction is carried out by combining the alcohol of structure 2 with carbon tetrabromide in a suitable solvent, such as dichloromethane or chloroform and then adding a solution of triphenylphosphine in a suitable solvent, such as dichloromethane or chloroform. Generally the reaction is carried out at temperatures of from −10° C. to ambient temperature. Generally, the reactions require from 5 minutes to 24 hours. The product can be isolated and purified by techniques well known in the art, such as extraction, evaporation, trituration, chromatography, and recrystallization.

Compounds in which $L_1$ is bromo are also formed by contacting an appropriate alcohol of structure 2 with a slight molar excess of triphenylphosphine dibromide. (R. F Borch et al. *J. Am. Chem. Soc.*, 99, 1612–1619 (1977)). The reaction may be carried out by contacting an appropriate alcohol of structure 2 with preformed triphenylphosphine dibromide. The reaction is carried out in a suitable solvent, such as tetrahydrofuran and diethyl ether. The reaction is carried out in the presence of a suitable base, such as pyridine. Generally the reaction is carried out at temperatures of from 0° C. to 50° C. Generally, the reactions require from 5 minutes to 24 hours. The product can be isolated and purified by techniques well known in the art, such as extraction, evaporation, trituration, chromatography, and recrystallization.

Alternately, for example, compounds in which $L_1$ is mesylate are formed by contacting an appropriate alcohol of structure 2 with a molar excess of methanesulfonyl chloride. The reaction is carried out in a suitable solvent, such as dichloromethane, chloroform, toluene, benzene, or pyridine. The reaction is carried out in the presence of a suitable base, such as triethylamine, diisopropylethylamine, or pyridine. Generally the reaction is carried out at temperatures of from −20° C. to 50° C. Generally, the reactions require from 1 hour to 24 hours. The product can be isolated and purified by techniques well known in the art, such as extraction, evaporation, trituration, chromatography, and recrystallization.

Compounds of structure 2a in which $L_1$ is iodo can be prepared from compounds of structure 2a in which $L_1$ is mesylate, chloro, or bromo by an exchange reaction, such as the Finkelstein reaction.

For example, a compound of structure 2a in which $L_1$ is mesylate, chloro, or bromo is contacted with from 1.0 to 10.0 molar equivalents of an iodide salt, such as sodium iodide or potassium iodide. The reaction is carried out in a suitable solvent, such as acetone, butanone, tetrahydrofuran, tetrahydrofuran/water mixtures, toluene, and acetonitrile. Generally, the reaction is carried out at temperatures of from ambient temperature to the refluxing temperature of the solvent. Generally, the reactions require from 1 hour to 24 hours. The product can be isolated and purified by techniques well known in the art, such as extraction, evaporation, trituration, chromatography, and recrystallization.

In Reaction Scheme A, step 2, the compound of structure 2a reacts with an appropriate piperidine compound of structure 3 or a salt thereof to give a protected compound of formula (1) or a compound of formula (1).

An appropriate piperidine of structure 3 or salt thereof is one in which $X_1$ and $X_2$ are as desired in the final product of formula (1) or $X_1$ and $X_2$ give rise after modification or deprotection to $X_1$ and $X_2$ are as desired in the final product of formula (1). Appropriate piperidines of structure 3 are well known and appreciated in the art and are described in International Patent Application (PCT) No. WO 92/06086, U.S. Pat. No. 4,908,372, Mar. 13, 1990, U.S. Pat. No. 4,254,129, Mar. 3, 1981, U.S. Pat. No. 4,254,130, Mar. 3, 1981, U.S. Pat. No. 4,285,958, Apr. 25, 1981, U.S. Pat. No. 4,550,116, Oct. 29, 1985, and European Patent Application No. 0 533 344, published Mar. 24, 1993; and by methods analogous to those methods by carrying out suitable deprotections, protections, and alkylations, as are well known in the art, in the order and number required for formation of an appropriate piperidine of structure 3. Appropriate piperidines of structure 3 wherein $X_1$ and $Z_1$ taken together form a second bond between the carbon atoms bearing $X_1$ and $Z_1$ may be prepared by dehydration of the corresponding compound wherein $X_1$ is hydroxy by procedures generally known in the art, such as refluxing in strongly acidic solution. Appropriate piperidines of structure 3 may also be prepared by addition of readily available organometallic reagents to suitably protected 4-piperidinones or suitably protected isonipecotic acid derivatives, by methods known in the art such as described by G. D. Maynard et al., *Bioorg. and Med. Chem. Lets.*, 3, 753–756 (1993). Appropriate piperidines of structure 3 may also be prepared from readily available starting materials or by methods known analogously in the art, such as described by C. G. Wahlgren and A. W. Addison, *J. Heterocyclic Chem.*, 26, 541 (1989), R. Iemura and H. Ohtka, *Chem. Pharm. Bull.*, 37, 967–972 (1989), and K. Ito and G. Tsukamoto, *J. Heterocyclic Chem.*, 24, 31 (1987), by carrying out suitable deprotections, protections, and alkylations, as are well known in the art, in the order and number required for formation of an appropriate piperidine of structure 3.

For example, the compound of structure 2a is contacted with an appropriate piperidine compound of structure 3 or salt thereof to give a protected compound of formula (1) or a compound of formula (1). The reaction is carried out in a suitable solvent, such as dioxane, tetrahydrofuran, tetrahydrofuran/water mixtures, acetone, acetone/water mixtures, ethyl acetate, ethyl acetate/water mixtures, pyridine, acetonitrile, toluene, toluene/water mixtures, chlorobenzene, or dimethylformamide. The reaction is carried out in the presence of from 1.0 to 6.0 molar equivalents of a suitable base, such as sodium carbonate, sodium bicarbonate, potassium carbonate, potassium bicarbonate, triethylamine, pyridine, or diisopropylethylamine. When a salt of an appropriate piperidine of structure 3 is used, an additional molar excess of a suitable base may be required. The reaction may be facilitated by the addition of a catalytic amount, 0.1 to 0.5 molar equivalents, of an iodide salt, such as sodium iodide, potassium iodide, or tetrabutyl ammonium iodide. The reaction is generally carried out at temperatures of from ambient temperature to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme A, optional step 3, a compound of formula (1) or a protected compound of formula (1) in which Z is hydrogen is modified to give a a compound of formula (1) or a protected compound of formula (1) in which Z is not hydrogen. Also encompassed by Reaction Scheme A, optional step 3, a protected compound of formula (1) is deprotected to give a compound of formula (1).

A modification reaction encompasses the formation of amides and the alkylation of the benzimidazole nitrogen. The formation of amides from esters and acids is well known and appreciated in the art. The alkylation of a benzimidazole nitrogen using a suitable alkylating agent is well known and appreciated in the art. The reaction is carried out in a suitable solvent, such as dioxane, tetrahydrofuran, tetrahydrofuran/water mixtures, acetone, or acetonitrile. A suitable alkylating agent is one which transfers the group Z or $(CH_2)_p Ar_2$ as desired in the final product of formula (1) or a protected group Z or $(CH_2)_pAr_2$ which gives rise after deprotection to Z or $(CH_2)_pAr_2$ as desired in the final product of formula (1). The reaction is carried out in the presence of from 1.0 to 6.0 molar equivalents of a suitable base, such as sodium carbonate, sodium bicarbonate, potassium carbonate, potassium bicarbonate, triethylamine, 1,8-diazabicyclo[5.4.0]undec-7-ene, 1,5-diazabicyclo[4.3.0]non-5-ene, potassium bis(trimethylsilyl)amide, lithium bis(trimethylsilyl)amide, or diisopropylethylamine. The reaction is generally carried out at temperatures of from ambient temperature to the refluxing temperature of the solvent. Generally, the reactions require 1 to 72 hours. The product can be isolated and purified by techniques well known in the art, such as extraction, evaporation, trituration, chromatography, and recrystallization.

Alternately, the compounds of formula (1) or a protected compound of formula (1) in which Z is hydrogen and having a benzimidazole-2-carbonyl can be alkylated by the Mitsunobu reaction using a suitable alcohol. A suitable alcohol is one which transfers the group Z or $(CH_2)_pAr_2$ as desired in the final product of formula (1) or a protected group Z or $(CH_2)_pAr_2$ which gives rise after deprotection to Z or $(CH_2)_pAr_2$ as desired in the final product of formula (1).

A deprotection reaction, such as the removal of hydroxy protecting groups or hydrolysis of an ester, utilizing suitable protecting groups such as those described in *Protecting Groups in Organic Synthesis* by T. Greene is well known and appreciated in the art.

A general synthetic procedure for preparing the alcohols of formula 2 is set forth in Reaction Scheme B. The reagents and starting materials are readily available to one of ordinary skill in the art. In Scheme B, all substituents, unless otherwise indicated, are as previously defined.

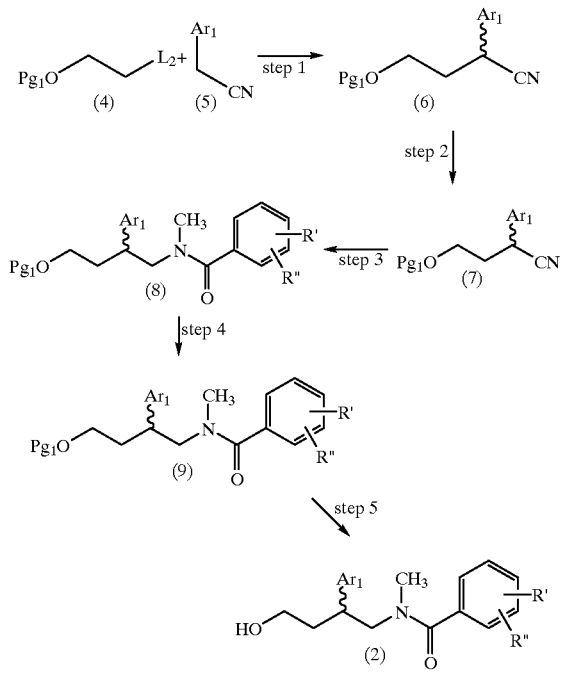

In Reaction Scheme B, step 1, an appropriate nitrile of structure 5 is alkylated with an appropriate protected alcohol of structure 4 to give an 4-(protected-hydroxy)butyronitrile of structure 6.

An appropriate nitrile of structure 5 is one in which $Ar_1$ is as desired in the final product of formula (1) or $Ar_1$ gives rise after deprotection to $Ar_1$ as desired in the final product of formula (1). An appropriate protected alcohol of structure 4 is one in which the leaving group, $L_2$, can be displaced by an anion derived from an appropriate nitrile of structure 5. Suitable leaving groups include but are not limited to chloro, bromo, iodo, and mesylate with bromo and iodo being preferred. The selection and use of a suitable hydroxy protecting group, $Pg_1$, such as those described in *Protecting Groups in Organic Synthesis* by T. Greene are well known and appreciated in the art. The use of tetrahydropyran-2-yl and t-butyldimethylsilyl hydroxy protecting groups are generally preferred.

For example, the appropriate nitrile of structure 5 is contacted with 0.8 to 1.2 molar equivalents of the appropriate protected alcohol of structure 4 under phase transfer catalysis conditions. The reaction is carried out in the presence of a 2 to 10 fold molar excess of a suitable base, such as sodium hydroxide or potassium hydroxide. The reaction is carried out in a solvent, such as water, ethyl acetate/water mixtures, dichloromethane/water mixtures, or tetrahydrofuran/water mixtures. The reaction is carried out in the presence of a suitable phase transfer catalyst, such as benzyltriethylammonium chloride, benzyltriethylammonium bromide, benzyltriethylammonium iodide, benzyltrimethylammonium chloride, benzyltributylammonium chloride, tetrabutylammonium chloride, tetrabutylammonium bromide, tetrabutylammonium iodide, tetrabutylammonium hydrogen sulfate, and the like. The reaction is generally carried out at temperatures of from $-20°$ C. to $60°$ C. Generally, the reactions require 1 to 72 hours. The product can be isolated and purified by techniques well known in the art, such as extraction, evaporation, trituration, chromatography, and recrystallization.

Alternately, for example, the appropriate nitrile of structure 5 is contacted with 1.0 to 1.2 molar equivalents of the appropriate protected alcohol of structure 4. The reaction is carried out in the presence of an equimolar amount of a suitable base, such as sodium hydride, sodium bis(trimethylsilyl)amide, potassium bis(trimethylsilyl)amide, potassium t-butoxide, s-butyl lithium, and lithium diisopropylamide. The reaction is carried out in a solvent, such as dimethylformamide or tetrahydrofuran. The reaction is generally carried out at temperatures of from $-78°$ C. to $0°$ C. Generally, the reactions require 1 to 72 hours. The product can be isolated and purified by techniques well known in the art, such as extraction, evaporation, distillation, trituration, chromatography, and recrystallization.

In Reaction Scheme B, step 2, the 4-(protected-hydroxy)butyronitrile of structure 6 is reduced to give an amino compound of structure 7.

For example, the 4-(protected-hydroxy)butyronitrile of structure 6 is contacted with an excess of an appropriate reducing agent, such as sodium borohydride in the presence of cobalt (II) chloride hexahydrate or hydrogen in the presence of a suitable catalyst, such as Raney nickel or platinum oxide. For compounds of structure 6 in which $Ar_1$ is thienyl or pyridyl, sodium borohydride in the presence of cobalt (II) chloride hexahydrate is preferred.

When sodium borohydride in the presence of cobalt chloride is used, the reaction is carried out in a suitable solvent, such as methanol, or ethanol. The reaction is generally carried out at temperatures of from $0°$ C. to $50°$ C. Generally, the reactions require 1 to 72 hours. The product can be isolated and purified by techniques well known in the art, such as extraction with aqueous acid, evaporation, trituration, distillation, chromatography, and recrystallization.

When Raney nickel is used, the reaction is carried out in a suitable solvent containing ammonia, such as ethanol/ aqueous ammonium hydroxide or methanol/aqueous ammonium hydroxide. The reaction is generally carried out at temperatures of from ambient temperature to 70° C. The reaction is carried out with hydrogen at pressures of from 15 psi to 120 psi in an apparatus designed for carrying out reactions under pressure, such as a Parr hydrogenation apparatus. The product can be isolated by carefully removing the catalyst by filtration and evaporation. The product can be purified by extraction, evaporation, trituration, chromatography, and recrystallization.

When platinum oxide is used, the reaction is carried out in a suitable solvent such as ethanol, methanol, chloroform, ethanol/chloroform mixtures, or methanol/chloroform mixtures. The reaction is generally carried out at temperatures of from ambient temperature to 50° C. The reaction is carried out with hydrogen at pressures of from 15 psi to 120 psi in an apparatus designed for carrying out reactions under pressure, such as a Parr hydrogenation apparatus. Generally, the reaction requires 8 to 48 hours. The product can be purified by extraction, evaporation, trituration, chromatography, and recrystallization.

In Reaction Scheme B, step 3, the amino compound of structure 7 is benzoylated with an appropriate benzoylating agent to give a benzamide of structure 8. An appropriate benzoylating agent is an agent capable of transferring a benzoyl group or substituted benzoyl group, such as a benzoyl halide, substituted benzoyl halide, benzoyl anhydride, substituted benzoyl anhydride, benzoyl mixed anhydride, or substituted benzoyl mixed anhydride to give a benzamide of structure 8. An appropriate benzoylating agent gives a benzamide of structure 8 in which R' and R" are as desired in the final product of formula (1).

For example, the amino compound of structure 7 is contacted with 1 to 1.5 molar equivalents of an appropriate benzoylating agent. The reaction is carried out in a suitable solvent, such as dichloromethane, tetrahydrofuran, acetonitrile, dimethylformamide, or pyridine. The reaction is carried out in the presence of a base, such as sodium carbonate, sodium bicarbonate, triethylamine, N-methylmorpholine, diisopropylethylamine, or pyridine. The reaction is generally carried out at temperatures of from –20° C. to 50° C. Generally, the reactions require 1 to 6 hours. The product can be isolated and purified by techniques well known in the art, such as extraction, evaporation, trituration, chromatography, and recrystallization.

Alternately, for example, the amino compound of structure 7 is contacted with 1 to 1.5 molar equivalents of an appropriate benzoylating agent under Schotten-Baumann conditions. The reaction is carried out in a suitable solvent, such as ethyl acetate/water mixtures, acetone/water mixtures, tetrahydrofuran/water mixtures, or dichloromethane/water mixtures. The reaction is carried out in the presence of a base, such as sodium carbonate, sodium bicarbonate, potassium carbonate, potassium bicarbonate, or sodium hydroxide. The reaction is generally carried out at temperatures of from 0° C. to the refluxing temperature of the solvent. Generally, the reactions require 1 to 6 hours. The product can be isolated and purified by techniques well known in the art, such as extraction, evaporation, trituration, chromatography, and recrystallization.

In Reaction Scheme B, step 4, a benzamide of structure 8 is methylated with an appropriate methylating agent to give a N-methylbenzamide of structure 9. An appropriate methylating agent is one that transfers a methyl to a benzamide of structure 8, including iodomethane, bromomethane, dimethylsulfate, trimethyloxonium tetrafluoroborate, and the like.

For example, a benzamide of structure 8 is contacted with 1 to 4 molar equivalents of the appropriate methylating agent. The reaction is carried out in the presence of from 1 to 4 molar equivalents of a suitable base, such as n-butyl lithium, sec-butyl lithium, sodium hydride, sodium bis(trimethylsilyl)amide, potassium t-butoxide, and lithium diisopropylamide with sodium hydride, sodium bis(trimethylsilyl)amide, and sec-butyl lithium being preferred. The reaction is carried out in a solvent, such as dimethylformamide or tetrahydrofuran. The reaction is generally carried out at temperatures of from –20° C. to 60° C. Generally, the reactions require 1 to 72 hours. The product can be isolated and purified by techniques well known in the art, such as extraction, evaporation, trituration, chromatography, and recrystallization.

In Reaction Scheme B, step 5, the N-methylbenzamide of structure 9 is deprotected to give an alcohol of structure 2. A deprotection reaction, such as the removal of hydroxy protecting groups utilizing suitable protecting groups such as those described in *Protecting Groups in Organic Synthesis* by T. Greene is well known and appreciated in the art.

The following examples and preparations present typical syntheses of the compounds of formula (1). These examples are understood to be illustrative only and are not intended to limit the scope of the invention in any way.

PREPARATION 1

Synthesis of 4-(1H-benzimidazole-2-carbonyl) piperidine hydriodic acid salt

Combine piperidine-4-carboxylic acid (500 g), water (4.2 L), t-butanol (4 L), and 50% aqueous sodium hydroxide solution (386 g). Add portionwise, di-t-butyldicarbonate (930 g). After 20 hours, concentrate the reaction mixture in vacuo to about one half the volume. Slowly add 10% aqueous hydrochloride solution until the pH is about 4. Extract with diethyl ether (3×4 L). Dry the organic layer over $MgSO_4$, filter and evaporate on a steam bath to a volume of about 4 L. Add ethyl acetate (4 L) and evaporate on a steam bath to a volume of about 4 L. Filter and continue to evaporate on a steam bath to a volume of about 2 L. Cool and filter to obtain 1-(t-butoxycarbonyl)piperidine-4-carboxylic acid.

Combine 1-(t-butoxycarbonyl)piperidine-4-carboxylic acid (813.7 g) and dichloromethane (6 L). Add portionwise, carbonyldiimidazole (633.1 g). After 1 hour, add N-methyl-O-methylhydroxylamine hydrochloride (380.5 g). After 56 hours, extract the reaction mixture with 5% aqueous hydrochloric acid solution and 5% aqueous sodium bicarbonate solution. Dry the organic layer over $MgSO_4$, filter, and evaporate in vacuo to obtain 1-(t-butoxycarbonyl) piperidine-4-(N-methyl-O-methyl)hydroxamic acid.

Combine benzimidazole (57.8 g, 490 mmol) and dimethylformamide (570 mL). Cool using an ice bath to about 20° C. Add portionwise, sodium hydride (20.2 g, 60% in oil, 500 mmol) at such a rate that the temperature of the reaction mixture remains at about 20° C. After the addition of sodium hydride is complete, allow to stir for 1 hour. Add a solution of 2-(trimethylsilyl)ethoxymethyl chloride (60 g, 360 mmol) in dimethylformamide (60 mL) at such a rate that the temperature of the reaction mixture remains below 20° C. After 18 hours, add dropwise, water (50 mL). When the addition is complete, pour the reaction mixture into water (2 L). Extract repeatedly with diethyl ether. Combine the organic layers and extract with water. Dry the organic layer over $MgSO_4$, filter, and evaporate in vacuo to obtain 1-((2-trimethylsilyl)ethoxymethyl)-1H-benzimidazole.

Combine 1-((2-trimethylsilyl)ethoxymethyl)-1H-benzimidazole (91.2 g, 367 mmol) and tetrahydrofuran (500 mL). Cool to −78° C. using a dry-ice/acetone bath. Add a solution of n-butyllithium (146 mL, 2.5 M in hexane, 367 mmol) at such a rate that the temperature of the reaction mixture remains at about −70° C. After the addition of n-butyllithium is complete allow to stir for 30 minutes at −78° C. Add dropwise, a solution of 1-(t-butoxycarbonyl)-piperidine-4-(N-methyl-O-methyl)hydroxamic acid (99.9 g, 367 mmol) in tetrahydrofuran (100 mL). Warm to ambient temperature. After 18 hours, add dropwise a saturated aqueous ammonium chloride solution (100 mL). Add water (300 mL) and extract with diethyl ether. Dry the organic layer over $MgSO_4$, filter, and evaporate in vacuo to obtain a residue. Chromatograph the residue on silica gel eluting with 10% ethyl acetate/hexane to give a residue. Recrystallize the residue from methanol/water to give (1-(t-butoxycarbonyl)-4-(1-((2-trimethylsilyl)ethoxymethyl)-1H-benzimidazole-2-carbonyl)piperidine.

Add portionwise, (1-(t-butoxycarbonyl)-4-(1-((2-trimethylsilyl)ethoxymethyl)-1H-benzimidazole-2-carbonyl)piperidine (20.0 g, 43.5 mmol) to aqueous hydriodic acid (48%, 140 mL). After the addition is complete, heat to 50° C. After 1.5 hours, cool to ambient temperature. After 2.5 hours, extract twice with diethyl ether. Add diethyl ether (300 mL) and isopropanol (60 mL) to the aqueous layer to give a solid. Collect the solid by filtration and rinse with diethyl ether to give, after drying, the title compound. Elemental Analysis calculated for $C_{13}H_{15}N_3O \cdot 2$ HI: C 32.19; H 3.53; N 8.66; Found: C 32.34; H 3.37; N 8.48.

PREPARATION 2

Synthesis of 1-(t-butoxycarbonyl)-4-(1H-benzimidazole-2-carbonyl)piperidine

Combine 4-(1H-benzimidazole-2-carbonyl)piperidine hydriodic acid salt (9.17 g, 18.9 mmol) and t-butanol (100 mL). Add an aqueous solution of sodium bicarbonate (40 mL, 1 M, 40 mmol). Add di-t-butyldicarbonate (5.2 g, 23.9 mmol). After 72 hours, concentrate in vacuo to give a residue. Combine the residue and ethyl acetate. Extract with aqueous 1 M hydrochloric acid solution, saturated aqueous sodium bicarbonate solution, 0.5 M aqueous sodium thiosulfate solution, and brine. Dry the separated organic layer over $Na_2SO_4$, filter, and evaporate in vacuo to give a solid. Triturate the solid with diethyl ether, collect the solid by filtration, and recrystallize from ethyl acetate to give, after collection and drying, the title compound: mp; 226–228° C. $R_f$=0.30 (silica gel, 20% ethyl acetate/hexane).

PREPARATION 3

Synthesis of 4-(1-(pyrid-2-ylmethyl)-1H-benzimidazole-2-carbonyl)piperidine hydriodic acid salt Combine 1-(t-butoxycarbonyl)-4-(1H-benzimidazole-2-carbonyl)piperidine (2.0 g, 6.1 mmol) and 2-(chloromethyl)pyridine (2.32 g, 18.2 mmol) (obtained by combining 2-(chloromethyl)pyridine hydrochloride, sodium carbonate, and dichloromethane with stirring followed by filtration and evaporation) and potassium carbonate (4.2 g, 30.4 mmol) in acetone (40 mL) and water (10 mL). Heat to reflux. After 24 hours, cool to ambient temperature and dilute with ethyl acetate. Extract with water and brine. Dry the organic layer over $MgSO_4$, filter, and concentrate in vacuo to give a residue. Chromatograph the residue on silica gel eluting with 50% ethyl acetate/hexane to give, after drying, 1-(t-butoxycarbonyl)-4-(1-(pyrid-2-ylmethyl)-1H-benzimidazole-2-carbonyl)piperidine: mp; 45–50° C. $R_f$=0.24 (silica gel, 40% ethyl acetate/hexane). Elemental Analysis calculated for $C_{24}H_{28}N_4O_3$: C 68.08; H 6.74; N 13.23; Found: C 67.88; H 6.68; N 13.00.

Combine 1-(t-butoxycarbonyl)-4-(1-(pyrid-2-ylmethyl)-1H-benzimidazole-2-carbonyl)piperidine (1.96 g, 4.7 mmol) and dichloromethane (150 mL). Cool to 0° C. using an ice bath. Add hydriodic acid (gas) until the solution is saturated and stir. After 30 minutes, again add hydriodic acid (gas) until the solution is saturated. After 2 hours, evaporate in vacuo to give, after drying, the title compound: mp 165–167° C.

PREPARATION 4

Synthesis of 1-(t-butyldimethylsilyloxy)-2-bromoethane

Combine imidazole (59.9 g, 880 mmol), t-butyldimethylsilyl chloride (60.3 g, 400 mmol), and dimethylformamide (300 mL). Cool to 0° C. in a salt-ice bath. Add dropwise 2-bromoethanol (50.0 g, 400 mmol) at such a rate that the temperature of the reaction mixture does not rise above 0° C. After 2 hours, warm to ambient temperature. After 18 hours, extract the reaction mixture three times with hexane. Combine the hexane layers and extract three times with a saturated aqueous solution of ammonium chloride, three times with a saturated aqueous solution of sodium bicarbonate, and then brine. Dry the organic layer over $Na_2SO_4$, filter, and evaporate in vacuo to give the title compound.

PREPARATION 5

Synthesis of 1-(t-butyldimethylsilyloxy)-2-iodoethane

Prepare by the method of Preparation 4 using 2-iodoethanol to give the title compound.

EXAMPLE 1

N-Methyl-N-(4-(4-(1-(pyrid-2-ylmethyl)-1H-benzimidazole-2-carbonyl)piperidin-1-yl)-2-(4-fluorophenyl)butyl)-3,4,5-trimethoxybenzamide

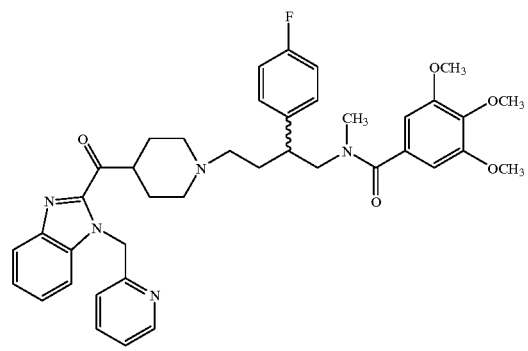

1.1.1 Synthesis of 2-(4-fluorophenyl)-4-(t-butyldimethylsilyloxy)butyronitrile

As adapted from the procedure of *Org. Syn. Collective Volume VI*, 897–900 (1988), combine 4-fluorophenylacetonitrile (56.5 g, 418 mmol), an aqueous 50% sodium hydroxide solution (106.3 g, 1330 mmol), and benzyltriethylammonium chloride (0.95 g) in water (100 mL). Warm to about 30° C. and stir vigorously. Add dropwise over about 30 minutes 1-(t-butyldimethylsilyloxy)-2-bromoethane (50 g, 209 mmol). When the addition is complete, warm to about 40° C. and continue to stir vigorously. After 18 hours, dilute the reaction mixture with ethyl acetate and stir. After 30 minutes, separate the organic layer and extract three times with aqueous saturated ammonium chloride solution, two times with an aqueous saturated sodium bicarbonate solution, and then brine. Dry the organic layer over $Na_2SO_4$, filter, and concentrate in vacuo to give a residue. Distill the residue to give the title compound: bp; 100–115° C. at 0.2 mm Hg. $R_f$=0.35 (silica gel, 1/1 dichloromethane/hexane).

1.1.2 Synthesis of 2-(4-fluorophenyl)-4-(t-butyldimethylsilyloxy)butyronitrile

Combine 4-fluorophenylacetonitrile (5.0 g, 37.0 mmol), and tetrahydrofuran (45 mL). Cool to about −65° C. using a dry-ice/acetone bath. Add a solution of potassium bis-(trimethylsilyl)amide (89 mL, 0.5 M in toluene, 44.5 mmol). After 1 hour, add a solution of 1-(t-butyldimethylsilyloxy)-2-iodoethane (12.7 g, 44.4 mmol) in tetrahydrofuran (10 mL). After the addition of 1-(t-butyldimethylsilyloxy)-2-iodoethane is complete, warm to ambient temperature. After 18 hours, dilute the reaction mixture with tetrahydrofuran and extract three times with aqueous saturated ammonium chloride solution and then twice with brine. Dry the organic layer over $Na_2SO_4$, filter, and concentrate in vacuo to give a residue. Chromatograph the residue on silica gel eluting with 1/1 dichloromethane/hexane to give the title compound.

1.1.3 Synthesis of 2-(4-fluorophenyl)-4-(t-butyldimethylsilyloxy)butyronitrile

Combine 4-fluorophenylacetonitrile (1.0 g, 7.4 mmol), and tetrahydrofuran (9 mL). Cool to about −70° C. using a dry-ice/acetone bath. Add a solution of potassium bis-(trimethylsilyl)amide (14.8 mL, 0.5 M in toluene, 7.4 mmol). After 2 hours, add, via cannula, the solution prepared above to a cooled (−25° C.) solution of 1-(t-butyldimethylsilyloxy)-2-iodoethane (2.1 g, 7.4 mmol) in tetrahydrofuran (4 mL). After the addition to 1-(t-butyldimethylsilyloxy)-2-iodoethane is complete, warm to ambient temperature. After 18 hours, dilute the reaction mixture with tetrahydrofuran and extract three times with aqueous saturated ammonium chloride solution and then twice with brine. Dry the organic layer over $Na_2SO_4$, filter, and concentrate in vacuo to give a residue. Chromatograph the residue on silica gel eluting with 1/1 dichloromethane/hexane to give the title compound.

1.1.4 Synthesis of 2-(4-fluorophenyl)-4-(t-butyldimethylsilyloxy)butyronitrile

Combine 4-fluorophenylacetonitrile (1.0 g, 7.4 mmol), and tetrahydrofuran (20 mL). Cool to about −70° C. using a dry-ice/acetone bath. Add a solution of s-butyl lithium (6.3 mL, 1.3 M in cyclohexane, 8.1 mmol). After 1 hour, add a solution of 1-(t-butyldimethylsilyloxy)-2-iodoethane (2.1 g, 7.4 mmol) in tetrahydrofuran (4 mL). After 2 hours, warm to ambient temperature. After 18 hours, dilute the reaction mixture with ethyl acetate and extract twice with aqueous saturated ammonium chloride solution and then twice with brine. Dry the organic layer over $Na_2SO_4$, filter, and concentrate in vacuo to give a residue. Chromatograph the residue on silica gel eluting with 1/1 dichloromethane/hexane to give the title compound.

1.2 Synthesis of 2-(4-fluorophenyl)-4-(t-butyldimethylsilyloxy)butylamine

Combine 2-(4-fluorophenyl)-4-(t-butyldimethylsilyloxy)butyronitrile (43.0 g, 146.5 mmol) and ethanol (200 mL) in a Parr bottle. Add Raney nickel (129 g) to the reaction mixture. Add a solution of concentrated ammonium hydroxide (40 mL). Hydrogenate on a Parr shaker at 50 psi. After 24 hours, filter through a celite pad and rinse the solids with ethanol. Concentrate the filtrate in vacuo to give the title compound.

1.3 Synthesis of N-(2-(4-fluorophenyl)-4-(t-butyldimethylsilyloxy)butyl)-3,4,5-trimethoxybenzamide Combine 2-(4-fluorophenyl)-4-(t-butyldimethylsilyloxy) butylamine (7.33 g, 24.6 mmol) and sodium carbonate (2.61 g, 24.6 mmol) in 4/1 ethyl acetate/water (400 mL). Cool the reaction mixture to 0° C. with a salt-ice bath. Slowly, add a solution of 3,4,5-trimethoxybenzoyl chloride (5.96, 25.9 mmol) in ethyl acetate (50 mL) at such a rate that the temperature of the reaction mixture does not rise above 5° C. After 2 hours, warm to ambient temperature. After 18 hours, separate the layers and extract the organic layer twice with a saturated aqueous solution of ammonium chloride, twice with a saturated aqueous solution of sodium bicarbonate and then with brine. Dry the organic layer over $Na_2SO_4$, filter, and concentrate in vacuo to obtain a residue. Chromatograph the residue on silica gel eluting with 50% ethyl acetate/hexane to give, after drying, the title compound: mp; 113–114° C. $R_f$=0.30 (silica gel, 50% ethyl acetate/hexane). Elemental Analysis calculated for $C_{26}H_{38}FNO_3Si$: C 63.51; H 7.79; N 2.85; Found: C 63.43; H 7.51; N 2.66.

1.4 Synthesis of N-methyl-N-(2-(4-fluorophenyl)-4-(t-butyldimethylsilyloxy)butyl)-3,4,5-trimethoxybenzamide Combine hexane washed sodium hydride (0.48 g, 50% in oil, 10.0 mmol) and dimethylformamide (5 mL). Cool the reaction mixture to 0° C. with a salt-ice bath. Slowly, add a solution of N-(2-(4-fluorophenyl)-4-(t-butyldimethylsilyloxy)butyl)-3,4,5-trimethoxybenzamide (4.0 g, 8.1 mmol) in dimethylformamide (10 mL). Stir until gas evolution ceases. Add iodomethane (0.62 mL, 10.0 mmol). After 16 hours, dilute the reaction mixture with ethyl acetate and extract three times with water and then brine. Dry the organic layer over $Na_2SO_4$, filter, and concentrate in vacuo to give a residue. Chromatograph the residue on silica gel eluting with 1/1 ethyl acetate/hexane to give, after drying, the title compound: $R_f$=0.15 (silica gel, 1/1 ethyl acetate/hexane). Elemental Analysis calculated for $C_{27}H_{40}FNO_3Si$: C 64.13; H 7.97; N 2.77; Found: C 63.73; H 7.90; N 2.88.

1.5 Synthesis of N-methyl-N-(2-(4-fluorophenyl)-4-hydroxbutyl)-3,4,5-trimethoxybenzamide Combine N-methyl-N-(2-(4-fluorophenyl)-4-(t-butyldimethylsilyloxy)butyl)-3,4,5-trimethoxybenzamide (3.9 g, 7.65 mmol) and methanol (40 mL). Add ammonium fluoride (1.71 g, 46.0 mmol). Heat to reflux. After 20 hours, concentrate in vacuo to give a residue. Combine the residue with water and dichloromethane. Separate the layers and extract the aqueous layer twice with dichloromethane. Combine the organic layers and dry over $Na_2SO_4$, filter, and concentrate in vacuo to give the title compound: mp; 30–35° C. $R_f$=0.30 (silica gel, 10/1 ethyl acetate/methanol).

1.6 Synthesis of N-methyl-N-(2-(4-fluorophenyl)-4-methanesulfonylbutyl)-3,4,5-trimethoxybenzamide Combine N-methyl-N-(2-(4-fluorophenyl)-4-hydroxybutyl)-3,4,5-trimethoxybenzamide (2.5 g, 6.36 mmol), diisopropylethylamine (2.4 mL, 14.0 mmol), and anhydrous dichloromethane (25 mL). Cool the reaction mixture to 0° C. with an ice bath. Slowly, add methanesulfonyl chloride (0.69 mL, 8.9 mmol). After 1 hour, dilute the reaction mixture with dichloromethane and extract 3 times with aqueous 1M hydrochloric acid solution, 2 times with a saturated solution of sodium bicarbonate, and then brine. Dry the organic layer over Na$_2$SO$_4$, filter, and concentrate in vacuo to obtain the title compound: R$_f$=0.43 (silica gel, 10/1 ethyl acetate/methanol).

1.7 Synthesis of N-methyl-N-(4-(4-(1-(pyrid-2-ylmethyl)-1H-benzimidazole-2-carbonyl)piperidin-1-yl)-2-(4-fluorophenyl)butyl)-3,4,5-trimethoxybenzamide Combine N-methyl-N-(2-(4-fluorophenyl)-4-methanesulfonylbutyl)-3,4,5-trimethoxybenzamide (0.37 g, 0.79 mmol), diisopropylethylamine (1.23 mL, 7.1 mmol), and 4-(1-(pyrid-2-ylmethyl)-1H-benzimidazole-2-carbonyl)piperidine hydriodic acid salt (0.83 g, 1.2 mmol) in acetonitrile (15 mL). Heat to reflux. After 18 hours, cool the reaction mixture, dilute with ethyl acetate, and extract with a saturated solution of sodium bicarbonate and then brine. Dry the organic layer over Na$_2$SO$_4$, filter, and concentrate in vacuo to obtain a residue. Chromatograph the residue on silica gel eluting with 10/0.3/89.7 methanol/aqueous concentrated ammonia solution/dichloromethane to give, after drying, the title compound.

PREPARATION 6

Synthesis of 1-(tetrahydropyran-2-yloxy)-2-bromoethane

Combine 2-bromoethanol (14.2 mL, 200 mmol) and dihydropyrane (18.25 mL, 200 mmol) in dichloromethane (20 mL). Add Pyridinium p-toluenesulfonic acid (5 g, 20 mmol). After 2.5 hours, dilute the reaction mixture with diethyl ether and extract with water, 1/1 water/brine, water, and then brine. Dry the organic layer over MgSO$_4$, filter, and evaporate in vacuo to give a residue. Distill the residue to give the title compound: bp; 80–90° C. at 15–20 mm Hg.

PREPARATION A

Synthesis of 4-(1-(4-Fluoro-benzyl)-1H-benzoimidazole-2-carbonyl)-piperidine trifluoroacetic acid salt Combine 1-(t-butoxycarbonyl)-4-(1H-benzoimidazole-2-carbonyl)-piperidine (1.50 g, 4.57 mmol), 4-fluorobenzyl alcohol (0.50 mL, 4.58 mmol) and triphenylphosphine (1.44 g, 5.50 mmol) in tetrahydrofuran (15 mL). Add diethylazodicarboxylate (0.87 mL, 5.50 mmol) dropwise at room temperature. After 23 hours, evaporate the reaction mixture in vacuo to give a residue. Chromatograph the residue on silica gel eluting with 25% ethyl acetate/hexane to give 1-(t-butoxycarbonyl)-4-(1-(4-fluoro-benzyl)-1H-benzoimidazole-2-carbonyl)-piperidine.

Cool the 1-(t-butoxycarbonyl)-4-(1-(4-fluoro-benzyl)-1H-benzoimidazole-2-carbonyl)-piperidine in an ice bath. Add trifluoroacetic acid and mix. After 15 minutes, add diethyl ether to give a residue. Collect the residue by filtration and dry under vacuum. Recrystallize from ethanol/ether and dry resulting solid under vacuum to give the title compound.

EXAMPLE 2

N-Methyl-N-(4-(4-(1-(4-fluorobenzyl)-1H-benzimidazole-2-carbonyl)piperidin-1-yl)-2-(3,4-dichlorophenyl)butyl)benzamide

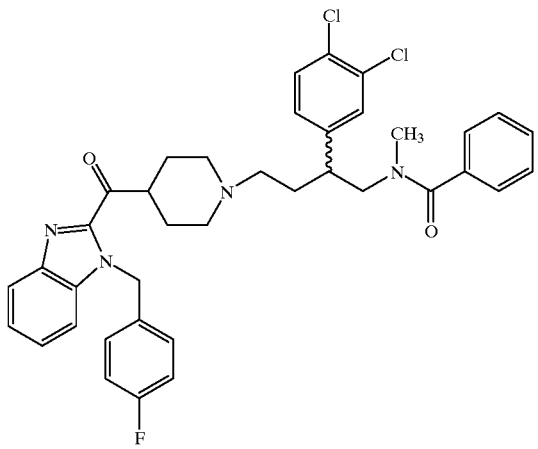

2.1 Synthesis of 2-(3,4-dichlorophenyl)-4-(tetrahydropyran-2-yloxy)butyronitrile Combine sodium hydride (1.2 g, 50 mmol) and tetrahydrofuran (20 mL). Add dropwise a solution of 3,4-dichlorophenylacetonitrile (8.9 g, 47.8 mmol) in tetrahydrofuran (50 mL) at about 0° C. When the addition is complete, allow to warm to ambient temperature and stir. After 2.5 hours, cool to 0° C. and add 1-(tetrahydropyran-2-yloxy)-2-bromoethane (10.0 g, 47.9 mmol). Warm to ambient temperature. After 16 hours, pour the reaction mixture into saturated ammonium chloride and extract with diethyl ether. Separate the organic layer and extract with water and brine. Dry the organic layer over MgSO$_4$, filter, and concentrate in vacuo to give a residue. Chromatograph the residue on silica gel eluting sequentially with 5% ethyl acetate/hexane, 10% ethyl acetate/hexane, and 20% ethyl acetate in hexane to give the title compound.

2.2 Synthesis of 2-(3,4-dichlorophenyl)-4-(tetrahydropyran-2-yloxy)butylamine

Combine 2-(3,4-dichlorophenyl)-4-(tetrahydropyran-2-yloxy)butyronitrile (7 g) and ethanol (20 mL) in a Parr bottle. Add Raney nickel (1 g) to the reaction mixture. Add a solution of concentrated ammonium hydroxide (3.5 mL). Hydrogenate on a Parr shaker at 50 psi. After 24 hours, filter through a celite pad and rinse the solids with ethanol. Concentrate the filtrate in vacuo to obtain a residue. Chromatograph the residue in vacuo on silica gel eluting sequentially with 50% ethyl acetate/hexane and 10% methanol/dichloromethane to give the title compound.

2.3 Synthesis of N-(2-(3,4-dichlorophenyl)-4-(tetrahydropyran-2-yloxy)butyl)benzamide Combine 2-(3,4-dichlorophenyl)-4-(tetrahydropyran-2-yloxy)butylamine (3.05 g, 9.6 mmol) and N-methylmorpholine (2.2 mL, 20 mmol) in anhydrous dichloromethane (25 mL). Cool the reaction mixture to 0° C. with a salt-ice bath. Slowly, add benzoyl chloride (1.2 mL, 10.3 mmol). After 1 hour, extract the reaction mixture with a saturated solution of sodium bicarbonate and then water. Dry the organic layer over MgSO$_4$, filter, and concentrate in vacuo to obtain a residue. Chromatograph the residue on silica gel eluting sequentially with 35% ethyl acetate/hexane and then with 50% ethyl acetate/hexane to give the title compound.

2.4 Synthesis of N-methyl-N-(2-(3,4-dichlorophenyl)-4-(tetrahydropyran-2-yloxy)butyl)benzamide Combine N-(2-(3,4-dichlorophenyl)-4-(tetrahydropyran-2-yloxy)butyl)benzamide (3.84 g) and tetrahydrofuran (20 mL). Add sodium hydride (0.28 g, 11.5 mmol) and stir until gas evolution ceases. Add iodomethane (1.5 mL, 24.1 mmol). After 6 hours, dilute the reaction mixture with diethyl ether and extract with a saturated solution of ammonium chloride. Separate the organic layer and extract with sodium bisulfite solution, water, and brine. Dry the organic layer over MgSO$_4$, filter, and concentrate in vacuo to give the title compound.

2.5 Synthesis of N-methyl-N-(2-(3,4-dichlorophenyl)-4-hydroxybutyl)benzamide

Combine N-methyl-N-(2-(3,4-dichlorophenyl)-4-(tetrahydropyran-2-yloxy)butyl)benzamide (3.7 g) and methanol (30 mL). Add p-toluenesulfonic acid hydrate (0.73 g) and stir. After 18 hours, concentrate in vacuo to give a residue. Combine the residue and dichloromethane and extract with a saturated solution of sodium bicarbonate and then water. Dry the organic layer over MgSO$_4$, filter, and concentrate in vacuo to obtain a residue. Chromatograph the residue on silica gel eluting sequentially with 50% ethyl acetate/hexane and then ethyl acetate to give the title compound.

2.6 Synthesis of N-methyl-N-(2-(3,4-dichlorophenyl)-4-methanesulfonylbutyl)benzamide Combine N-methyl-N-(2-(3,4-dichlorophenyl)-4-hydroxybutyl)benzamide (0.5 g), diisopropylethylamine (0.3 mL, 1.7 mmol), and anhydrous dichloromethane (8 mL). Cool the reaction mixture to 0° C. with an ice bath. Slowly, add methanesulfonyl chloride (0.13 mL, 1.7 mmol). Warm to ambient temperature. After 18 hours, quench the reaction by the addition of ice. Separate the organic layer and extract 3 times with 1M hydrochloric acid solution and 2 times with a saturated solution of sodium bicarbonate. Dry the organic layer over Na$_2$SO$_4$, filter, and concentrate in vacuo to obtain the title compound.

2.7 Synthesis of N-methyl-N-(4-(4-(1-(4-fluorobenzyl)-1H-benzimidazole-2-carbonyl)piperidin-1-yl)-2-(3,4-dichlorophenyl)butyl)benzamide Combine N-methyl-N-(2-(3,4-dichlorophenyl)-4-methanesulfonylbutyl)benzamide (0.6 g, 1.4 mmol), sodium bicarbonate (0.23 g, 2.8 mmol), and 4-(1-(4-fluorobenzyl)-1H-benzimidazole-2-carbonyl)piperidine trifluoroacetic acid salt (0.63 g, 1.4 mmol) in tetrahydrofuran (15 mL) and water (5 mL). Heat to reflux. After 3 days, cool the reaction mixture, dilute with ethyl acetate, and extract with water and then brine. Dry the organic layer over MgSO$_4$, filter, and concentrate in vacuo to obtain a residue. Chromatograph the residue on silica gel eluting with sequentially with 10% toluene/ethyl acetate and then 10% ethanol/10%toluene/ethyl acetate to give, after drying, the title compound: mp: 65–70° C.

2.8 Synthesis of N-methyl-N-(4-(4-(1-(4-fluorobenzyl)-1H-benzimidazole-2-carbonyl)piperidin-1-yl)-2-(3,4-dichlorophenyl)butyl)benzamide hydrochloride salt Combine N-methyl-N-(4-(4-(1-(4-fluorobenzyl)-1H-benzimidazole-2-carbonyl)piperidin-1-yl)-2-(3,4-dichlorophenyl)butyl)benzamide (0.71 g, 1.4 mmol) and methanol (10 mL). Add a saturated solution of hydrochloric acid in diethyl ether (3 mL). Evaporate in vacuo to obtain a residue. Combine the residue and butanone (5 mL) and slowly add diethyl ether to give a solid. Collect the solid and dry to give the title compound.

EXAMPLE 3

N-Methyl-N-(4-(4-(1-(4-fluorobenzyl)-1H-benzoimidazol-2-yl)-4-hydroxypiperidin-1-yl)-2-(4-methoxyphenyl)butyl)benzamide

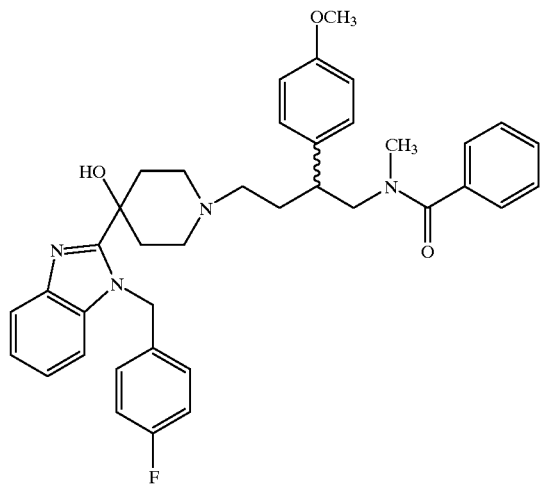

3.1 Synthesis of 2-(4-methoxyphenyl)-4-(t-butyldimethylsilyloxy)butyronitrile

Prepare by the method of Example 1.1.1 using 4-methoxyphenylacetonitrile and 1-(t-butyldimethylsilyloxy)-2-bromoethane to give the title compound.

3.2 Synthesis of 2-(4-methoxyphenyl)-4-(t-butyldimethylsilyloxy)butylamine

Prepare by the method of Example 1.2 using 2-(4-methoxyphenyl)-4-(t-butyldimethylsilyloxy)butyronitrile to give the title compound.

3.3 Synthesis of N-(2-(4-methoxyphenyl)-4-(t-butyldimethylsilyloxy)butyl)benzamide Prepare by the method of Example 1.3 using 2-(4-methoxyphenyl)-4-(t-butyldimethylsilyloxy)butylamine and benzoyl chloride to give the title compound.

3.4 Synthesis of N-methyl-N-(2-(4-methoxyohenyl)-4-(t-butyldimethylsilyloxy)butyl)benzamide Prepare by the method of Example 1.4 using N-(2-(4-methoxyphenyl)-4-(t-butyldimethylsilyloxy)butyl)benzamide to give the title compound.

3.5 Synthesis of N-methyl-N-(2-(4-methoxyphenyl)-4-hydroxybutyl)benzamide

Prepare by the method of Example 1.5 using N-methyl-N-(2-(4-methoxyphenyl)-4-(t-butyldimethylsilyloxy)butyl)benzamide to give the title compound.

3.6 Synthesis of N-methyl-N-(2-(4-methoxyphenyl)-4-methanesulfonylbutyl)benzamide Prepare by the method of Example 1.6 using N-methyl-N-(2-(4-methoxyphenyl)-4-hydroxybutyl)benzamide and methanesulfonyl chloride to give the title compound.

3.7 Synthesis of N-methyl-N-(4-(4-(1-(4-fluorobenzyl)-1H-benzoimidazol-2-yl)-4-hydroxypipridin-1-yl)-2-(4-ethoxyphenyl)butyl)benzamide Prepare by the method of Example 1.7 using N-methyl-N-(2-(4-methoxyphenyl)-4-methanesulfonylbutyl)benzamide and 4-(1-(4-fluorobenzyl)-1H-benzoimidazol-2-yl)-4-hydroxy-piperidine to give the title compound.

PREPARATION 7

Synthesis of 4-(1-(2-(5-hydroxymethylfur-2-ylmethyl)-4-(1H-benzimidazole-2-carbonyl) piperidine According to the method of P. G. McDougal, et al., *J. Org. Chem.*, 51, 3388–3390 (1986), combine hexane washed sodium hydride (20 mmol) and tetrahydrofuran (40 mL). Slowly add 2,5-furandimethanol (20 mmol). After gas evolution ceases, add t-butyldimethylsilyl chloride (20 mmol) and stir vigorously. After about 1 hour, pour the reaction mixture into diethyl ether and extract with a saturated aqueous solution of sodium carbonate, water, and then brine. Dry the organic layer over Na$_2$SO$_4$, filter, and evaporate in vacuo to give 5-(t-butyldimethylsilyloxy)methyl-2-hydroxymethylfuran. Combine 1-(t-butoxycarbonyl)-4-(1H-benzimidazole-2-carbonyl)piperidine (10 mmol), 5-(t-butyldimethylsilyloxy)-methyl-2-hydroxymethylfuran (10 mmol), and triphenylphosphine (10 mmol) in tetrahydrofuran (100 mL). Add diethyl azodicarboxylate (10 mmol). After 18 hours, evaporate the reaction mixture in vacuo to give a residue. Partition the residue between ethyl acetate and water. Separate the organic layer and extract with water and brine. Dry the organic layer over Na$_2$SO$_4$, filter, and evaporate in vacuo to give a residue. Chromatograph the residue on silica gel to give 1-(t-butoxycarbonyl)-4-(1-(5-(t-butyldimethylsilyloxy)-methylfur-2-ylmethyl)-1H-benzimidazole-2-carbonyl)piperidine.

Combine 1-(t-butoxycarbonyl)-4-(1-(5-(t-butyldimethylsilyloxy)methylfur-2-ylmethyl)-1H-benzimidazole-2-carbonyl)piperidine (7 mmol) and methanol (40 mL). Add ammonium fluoride (42 mmol). Heat to reflux. After 20 hours, concentrate in vacuo to give a residue. Combine the residue with water and dichloromethane. Separate the layers and extract the aqueous layer twice with dichloromethane. Combine the organic layers and dry over Na$_2$SO$_4$, filter, and concentrate in vacuo to give 1-(t-butoxycarbonyl)-4-(1-(5-hydroxymethylfur-2-ylmethyl)-1H-benzimidazole-2-carbonyl)piperidine.

Combine 1-(t-butoxycarbonyl)-4-(1-(5-hydroxymethylfur-2-ylmethyl)-1H-benzimidazole-2-carbonyl)piperidine (5 mmol) and dioxane (25 mL). Slowly add a solution of hydrochloric acid in dioxane (1.25 mL, 4 M, 5 mmol). After 45 minutes, add diethyl ether and evaporate in vacuo to give a residue. Partition the residue between dichloromethane and saturated aqueous sodium bicarbonate solution. Separate the organic layer and extract with brine. Dry the organic layer over Na$_2$SO$_4$, filter, and evaporate in vacuo to give the title compound.

EXAMPLE 4

N-Methyl-N-(4-(4-(1-(5-hydroxymethylfur-2-ylmethyl)-1H-benzimidazole)-4-hydroxypiperidin-1-yl)-2-phenylbutyl)benzamide

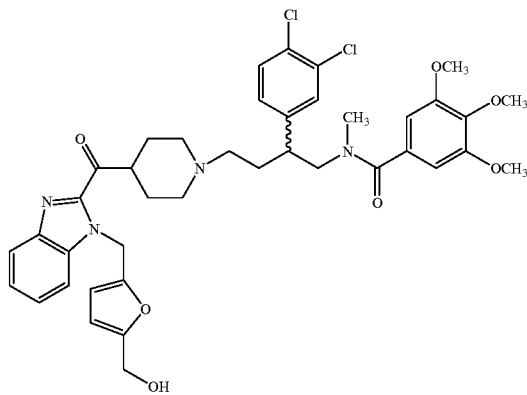

4.1 Synthesis of N-methyl-N-(4-(4-(1-(5-hydroxymethylfur-2-ylmethyl)-1H-benzimidazole)-4-hydroxypiperidin-1-yl)-2-phenylbutyl)benzamide Prepare by the method of Example 1.7 using N-methyl-N-(2-(3,4-dichlorophenyl)-4-methanesulfonylbutyl)-3,4,5-trimethoxybenzamide and 4-(1-(5-hydroxymethylfur-2-ylmethyl)-1H-benzimidazole-2-carbonyl)piperidine to give the title compound.

EXAMPLE 5

N-Methyl-N-(4-(4-(benzthiazole-2-carbonyl)piperidin-1-yl)-2-(3,4-dichlorophenyl)butyl)benzamide

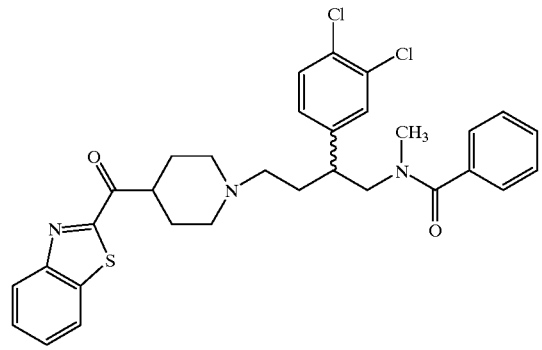

5.1 Synthesis of N-methyl-N-(4-(4-(benzthiazole-2-carbonyl)piperidin-1-yl)-2-(3,4-dichlorophenyl)butyl)benzamide Prepare by the method of Example 2.7 using N-methyl-N-(2-(3,4-dichlorophenyl)-4-methanesulfonylbutyl)benzamide and 4-(benzthiazole-2-carbonyl)piperidine to give the title compound.

EXAMPLE 6

N-Methyl-N-(4-(4-(hydroxydiphenylmethyl)piperidin-1-yl)-2-phenylbutyl)benzamide

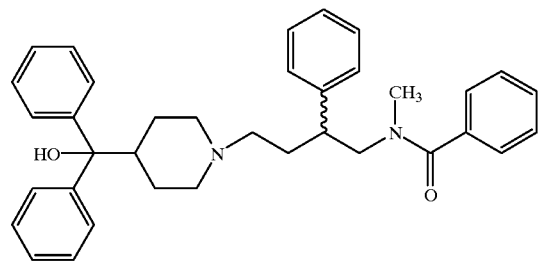

6.1 Synthesis of 2-phenyl-4-(t-butyldimethylsilyloxy)-butyronitrile

Prepare by the method of Example 1.1.1 using phenylacetonitrile and 1-(t-butyldimethylsilyloxy)-2-bromoethane to give of the title compound.

6.2 Synthesis of 2-phenyl-4-(t-butyldimethylsilyloxy)-butylamine

Prepare by the method of Example 1.2 using 2-phenyl-4-(t-butyldimethylsilyloxy)butyronitrile to give the title compound.

6.3 Synthesis of N-(2-phenyl-4-(t-butyldimethylsilyloxy)-butyl)benzamide

Prepare by the method of Example 1.3 using 2-phenyl-4-(t-butyldimethylsilyloxy)butylamine and benzoyl chloride to give the title compound.

6.4 Synthesis of N-methyl-N-(2-phenyl-4-(t-butyldimethylsilyloxy)butyl)benzamide Prepare by the method of Example 1.4 using N-(2-phenyl-4-(t-butyldimethylsilyloxy)butyl)benzamide to give the title compound.

6.5 Synthesis of N-methyl-N-(2-phenyl-4-hydroxybutyl)benzamide

Prepare by the method of Example 1.5 using N-methyl-N-(2-phenyl-4-(t-butyldimethylsilyloxy)butyl)benzamide to give the title compound.

6.6 Synthesis of N-methyl-N-(2-phenyl-4-methanesulfonylbutyl)benzamide

Prepare by the method of Example 1.6 using N-methyl-N-(2-phenyl-4-hydroxybutyl)benzamide and methanesulfonyl chloride to give the title compound.

6.7 Synthesis of N-methyl-N-(4-(4-(hydroxydiphenylmethyl)-piperidin-1-yl)-2-phenylbutyl)benzamide Prepare by the method of Example 1.7 using N-methyl-N-(2-phenyl-4-methanesulfonylbutyl)benzamide and 4-(hydroxydiphenylmethyl)piperidine to give the title compound.

EXAMPLE 7

N-Methyl-N-(4-(4-(1-(4-fluorobenzyl)-1H-benzimidazole-2-carbonyl)piperidin-1-yl)-2-(3,4-dimethoxyphenyl)butyl)benzamide

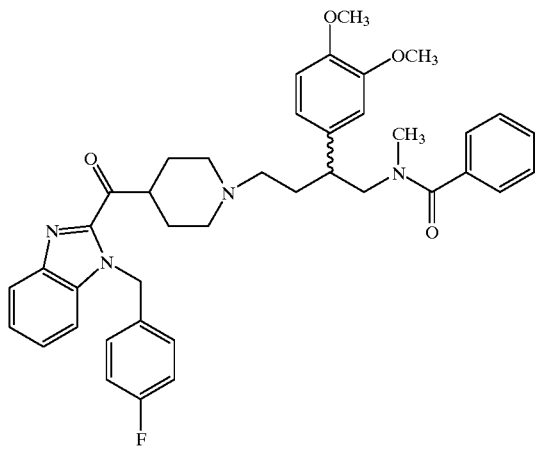

7.1 Synthesis of 2-(3,4-dimethoxyphenyl)-4-(t-butyldimethylsilyloxy)butyronitrile Prepare by the method of Example 1.1.1 using 3,4-dimethoxyphenylacetonitrile and 1-(t-butyldimethylsilyloxy)-2-bromoethane to give of the title compound.

7.2 Synthesis of 2-(3,4-dimethoxyphenyl)-4-(t-butyldimethylsilyloxy)butylamine

Prepare by the method of Example 1.2 using 2-(3,4-dimethoxyphenyl)-4-(t-butyldimethylsilyloxy)butyronitrile to give the title compound.

7.3 Synthesis of N-(2-(3,4-dimethoxyphenyl)-4-(t-butyldimethylsilyloxy)butyl)benzamide Prepare by the method of Example 1.3 using 2-(3,4-dimethoxyphenyl)-4-(t-butyldimethylsilyloxy)butylamine and benzoyl chloride to give the title compound.

7.4 Synthesis of N-methyl-N-(2-(3,4-dimethoxyphenyl)-4-(t-butyldimethylsilyloxy)butyl)benzamide Prepare by the method of Example 1.4 using N-(2-(3,4-dimethoxyphenyl)-4-(t-butyldimethylsilyloxy)butyl)benzamide to give the title compound.

7.5 Synthesis of N-methyl-N-(2-(3,4-dimethoxyphenyl)-4-hydroxybutyl)benzamide

Prepare by the method of Example 1.5 using N-methyl-N-(2-(3,4-dimethoxyphenyl)-4-(t-butyldimethylsilyloxy)butyl)benzamide to give the title compound.

7.6 Synthesis of N-methyl-N-(2-(3,4-dimethoxyphenyl)-4-methanesulfonylbutyl)benzamide Prepare by the method of Example 1.6 using N-methyl-N-(2-(3,4-dimethoxyphenyl)-4-hydroxybutyl)benzamide and methanesulfonyl chloride to give the title compound.

7.7 Synthesis of N-methyl-N-(4-(4-(1-(4-fluorobenzyl)-1H-benzimidazole-2-carbonyl)piperidin-1-yl)-2-(3,4-dimethoxyphenyl)butyl)benzamide Prepare by the method of Example 1.7 using N-methyl-N-(2-(3,4-dimethoxyphenyl)-4-methanesulfonylbutyl)benzamide and 4-(1-(4-fluorobenzyl)-1H-benzimidazole-2-carbonyl)piperidine to give the title compound.

EXAMPLE 8

N-Methyl-N-(4-(4-(1-(4-fluorobenzyl)-1H-benzimidazole-2-carbonyl)piperidin-1-yl)-2-(benzo[1,3]dioxol-5-yl)butyl)benzamide

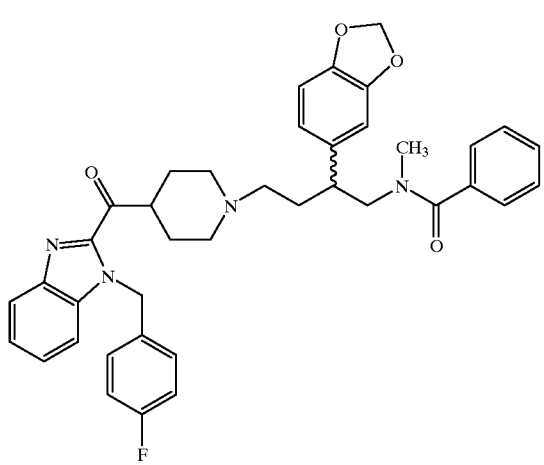

8.1 Synthesis of 2-(benzo[1,3]dioxol-5-yl)-4-(t-butyldimethylsilyloxy)butyronitrile Prepare by the method of Example 1.1.1 using benzo[1,3]dioxol-5-ylacetonitrile and 1-(t-butyldimethylsilyloxy)-2-bromoethane to give of the title compound.

8.2 Synthesis of 2-(benzo[1,3]dioxol-5-yl)-4-(t-butyldimethylsilyloxy)butylamine Prepare by the method of Example 1.2 using 2-(benzo[1,3]dioxol-5-yl)-4-(t-butyldimethylsilyloxy)-butyronitrile to give the title compound.

8.3 Synthesis of N-(2-(benzo[1,3]dioxol-5-yl)-4-(t-butyldimethylsilyloxy)butyl)benzamide Prepare by the method of Example 1.3 using 2-(benzo[1,3]dioxol-5-yl)-4-(t-butyldimethylsilyloxy)butylamine and benzoyl chloride to give the title compound.

8.4 Synthesis of N-methyl-N-(2-(benzo[1,3]dioxol-5-yl)-4-(t-butyldimethylsilyloxy)butyl)benzamide Prepare by the method of Example 1.4 using N-(2-(benzo[1,3]dioxol-5-yl)-4-(t-butyldimethylsilyloxy)butyl)benzamide to give the title compound.

8.5 Synthesis of N-methyl-N-(2-(benzo[1.3]dioxol-5-yl)-4-hydroxybutyl)benzamide

Prepare by the method of Example 1.5 using N-methyl-N-(2-(benzo[1,3]dioxol-5-yl)-4-(t-butyldimethylsilyloxy)butyl)benzamide to give the title compound.

8.6 Synthesis of N-methyl-N-(2-(benzo[1,3]dioxol-5-yl)-4-methanesulfonylbutyl)benzamide Prepare by the method of Example 1.6 using N-methyl-N-(2-(benzo[1,3]dioxol-5-yl)-4-hydroxybutyl)benzamide and methanesulfonyl chloride to give the title compound.

8.7 Synthesis of N-methyl-N-(4-(4-(1-(4-fluorobenzyl)-1H-benzimidazole-2-carbonyl)piperidin-1-yl)-2-(benzo[1,3]dioxol-5-yl)butyl)benzamide Prepare by the method of Example 1.7 using N-methyl-N-(2-(benzo[1,3]dioxol-5-yl)-4-methanesulfonylbutyl)benzamide and 4-(1-(4-fluorobenzyl)-1H-benzimidazole-2-carbonyl)piperidine to give the title compound.

EXAMPLE 9

N-Methyl-N-(4-(4-(1-(4-fluorobenzyl)-1H-benzimidazole-2-carbonyl)piperidin-1-yl)-2-(naphth-2-yl)butyl)benzamide

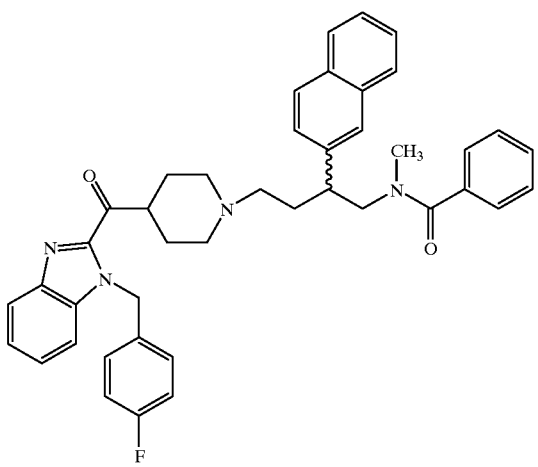

9.1 Synthesis of 2-(naphth-2-yl)-4-(t-butyldimethylsilyloxy)butyronitrile

Prepare by the method of Example 1.1.1 using naphth-2-ylacetonitrile and 1-(t-butyldimethylsilyloxy)-2-bromoethane to give of the title compound.

9.2 Synthesis of 2-(naphth-2-yl)-4-(t-butyldimethylsilyloxy)butylamine

Prepare by the method of Example 1.2 using 2-(naphth-2-yl)-4-(t-butyldimethylsilyloxy)butyronitrile to give the title compound.

9.3 Synthesis of N-(2-(naphth-2-yl)-4-(t-butyldimethylsilyloxy)butyl)benzamide

Prepare by the method of Example 1.3 using 2-(naphth-2-yl)-4-(t-butyldimethylsilyloxy)butylamine and benzoyl chloride to give the title compound.

9.4 Synthesis of N-methyl-N-(2-(naphth-2-yl)-4-(t-butyldimethylsilyloxy)butyl)benzamide Prepare by the method of Example 1.4 using N-(2-(naphth-2-yl)-4-(t-butyldimethylsilyloxy)butyl)benzamide to give the title compound.

9.5 Synthesis of N-methyl-N-(2-(naphth-2-yl)-4-hydroxybutyl)benzamide

Prepare by the method of Example 1.5 using N-methyl-N-(2-(naphth-2-yl)-4-(t-butyldimethylsilyloxy)butyl)benzamide to give the title compound.

9.6 Synthesis of N-methyl-N-(2-(naphth-2-yl)-4-methanesulfonylbutyl)benzamide

Prepare by the method of Example 1.6 using N-methyl-N-(2-(naphth-2-yl)-4-hydroxybutyl)benzamide and methanesulfonyl chloride to give the title compound.

9.7 Synthesis of N-methyl-N-(4-(4-(1-(4-fluorobenzyl)-1H-benzimidazole-2-carbonyl)piperidin-1-yl)-2-(naphth-2-yl)butyl)benzamide Prepare by the method of Example 1.7 using N-methyl-N-(2-(naphth-2-yl)-4-methanesulfonylbutyl)benzamide and 4-(1-(4-fluorobenzyl)-1H-benzimidazole-2-carbonyl)piperidine to give the title compound.

EXAMPLE 10

N-Methyl-N-(4-(4-(1-(4-fluorobenzyl)-1H-benzimidazole-2-carbonyl)piperidin-1-yl)-2-(3,4-dichlorophenyl)butyl)-3,5-bis(trifluoromethyl)benzamide

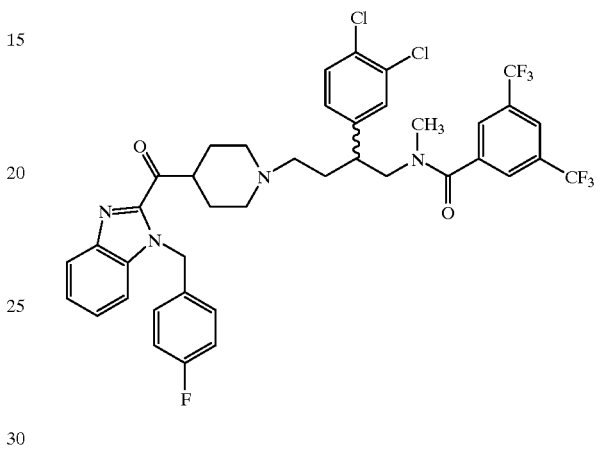

10.1 Synthesis of N-(2-(3,4-dichlorophenyl)-4-(t-butyldimethylsilyloxy)butyl)-3,5-bis(trifluoromethyl)benzamide Prepare by the method of Example 1.3 using 2-(3,4-dichlorophenyl)-4-(t-butyldimethylsilyloxy)butylamine and 3,5-bis(trifluoromethyl)benzoyl chloride to give the title compound.

10.2 Synthesis of N-methyl-N-(2-(3,4-dichlorophenyl)-4-(t-butyldimethylsilyloxy)butyl)-3,5-bis(trifluoromethyl)benzamide Prepare by the method of Example 1.4 using N-(2-(3,4-dichlorophenyl)-4-(t-butyldimethylsilyloxy)butyl)-3,5-bis(trifluoromethyl)benzamide to give the title compound.

10.3 Synthesis of N-methyl-N-(2-(3,4-dichlorophenyl)-4-hydroxybutyl)-3,5-bis(trifluoromethyl)benzamide Prepare by the method of Example 1.5 using N-methyl-N-(2-(3,4-dichlorophenyl)-4-(t-butyldimethylsilyloxy)butyl)-3,5-bis(trifluoromethyl)benzamide to give the title compound.

10.4 Synthesis of N-methyl-N-(2-(3,4-dichlorophenyl)-4-methanesulfonylbutyl)-3,5-bis(trifluoromethyl)benzamide Prepare by the method of Example 1.6 using N-methyl-N-(2-(3,4-dichlorophenyl)-4-hydroxybutyl)-3,5-bis(trifluoromethyl)benzamide and methanesulfonyl chloride to give the title compound.

10.5 Synthesis of N-methyl-N-(4-(4-(1-(4-fluorobenzyl)-1H-benzimidazole-2-carbonyl)piperidin-1-yl)-2-(3,4-dichlorophenyl)butyl)3,5-bis(trifluoromethyl)benzamide Prepare by the method of Example 1.7 using N-methyl-N-(2-(3,4-dichlorophenyl)-4-methanesulfonylbutyl)-3,5-bis(trifluoromethyl)benzamide and 4-(1-(4-fluorobenzyl)-1H-benzimidazole-2-carbonyl)piperidine to give the title compound.

EXAMPLE 11

N-Methyl-N-(4-(4-(1-(pyrid-2-ylmethyl)-1H-benzimidazole-2-carbonyl)piperidin-1-yl)-2-(3-trifluoromethylphenyl)butyl)-3,4,5-trimethoxybenzamide

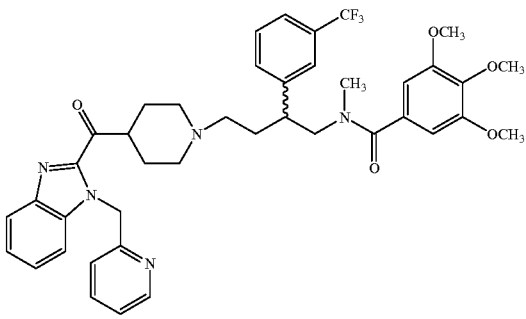

11.1 Synthesis of 2-(3-trifluoromethylphenyl)-4-(t-butyldimethylsilyloxy)butyronitrile Prepare by the method of Example 1.1.1 using 3-trifluoromethylphenylacetonitrile and 1-(t-butyldimethylsilyloxy)-2-bromoethane to give the title compound.

11.2 Synthesis of 2-(3-trifluoromethylphenyl)-4-(t-butyldimethylsilyloxy)butylamine Prepare by the method of Example 1.2 using 2-(3-trifluoromethylphenyl)-4-(t-butyldimethylsilyloxy)butyronitrile to give the title compound.

11.3 Synthesis of N-(2-(3-trifluoromethylphenyl)-4-(t-butyldimethylsilyloxy)butyl)-3,4,5-trimethoxybenzamide Prepare by the method of Example 1.3 using 2-(3-trifluoromethylphenyl)-4-(t-butyldimethylsilyloxy)butylamine and 3,4,5-trimethoxybenzoyl chloride to give the title compound.

11.4 Synthesis of N-methyl-N-(2-(3-trifluoromethylphenyl)-4-(t-butyldimethylsilyloxy)butyl)-3,4,5-trimethoxybenzamide Prepare by the method of Example 1.4 using N-(2-(3-trifluoromethylphenyl)-4-(t-butyldimethylsilyloxy)butyl)-3,4,5-trimethoxybenzamide to give the title compound.

11.5 Synthesis of N-methyl-N-(2-(3-trifluoromethylphenyl)-4-hydroxybutyl)-3,4,5-trimethoxybenzamide Prepare by the method of Example 1.5 using N-methyl-N-(2-(3-trifluoromethylphenyl)-4-(t-butyldimethylsilyloxy)butyl)-3,4,5-trimethoxybenzamide to give the title compound.

11.6 Synthesis of N-methyl-N-(2-(3-trifluoromethylphenyl)-4-methanesulfonylbutyl)-3,4,5-trimethoxybenzamide Prepare by the method of Example 1.6 using N-methyl-N-(2-(3-trifluoromethylphenyl)-4-hydroxybutyl)-3,4,5-trimethoxybenzamide to give the title compound.

11.7 Synthesis of N-methyl-N-(4-(4-(1-(pyrid-2-ylmethyl)-1H-benzimidazole-2-carbonyl)piperidin-1-yl)-2-(3-trifluoromethylphenyl)butyl)-3,4,5-trimethoxybenzamide Prepare by the method of Example 1.7 using N-methyl-N-(2-(3-trifluoromethylphenyl)-4-methanesulfonylbutyl)-3,4,5-trimethoxybenzamide and 4-(1-(pyrid-2-ylmethyl)-1H-benzimidazole-2-carbonyl)piperidine hydriodic acid salt to give the title compound.

EXAMPLE 12

N-Methyl-N-(4-(4-(1-(4-fluorobenzyl)-1H-benzimidazole-2-carbonyl)piperidin-1-yl)-2-(thien-2-yl)butyl)-3,4,5-trimethoxybenzamide

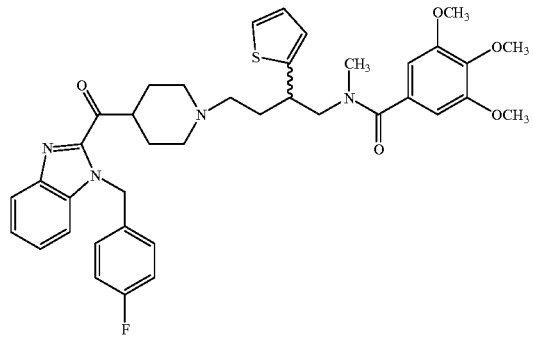

12.1 Synthesis of 2-(thien-2-yl)-4-(t-butyldimethylsilyloxy)butyronitrile

Prepare by the method of Example 1.1.1 using thien-2-ylacetonitrile and 1-(t-butyldimethylsilyloxy)-2-bromoethane to give of the title compound.

12.2 Synthesis of 2-(thien-2-yl)-4-(t-butyldimethylsilyloxy)butylamine

Combine 2-(thien-2-yl)-4-(t-butyldimethylsilyloxy)butyronitrile (3.24 mmol) and cobalt(II)chloride hexahydrate (1.54 g, 6.48 mmol) in methanol (50 mL). While maintaining the temperature at or below 20° C. with an ice-bath, add portionwise sodium borohydride (2.17 g, 57 mmol). After the addition is complete, allow the reaction mixture to stand at ambient temperature for 18 hours. Evaporate the reaction mixture in vacuo to obtain a residue. Partition the residue between dichloromethane and a saturated aqueous solution of ammonium chloride. Adjust the pH of the aqueous layer to about 8 using a 1 M aqueous solution of hydrochloric acid. Separate the layers and extract the aqueous layer several times with dichloromethane, combine the organic layers, dry over $Na_2SO_4$, filter, and concentrate invacuo to give the title compound.

12.3 Synthesis of N-(2-(thien-2-yl)-4-(t-butyldimethylsilyloxyy)butyl)-3,4,5-trimethoxybenzamide Prepare by the method of Example 1.3 using 2-(thien-2-yl)-4-(t-butyldimethylsilyloxy)butylamine and 3,4,5-trimethoxybenzoyl chloride to give the title compound.

12.4 Synthesis of N-methyl-N-(2-(thien-2-yl)-4-(t-butyldimethylsilyloxy)butyl)-3,4,5-trimethoxybenzamide Prepare by the method of Example 1.4 using N-(2-(thien-2-yl)-4-(t-butyldimethylsilyloxy)butyl)-3,4,5-trimethoxybenzamide to give the title compound.

12.5 Synthesis of N-methyl-N-(2-(thien-2-yl)-4-hydroxybutyl)-3,4,5-trimethoxybenzamide Prepare by the method of Example 1.5 using N-methyl-N-(2-(thien-2-yl)-4-(t-butyldimethylsilyloxy)butyl)-3,4,5-trimethoxybenzamide to give the title compound.

12.6 Synthesis of N-methyl-N-(2-(thien-2-yl)-4-methanesulfonylbutyl)-3,4,5-trimethoxybenzamide Prepare by the method of Example 1.6 using N-methyl-N-(2-(thien-2-yl)-4-hydroxybutyl)-3,4,5-trimethoxybenzamide and methanesulfonyl chloride to give the title compound.

12.7 Synthesis of N-methyl-N-(4-(4-(1-(4-fluorobenzyl)-1H-benzimidazole-2-carbonyl)piperidin-1-yl)-2-(thien-2-yl)butyl)-3,4,5-trimethoxybenzamide Prepare by the method of Example 1.7 using N-methyl-N-(2-(thien-2-yl)-4-methanesulfonylbutyl)-3,4,5- trimethoxybenzamide and 4-(1-(4-fluorobenzyl)-1H-benzimidazole-2-carbonyl)piperidine to give the title compound.

EXAMPLE 13

N-Methyl-N-(4-(4-(1-(4-fluorobenzyl)-1H-benzimidazole-2-carbonyl)piperidin-1-yl)-2-(pyrid-3-yl)butyl)-3,4,5-trimethoxybenzamide

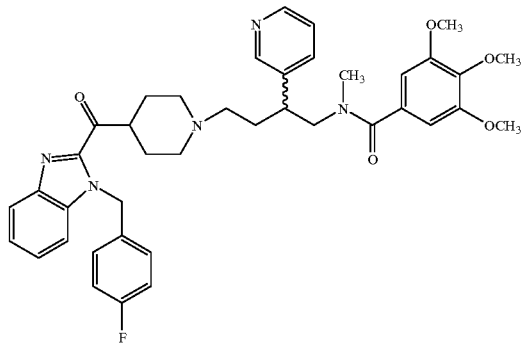

13.1 Synthesis of 2-(pyrid-3-yl)-4-(t-butyldimethylsilyloxy)butyronitrile

Prepare by the method of Example 1.1.2 using pyrid-3-ylacetonitrile and 1-(t-butyldimethylsilyloxy)-2-bromoethane to give of the title compound.

13.2 Synthesis of 2-(pyrid-3-yl)-4-(t-butyldimethylsilyloxy)butylamine

Prepare by the method of Example 12.2 using 2-(pyrid-3-yl)-4-(t-butyldimethylsilyloxy)butyronitrile to give the title compound.

13.3 Synthesis of N-(2-(pyrid-3-yl)-4-(t-butyldimethylsilyloxy)butyl)-3,4,5-trimethoxybenzamide Prepare by the method of Example 1.3 using 2-(pyrid-3-yl)-4-(t-butyldimethylsilyloxy)butylamine and 3,4,5-trimethoxybenzoyl chloride to give the title compound.

13.4 Synthesis of N-methyl-N-(2-(pyrid-3-yl)-4-(t-butyldimethylsilyloxy)butyl)-3,4,5-trimethoxybenzamide Prepare by the method of Example 1.4 using N-(2-(pyrid-3-yl)-4-(t-butyldimethylsilyloxy)butyl)-3,4,5-trimethoxybenzamide to give the title compound.

13.5 Synthesis of N-methyl-N-(2-(pyrid-3-yl)-4-hydroxybutyl)-3,4,5-trimethoxybenzamide Prepare by the method of Example 1.5 using N-methyl-N-(2-(pyrid-3-yl)-4-(t-butyldimethylsilyloxy)butyl)-3,4,5-trimethoxybenzamide to give the title compound.

13.6 Synthesis of N-methyl-N-(2-(pyrid-3-yl)-4-methanesulfonylbutyl)-3,4,5-trimethoxybenzamide Prepare by the method of Example 1.6 using N-methyl-N-(2-(pyrid-3-yl)-4-hydroxybutyl)-3,4,5-trimethoxybenzamide and methanesulfonyl chloride. Isolate by extraction using a saturated solution of sodium bicarbonate to give the title compound.

13.7 Synthesis of N-methyl-N-(4-(4-(1-(4-fluorobenzyl)-1H-benzimidazole-2-carbonyl)piperidin-1-yl)-2-(pyrid-3-yl)butyl)-3,4,5-trimethoxybenzamide Prepare by the method of Example 1.7 using N-methyl-N-(2-(pyrid-3-yl)-4-methanesulfonylbutyl)-3,4,5-trimethoxybenzamide and 4-(1-(4-fluorobenzyl)-1H-benzimidazole-2-carbonyl)piperidine to give the title compound.

EXAMPLE 14

N-Methyl-N-(4-(4-(4-benzhydrylidenepiperidin-1-yl)-2-(3,4-dichlorophenyl)butyl)benzamide

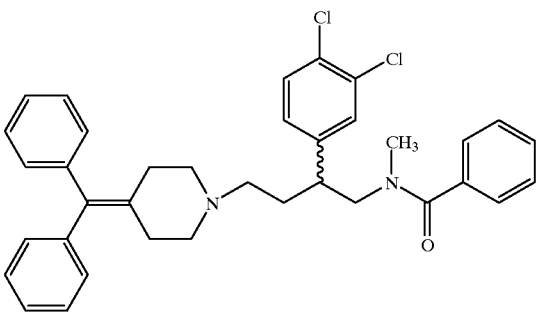

14.1 Synthesis of N-methyl-N-(4-(4-(4-benzhydrylidene)piperidin-1-yl)-2-(3,4-dichlorophenyl)butyl)benzamide Prepare by the method of Example 2.7 using N-methyl-N-(2-(3,4-dichlorophenyl)-4-methanesulfonylbutyl)benzamide and 4-benzhydrylidenepiperidine to give the title compound.

EXAMPLE 15

N-Methyl-N-(4-(4-(1H-benzimidazole-2-carbonyl)piperidin-1-yl)-2-(3,4-dichlorophenyl)butyl)-3,4,5-trimethoxybenzamide

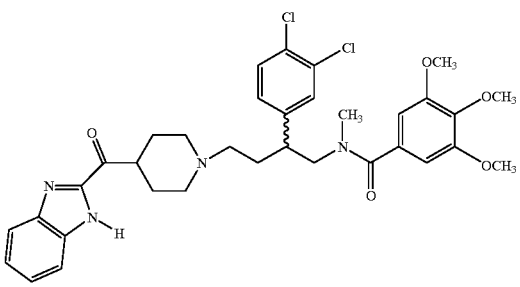

15.1 Synthesis of N-(2-(3,4-dichlorophenyl)-4-(t-butyldimethylsilyloxy)butyl)-3,4,5-trimethoxybenzamide Prepare by the method of Example 1.3 using 2-(3,4-dichlorophenyl)-4-(t-butyldimethylsilyloxy)butylamine and 3,4,5-trimethoxybenzoyl chloride to give the title compound.

15.2 Synthesis of N-methyl-N-(2-(3,4-dichlorophenyl)-4-(t-butyldimethylsilyloxy)butyl)-3,4,5-trimethoxybenzamide Prepare by the method of Example 1.4 using N-(2-(3,4-dichlorophenyl)-4-(t-butyldimethylsilyloxy)butyl)-3,4,5-trimethoxybenzamide to give the title compound.

15.3 Synthesis of N-methyl-N-(2-(3,4-dichlorophenyl)-4-hydroxybutyl)-3,4,5-trimethoxybenzamide Prepare by the method of Example 1.5 using N-methyl-N-(2-(3,4-dichlorophenyl)-4-(t-butyldimethylsilyloxy)butyl)-3,4,5-trimethoxybenzamide to give the title compound.

15.4 Synthesis of N-methyl-N-(2-(3,4-dichlorophenyl)-4-methanesulfonylbutyl)-3,4,5-trimethoxybenzamide Prepare by the method of Example 1.6 using N-methyl-N-(2-(3,4-dichlorophenyl)-4-hydroxybutyl)-3,4,5-trimethoxybenzamide and methanesulfonyl chloride to give the title compound.

15.5 Synthesis of N-methyl-N-(4-(4-(1H-benzimidazole-2-carbonyl)piperidin-1-yl)-2-(3,4-dichlorophenyl)butyl)-3,4,5-trimethoxybenzamide Prepare by the method of Example 1.7 using N-methyl-N-(2-(3,4-dichlorophenyl)-4-methanesulfonylbutyl)-3,4,5-trimethoxybenzamide and 4-(1H-benzimidazole-2-carbonyl)piperidine hydriodic acid salt to give the title compound.

EXAMPLE 16

N-Methyl-N-(4-(4-(1H-benzimidazole-2-carbonyl)piperidin-1-yl)-2-(3,4-dichlorophenyl)butyl)benzamide

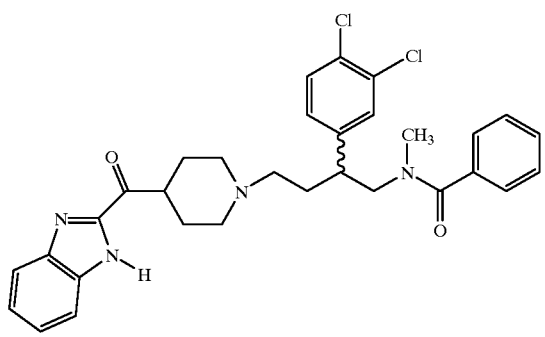

16.1 Synthesis of N-methyl-N-(4-(4-(1H-benzimidazole-2-carbonyl)piperidin-1-yl)-2-(3,4-dichlorophenyl)-butyl)benzamide Prepare by the method of Example 1.7 using N-methyl-N-(2-(3,4-dichlorophenyl)-4-methanesulfonylbutyl)benzamide and 4-(1H-benzimidazole-2-carbonyl)piperidine hydriodic acid salt to give the title compound.

EXAMPLE 17

N-Methyl-N-(4-(4-(1-(2-(morpholin-4-yl)ethyl)-1H-benzimidazole-2-carbonyl)piperidin-1-yl)-2-(3,4-dichlorophenyl)butyl)-3,4,5-trimethoxybenzamide

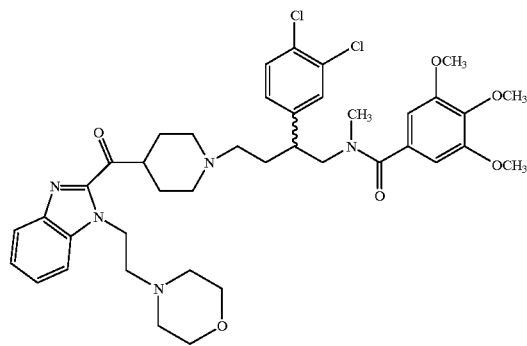

17.1 Synthesis of N-methyl-N-(4-(4-(1-(2-(morpholin-4-yl)ethyl)-1H-benzimidazole-2-carbonyl)piperidin-1-yl)-2-(3,4-dichlorophenyl)butyl)-3,4,5-trimethoxybenzamide Combine N-methyl-N-(4-(4-(1H-benzimidazole-2-carbonyl)-piperidin-1-yl)-2-(3,4-dichlorophenyl)butyl)-3,4,5-trimethoxybenzamide (0.70 mmol) and 4-(2-chloroethyl) morpholine hydrochloride (0.84 mmol), and potassium carbonate (3.36 mmol) in acetone (10 mL), water (4 mL), and dichloromethane (5 mL). Heat to reflux. After 20 hours, cool to ambient temperature and concentrate the reaction mixture in vacuo and dilute with ethyl acetate. Extract with saturated aqueous ammonium chloride solution, water, saturated aqueous sodium bicarbonate solution, and saturated aqueous sodium chloride solution. Dry the organic layer over $MgSO_4$, filter, and concentrate in vacuo to give the title compound.

EXAMPLE 18

N-Methyl-N-(4-(4-(1-(3-ethoxycarbonylpropyl)-1H-benzimidazole-2-carbonyl)piperidin-1-yl)-2-(3,4-dichlorophenyl)butyl)benzamide

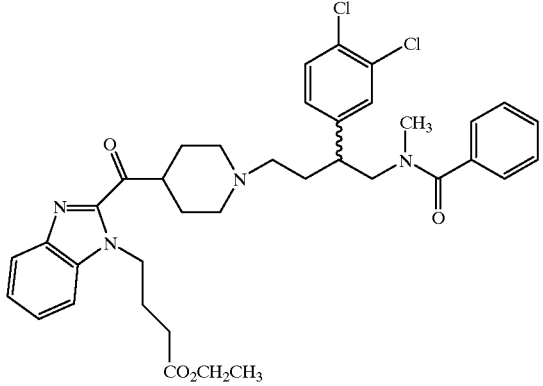

18.1 Synthesis of N-methyl-N-(4-(4-(1-(3-ethyoxycarbonylpropyl)-1H-benzimidazole-2-carbonyl)piperidin-1-yl)-2-(3,4-dichlorophenyl)butyl)benzamide Combine N-methyl-N-(4-(4-(1H-benzimidazole-2-carbonyl)piperidin-1-yl)-2-(3,4-dichlorophenyl)butyl)benzamide (1.35 mmol), ethyl 4-bromobutyrate (5.4 mmol), and potassium carbonate (2.24 g, 16.2 mmol) in 13/1 acetone/water (25 mL). Heat to reflux. After 38 hours, cool to ambient temperature and dilute with ethyl acetate. Extract with saturated aqueous ammonium chloride solution and saturated aqueous sodium chloride solution. Dry the organic layer over $MgSO_4$, filter, and concentrate in vacuo to give the title compound.

EXAMPLE 19

N-Methyl-N-(4-(4-(1-(4-methoxycarbonylbenzyl)-1H-benzimidazole-2-carbonyl)piperidin-1-yl)-2-(3,4-dichlorophenyl)butyl)benzamide

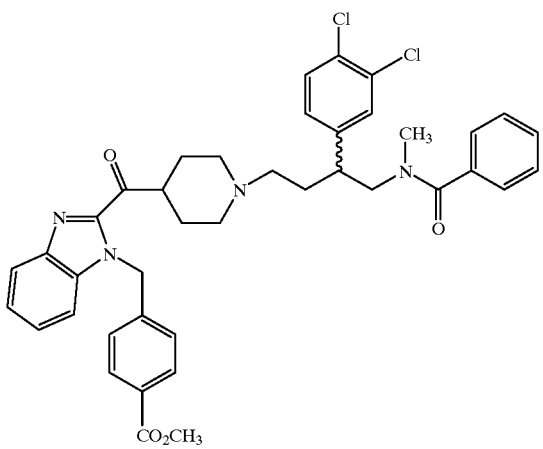

19.1 Synthesis of N-methyl-N-(4-(4-(1-(4-methoxycarbonylbenzyl)-1H-benzimidazole-2-carbonyl)piperidin-1-yl)-2-(3,4-dichlorophenyl)butyl)benzamide

47

Combine N-methyl-N-(4-(4-(1H-benzimidazole-2-carbonyl)piperidin-1-yl)-2-(3,4-dichlorophenyl)butyl)-benzamide (1.69 mmol), methyl (4-bromomethyl)benzoate (1.55 g, 6.76 mmol), and 1,8-diazabicyclo[5.4.0]undec-7-ene (2.06 g, 13.52 mmol) in acetonitrile (20 mL). Heat to reflux. After 72 hours, dilute the reaction mixture with ethyl acetate and extract three times with saturated aqueous ammonium chloride solution, saturated aqueous sodium bicarbonate solution, water, and saturated aqueous sodium chloride solution. Dry the organic layer over $Na_2SO_4$, filter, and concentrate in vacuo to give the title compound.

EXAMPLE 20

N-Methyl-N-(4-(4-(1-(4-carboxybenzyl)-1H-benzimidazole-2-carbonyl)piperidin-1-yl)-2-(3,4-dichlorophenyl)butyl)-benzamide

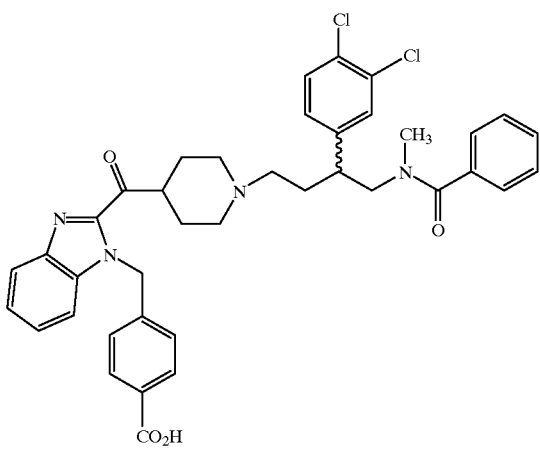

20.1 Synthesis of N-methyl-N-(4-(4-(1-(4-carboxybenzyl)-1H-benzimidazole-2-carbonyl)piperidin-1-yl)-2-(3,4-dichlorophenyl)butyl)benzamide Combine N-methyl-N-(4-(4-(1-(4-methoxycarbonylbenzyl)-1H-benzimidazole-2-carbonyl)piperidin-1-yl)-2-(3,4-dichlorophenyl)butyl)benzamide (0.92 mmol) and lithium hydroxide hydrate (0.12 g, 2.75 mmol) in 4/1 tetrahydrofuran/water (45 mL). After 72 hours, dilute the reaction mixture with water and evaporate in vacuo to remove most of the tetrahydrofuran. Acidify to pH 2 using 1 M hydrochloric acid solution. Extract with three times with ethyl acetate. Dry the combined organic layers over $Na_2SO_4$, filter, and concentrate in vacuo to give the title compound.

48

EXAMPLE 21

N-Methyl-N-(4-(4-(1-(2-ethyoxyethyl)-1H-benzimidazole-2-carbonyl)piperidin-1-yl)-2-(3,4-dichlorophenyl)butyl)-benzamide

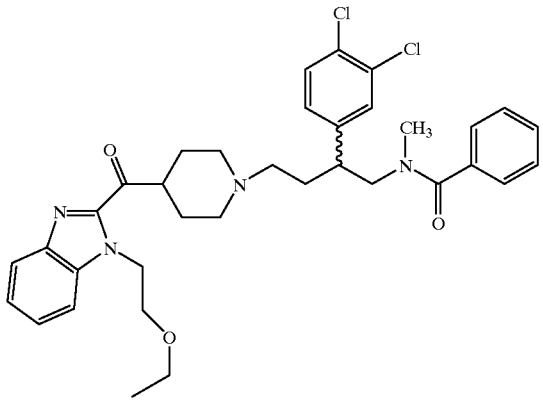

21.1 Synthesis of N-methyl-N-(4-(4-(1-(2-ethyoxyethyl)-1H-benzimidazole-2-carbonyl)piperidin-1-yl)-2-(3,4-dichlorophenyl)butyl)benzamide Combine N-methyl-N-(4-(4-(1H-benzimidazole-2-carbonyl)piperidin-1-yl)-2-(3,4-dichlorophenyl)butyl)-benzamide (1.36 mmol), 2-chloroethyl ethyl ether (0.59 g, 5.44 mmol), and 1,8-diazabicyclo[5.4.0]undec-7-ene (1.66 g, 10.9 mmol) in acetonitrile (16 mL). Heat to reflux. After 18 hours, cool to ambient temperature and dilute the reaction mixture with ethyl acetate. Extract twice with saturated aqueous solution of ammonium chloride, 5% aqueous solution of sodium bicarbonate, water, and saturated aqueous solution of sodium chloride. Dry the organic layer over $Na_2SO_4$, filter, and concentrate in vacuo to give the title compound.

PREPARATION 8

Synthesis of 4-(1-(fur-2-ylmethyl)-1H-benzimidazole-2-carbonyl)piperidine

Combine 1-(t-butoxycarbonyl)-4-(1H-benzimidazole-2-carbonyl)piperidine (1.16 mmol), furfuryl alcohol (0.10 mL, 1.16 mmol), and triphenylphosphine (0.33 g, 1.28 mmol) in tetrahydrofuran (5 mL). Add diethyl azodicarboxylate (0.20 mL, 1.28 mmol). After 18 hours, evaporate the reaction mixture in vacuo to give a residue. Partition the residue between ethyl acetate and water. Separate the organic layer and extract with water and saturated aqueous sodium chloride solution. Dry the organic layer over $Na_2SO_4$, filter, and evaporate invacuo to give the title compound. Chromatograph the residue on silica gel eluting with 5% acetone/dichloromethane to give 1-(t-butoxycarbonyl)-4-(1-(fur-2-ylmethyl)-1H-benzimidazole-2-carbonyl)piperidine. Cool 1-(t-butoxycarbonyl)-4-(1-(fur-2-ylmethyl)-1H-benzimidazole-2-carbonyl)piperidine (1.0 mmol), and dichloromethane (5 mL). Slowly add a cold solution of trifluoroacetic acid (1 mmol) in dichloromethane (2 mL).

After 15 minutes, partition the reaction mixture between dichloromethane and saturated aqueous sodium bicarbonate solution. Separate the organic layer and extract with brine. Dry the organic layer over $Na_2SO_4$, filter, and evaporate invacuo to give the title compound.

EXAMPLE 22

N-Methyl-N-(4-(4-(1-(fur-2-ylmethyl)-1H-benzimidazole-2-carbonyl)piperidin-1-yl)-2-phenylbutyl)benzamide

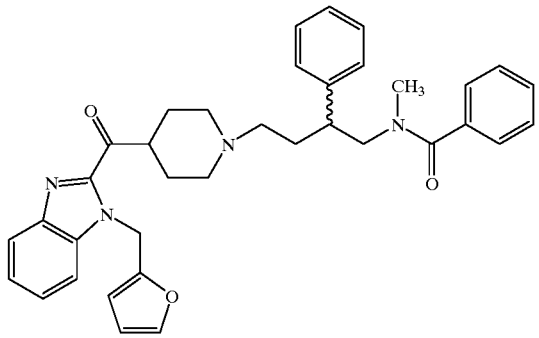

22.1 Synthesis of N-methyl-N-(4-(4-(1-(fur-2-ylmethyl)-1H-benzimidazole-2-carbonyl)piperidin-1-yl)-2-phenylbutyl)benzamide Prepare by the method of Example 1.7 using N-methyl-N-(2-phenyl-4-methanesulfonylbutyl)benzamide and 4-(1-(fur-2-ylmethyl)-1H-benzimidazole-2-carbonyl)piperidine to give the title compound.

PREPARATION 9

Synthesis of 4-(1-(2-(fur-2-ylmethoxy)ethyl)-1H-benzimidazole-2-carbonyl)piperidine Combine furfuryl alcohol (1 mL, 11.6 mmol) and tetrahydrofuran (20 mL). Add portionwise sodium hydride (0.57 g, 60% in oil, 14 mmol). After gas evolution ceases, add ethyl bromoacetate (1.3 mL, 11.7 mmol). Heat to reflux. After 2.5 hours cool to ambient temperature. After 18 hours, partition the reaction mixture between ethyl acetate and water. Separate the aqueous layer and extract twice with ethyl acetate. Combine the organic layers and extract with saturated aqueous sodium chloride solution, dry over $Na_2SO_4$, filter, and concentrate in vacuo to give a residue. Chromatograph the residue on silica gel eluting with 1% ethyl acetate/dichloromethane to give ethyl fur-2-ylmethoxyacetate: $R_f$=0.62 (silica gel, 5% ethyl acetate/dichloromethane).

Combine ethyl 2-fur-2-ylmethoxyaceate (1.2 g, 6.5 mmol) and tetrahydrofuran (10 mL). Cool in an ice-bath. Add dropwise a solution of lithium aluminum hydride (8.0 mL, 1.0 M in THF, 8.0 mmol). After 2 hours, add water (0.3 mL), add 15% sodium hydroxide solution (0.3 mL), and add water (0.9 mL). Stir vigorously. After 15 minutes, filter the reaction mixture and dry the filtrate over $Na_2SO_4$, filter, and concentrate in vacuo to give a residue. Chromatograph the residue on silica gel eluting with 2% ethyl acetate/dichloromethane to give fur-2-ylmethyl 2-hydroxyethyl ether: $R_f$=0.22 (silica gel, 5% acetone/dichloromethane) Combine 1-(t-butoxycarbonyl)-4-(1H-benzimidazole-2-carbonyl)piperidine (1.71 g, 5.2 mmol), fur-2-ylmethyl 2-hydroxyethyl ether (0.74 g, 5.2 mmol), and triphenylphosphine (1.67 g, 6.4 mmol) in tetrahydrofuran (20 mL). Add diethyl azodicarboxylate (1.0 mL, 6.35 mmol). After 21 hours, evaporate the reaction mixture in vacuo to give a residue. Chromatograph the residue on silica gel eluting with 5% acetone/dichloromethane to give 1-(t-butoxycarbonyl)-4-(1-(2-fur-2-ylmethoxy-ethyl)-1H-benzimidazole-2-carbonyl)piperidine: $R_f$=0.30 (silica gel, 5% acetone/dichloromethane).

Combine 1-(t-butoxycarbonyl)-4-(1-(2-fur-2-ylmethoxy-ethyl)-1H-benzimidazole-2-carbonyl)piperidine (1.0 mmol) and dioxane (10 mL). Cool in an ice bath. Slowly add a solution of hydrochloric aicd in dioxane (0.25 mL, 4 M, 1.0 mmol). After 45 minutes, dilute the reaction mixture with dichloromethane and extract with saturated aqueous sodium bicarbonate solution. Separate the organic layer and extract with brine. Dry the organic layer over $Na_2SO_4$, filter, and evaporate invacuo to give the title compound.

EXAMPLE 23

N-Methyl-N-(4-(4-(1-(2-(fur-2-ylmethoxy)ethyl)-1H-benzimidazole-2-carbonyl)piperidin-1-yl)-2-phenylbutyl)benzamide

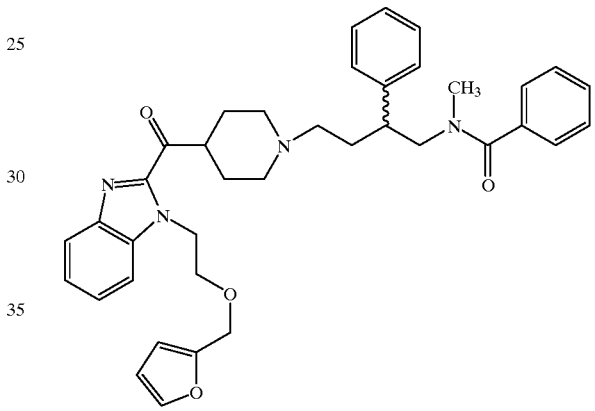

23.1 Synthesis of N-methyl-N-(4-(4-(1-(fur-2-ylmethyl)-1H-benzimidazole-2-carbonyl)piperidin-1-yl)-2-phenylbutyl)benzamide Prepare by the method of Example 1.7 using N-methyl-N-(2-phenyl-4-methanesulfonylbutyl)benzamide and 4-(1-(2-(fur-2-ylmethoxy)ethyl)-1H-benzimidazole-2-carbonyl) piperidine to give the title compound.

PREPARATION 10

Synthesis of 4-(1-(2-allyloxyethyl)-1H-benzimidazole-2-carbonyl)piperidine

Combine allyl hydroxyethyl ether (1.02 g, 10 mmol), and diisopropylethylamine (4.0 mL, 23 mmol), and dichloromethane (20 mL). Cool in an ice-bath. Add dropwise, methanesulfonyl chloride (1.0 mL, 13 mmol). After 1.5 hours, extract the reaction mixture with 1 M aqueous hydrochloric acid solution, saturated aqueous sodium bicarbonate solution, and saturated aqueous sodium chloride solution. Dry the organic layer over $Na_2SO_4$, filter, and evaporate invacuo to obtain allyl methanesulfonylethyl ether: $R_f$=0.80 (silica gel, 20% ethyl acetate/dichloromethane).

Combine 1-(t-butoxycarbonyl)-4-(1H-benzimidazole-2-carbonyl)piperidine (1.87 g, 5.68 mmol), allyl methanesulfonylethyl ether (1.83 g, 10.1 mmol), and potassium carbonate (1.60 g, 11.5 mmol) in acetone (21 mL) and water (7 mL). Heat to reflux. After 18 hours, concentrate the reaction mixture in vacuo to remove most of the acetone. Partition the concentrated reaction mixture between ethyl acetate and water. Separate the aqueous layer and extract three times with ethyl acetate. Extract the combined organic layers with saturated aqueous sodium chloride solution. Dry the organic layer over Na$_2$SO$_4$, filter, and evaporate in vacuo to to obtain a residue. Chromatograph the residue on silica gel eluting with 15% ethyl acetate/dichloromethane to give 1-(t-butoxycarbonyl)-4-(1-(2-allyloxyethyl)-1H-benzimidazole-2-carbonyl)piperidine: R$_f$=0.48 (silica gel, 20% ethyl acetate/dichloromethane).

Combine 1-(t-butoxycarbonyl)-4-(1-(2-allyloxyethyl)-1H-benzimidazole-2-carbonyl)piperidine (1.0 mmol) and dioxane (3 mL). Add a solution of hydrochloric acid in dioxane (4 mL, 4 M, 16 mmol). After 30 minutes, partition the residue between ethyl acetate and saturated aqueous sodium bicarbonate solution. Separate the organic layer and extract with saturated aqueous sodium chloride solution. Dry the organic layer over Na$_2$SO$_4$, filter, and evaporate in vacuo to give the title compound.

EXAMPLE 24

N-Methyl-N-(4-(4-(1-(2-allyloxyethyl)-1H-benzimidazole-2-carbonyl)piperidin-1-yl)-2-phenylbutyl)benzamide

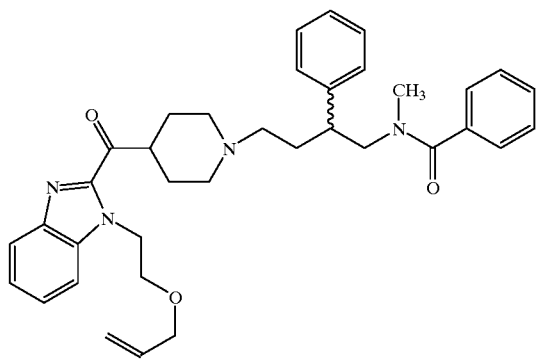

24.1 Synthesis of N-methyl-N-(4-(4-(1-(2-allyloxyethyl)-1H-benzimidazole-2-carbonyl)piperidin-1-yl)-2-phenylbutyl)benzamide Prepare by the method of Example 1.7 using N-methyl-N-(2-phenyl-4-methanesulfonylbutyl)benzamide and 4-(1-(2-allyloxyethyl)-1H-benzimidazole-2-carbonyl)piperidine to give the title compound.

PREPARATION 11

Synthesis of 4-(1-(2-(3,3-dimethylallyloxy)ethyl)-1H-benzimidazole-2-carbonyl)piperidine Prepare by the method of Preparation 10 using 3-methyl-2-butene hydroxyethyl ether.

EXAMPLE 25

N-Methyl-N-(4-(4-(1-(2-(3,3-dimethylallyloxy)ethyl)-1H-benzimidazole-2-carbonyl)piperidin-1-yl)-2-phenylbutyl)benzamide

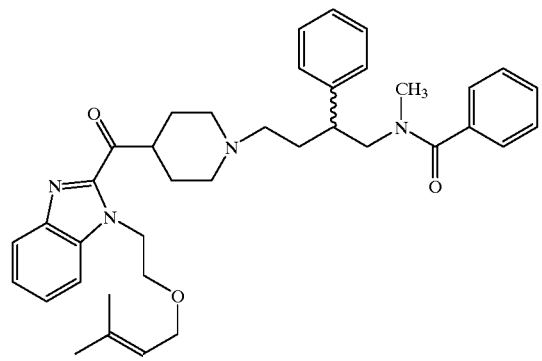

25.1 Synthesis of N-methyl-N-(4-(4-(1-(2-(3,3-dimethylallyloxy)ethyl)-1H-benzimidazole-2-carbonyl)piperidin-1-yl)-2-phenylbutyl)benzamide Prepare by the method of Example 1.7 using N-methyl-N-(2-phenyl-4-methanesulfonylbutyl)benzamide and 4-(1-(2-(3,3-dimethylallyloxy)ethyl)-1H-benzimidazole-2-carbonyl)piperidine to give the title compound.

EXAMPLE 26

N-Methyl-N-(4-(4-(1H-benzimidazole-2-carbonyl)piperidin-1-yl)-2-(3-chlorophenyl)butyl)-3,4,5-trimethoxybenzamide

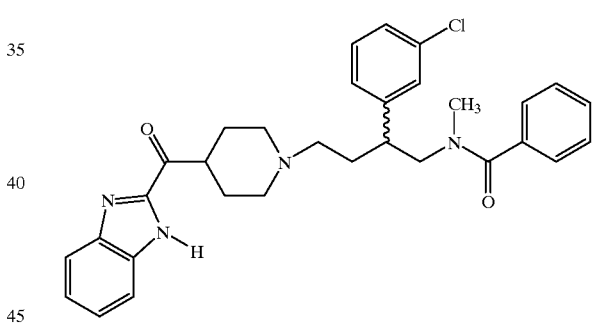

26.1 Synthesis of 2-(3-chlorophenyl)-4-(t-butyldimethylsilyloxy)butyronitrile

Prepare by the method of Example 1.1.1 using 3-chlorophenylacetonitrile and 1-(t-butyldimethylsilyloxy)-2-bromoethane to give the title compound.

26.2 Synthesis of 2-(3-chlorophenyl)-4-(t-butyldimethylsilyloxy)butylamine

Prepare by the method of Example 1.2 using 2-(3-chlorophenyl)-4-(t-butyldimethylsilyloxy)butyronitrile to give the title compound.

26.3 Synthesis of N-(2-(3-chlorophenyl)-4-(t-butyldimethylsilyloxy)butyl)-3,4,5-trimethoxybenzamide Prepare by the method of Example 1.3 using 2-(3-chlorophenyl)-4-(t-butyldimethylsilyloxy)butylamine and 3,4,5-trimethoxybenzoyl chloride to give the title compound.

26.4 Synthesis of N-methyl-N-(2-(3-chlorophenyl)-4-(t-butyldimethylsilyloxy)butyl)-3,4,5-trimethoxybenzamide Prepare by the method of Example 1.4 using N-(2-(3-chlorophenyl)-4-(t-butyldimethylsilyloxy)butyl)-3,4,5-trimethoxybenzamide to give the title compound.

26.5 Synthesis of N-methyl-N-(2-(3-chlorophenyl)-4-hydroxybutyl)-3,4,5-trimethoxybenzamide Prepare by the method of Example 1.5 using N-methyl-N-(2-(3-chlorophenyl)-4-(t-butyldimethylsilyloxy)butyl)-3,4,5-trimethoxybenzamide to give the title compound.

26.6 Synthesis of N-methyl-N-(2-(3-chlorophenyl)-4-methanesulfonylbutyl)-3,4,5-trimethoxybenzamide Prepare by the method of Example 1.6 using N-methyl-N-(2-(3-chlorophenyl)-4-hydroxybutyl)-3,4,5-trimethoxybenzamide to give the title compound.

26.7 Synthesis of N-methyl-N-(4-(4-(1H-benzimidazole-2-carbonyl)piperidin-1-yl)-2-(3-chlorophenyl)butyl)-3,4,5-trimethoxybenzamide Prepare by the method of Example 1.7 using N-methyl-N-(2-(3-chlorophenyl)-4-methanesulfonylbutyl)-3,4,5-trimethoxybenzamide and 4-(1H-benzimidazole-2-carbonyl)piperidine hydriodic acid salt to give the title compound.

EXAMPLE 27

N-Methyl-N-(4-(4-(1-(2-ethyoxyethyl)-1H-benzimidazole-2-carbonyl)piperidin-1-yl)-2-(3-chlorophenyl)butyl)-3,4,5-trimethoxybenzamide

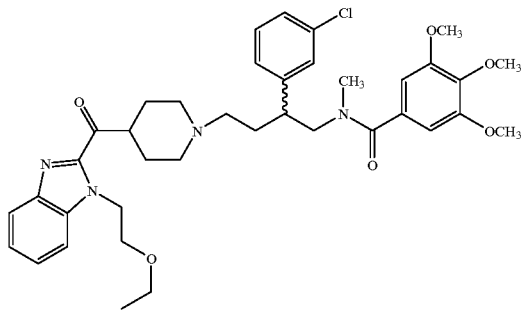

27.1 Synthesis of N-methyl-N-(4-(4-(1-(2-ethyoxyethyl)-1H-benzimidazole-2-carbonyl)piperidin-1-yl)-2-(3-chlorophenyl)butyl)-3,4,5-trimethoxybenzamide Prepare by the method of Example 21.1 using N-methyl-N-(4-(4-(1H-benzimidazole-2-carbonyl)piperidin-1-yl)-2-(3-chlorophenyl)butyl)-3,4,5-trimethoxybenzamide and 2-chloroethyl ethyl ether to give the title compound.

EXAMPLE 28

N-Methyl-N-(4-(4-(1H-benzimidazole-2-carbonyl)piperidin-1-yl)-2-(4-chlorophenyl)butyl)-3,4,5-trimethoxybenzamide

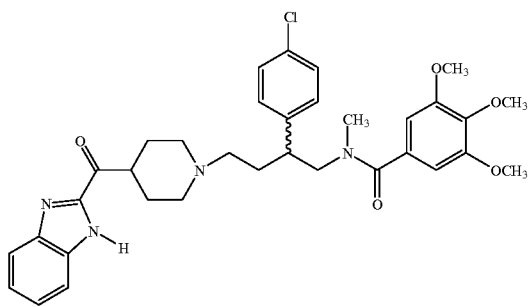

28.1 Synthesis of 2-(4-chlorophenyl)-4-(t-butyldimethylsilyloxy)butyronitrile

Prepare by the method of Example 1.1.1 using 4-chlorophenylacetonitrile and 1-(t-butyldimethylsilyloxy)-2-bromoethane to give the title compound.

28.2 Synthesis of 2-(4-chlorophenyl)-4-(t-butyldimethylsilyloxy)butylamine

Prepare by the method of Example 1.2 using 2-(4-chlorophenyl)-4-(t-butyldimethylsilyloxy)butyronitrile to give the title compound.

28.3 Synthesis of N-(2-(4-chlorophenyl)-4-(t-butyldimethylsilyloxy)butyl)-3,4,5-trimethoxybenzamide Prepare by the method of Example 1.3 using 2-(4-chlorophenyl)-4-(t-butyldimethylsilyloxy)butylamine and 3,4,5-trimethoxybenzoyl chloride to give the title compound.

28.4 Synthesis of N-methyl-N-(2-(4-chlorophenyl)-4-(t-butyldimethylsilyloxy)butyl)-3,4,5-trimethoxybenzamide Prepare by the method of Example 1.4 using N-(2-(4-chlorophenyl)-4-(t-butyldimethylsilyloxy)butyl)-3,4,5-trimethoxybenzamide to give the title compound.

28.5 Synthesis of N-methyl-N-(2-(4-chlorophenyl)-4-hydroxybutyl)-3,4,5-trimethoxybenzamide Prepare by the method of Example 1.5 using N-methyl-N-(2-(4-chlorophenyl)-4-(t-butyldimethylsilyloxy)butyl)-3,4,5-trimethoxybenzamide to give the title compound.

28.6 Synthesis of N-methyl-N-(2-(4-chlorophenyl)-4-methanesulfonylbutyl)-3,4,5-trimethoxybenzamide Prepare by the method of Example 1.6 using N-methyl-N-(2-(4-chlorophenyl)-4-hydroxybutyl)-3,4,5-trimethoxybenzamide to give the title compound.

28.7 Synthesis of N-methyl-N-(4-(4-(1H-benzimidazole-2-carbonyl)piperidin-1-yl)-2-(4-chlorophenyl)butyl)-3,4,5-trimethoxybenzamide Prepare by the method of Example 1.7 using N-methyl-N-(2-(4-chlorophenyl)-4-methanesulfonylbutyl)-3,4,5-trimethoxybenzamide and 4-(1H-benzimidazole-2-carbonyl)piperidine hydriodic acid salt to give the title compound.

EXAMPLE 29

N-Methyl-N-(4-(4-(1-(2-ethyoxyethyl)-1H-benzimidazole-2-carbonyl)piperidin-1-yl)-2-(4-chlorophenyl)butyl)-3,4,5-trimethoxybenzamide

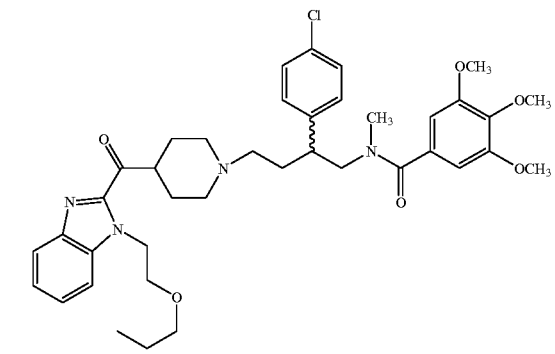

29.1 Synthesis of N-methyl-N-(4-(4-(1-(2-ethyoxyethyl)-1H-benzimidazole-2-carbonyl)piperidin-1-yl)-2-(4-chlorophenyl)butyl)-3,4,5-trimethoxybenzamide Prepare by the method of Example 21.1 using N-methyl-N-(4-(4-(1H-benzimidazole-2-carbonyl)piperidin-1-yl)-2-(4-chlorophenyl)butyl)-3,4,5-trimethoxybenzamide and 2-chloroethyl ethyl ether to give the title compound.

EXAMPLE 30

N-Methyl-N-(4-(4-(1H-benzimidazole-2-carbonyl)piperidin-1-yl)-2-(3,4-dimethylphenyl)butyl)-3,4,5-trimethoxybenzamide

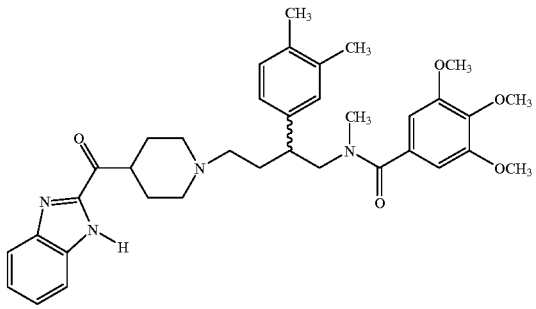

30.1 Synthesis of 2-(3,4-dimethylphenyl)-4-(t-butyldimethylsilyloxy)butyronitrile Prepare by the method of Example 1.1.1 using 3,4-dimethylphenylacetonitrile and 1-(t-butyldimethylsilyloxy)-2-bromoethane to give the title compound.

30.2 Synthesis of 2-(3,4-dimethylphenyl)-4-(t-butyldimethylsilyloxy)butylamine

Prepare by the method of Example 1.2 using 2-(3,4-dimethylphenyl)-4-(t-butyldimethylsilyloxy)butyronitrile to give the title compound.

30.3 Synthesis of N-(2-(3,4-dimethylphenyl)-4-(t-butyldimethylsilyloxy)butyl)-3,4,5-trimethoxybenzamide Prepare by the method of Example 1.3 using 2-(3,4-dimethylphenyl)-4-(t-butyldimethylsilyloxy)butylamine and 3,4,5-trimethoxybenzoyl chloride to give the title compound.

30.4 Synthesis of N-methyl-N-(2-(3,4-dimethylohenyl)-4-(t-butyldimethylsilyloxy)butyl)-3,4,5-trimethoxybenzamide Prepare by the method of Example 1.4 using N-(2-(3,4-dimethylphenyl)-4-(t-butyldimethylsilyloxy)butyl)-3,4,5-trimethoxybenzamide to give the title compound.

30.5 Synthesis of N-methyl-N-(2-(3,4-dimethylhenyl)-4-hydroxybutyl)-3,4,5-trimethoxybenzamide Prepare by the method of Example 1.5 using N-methyl-N-(2-(3,4-dimethylphenyl)-4-(t-butyldimethylsilyloxy)butyl)-3,4,5-trimethoxybenzamide to give the title compound.

30.6 Synthesis of N-methyl-N-(2-(3,4-dimethylphenyl)-4-methanesulfonylbutyl)-3,4,5-trimethoxybenzamide Prepare by the method of Example 1.6 using N-methyl-N-(2-(3,4-dimethylphenyl)-4-hydroxybutyl)-3,4,5-trimethoxybenzamide to give the title compound.

30.7 Synthesis of N-methyl-N-(4-(4-(1H-benzimidazole-2-carbonyl)piperidin-1-yl)-2-(3,4-dimethylphenyl)butyl)-3,4,5-trimethoxybenzamide Prepare by the method of Example 1.7 using N-methyl-N-(2-(3,4-dimethylphenyl)-4-methanesulfonylbutyl)-3,4,5-trimethoxybenzamide and 4-(1H-benzimidazole-2-carbonyl)piperidine hydriodic acid salt to give the title compound.

EXAMPLE 31

N-Methyl-N-(4-(4-(1-(imidazol-2-ylmethyl)-1H-benzimidazole-2-carbonyl)piperidin-1-yl)-2-phenylbutyl)benzamide

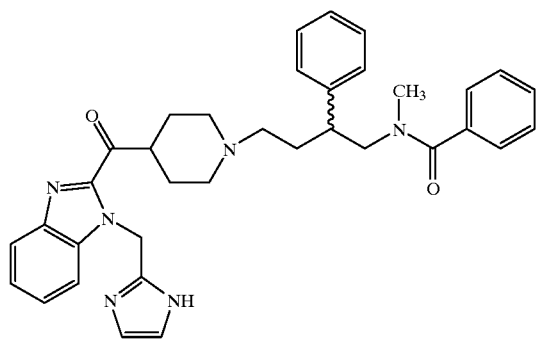

31.1 Synthesis of N-methyl-N-(4-(4-(1-(1-benzylimidazol-2-ylmethyl)-1H-benzimidazole-2-carbonyl)piperidin-1-yl)-2-phenylbutyl)benzamide Prepare by the method of Example 21.1 using N-methyl-N-(4-(4-(1H-benzimidazole-2-carbonyl)piperidin-1-yl)-2-phenylbutyl)benzamide and 1-benzyl-imidazol-2-ylmethylchloride hydrochloride to give the title compound.

31.2 Synthesis of N-methyl-N-(4-(4-(1-(imidazol-2-ylmethyl)-1H-benzimidazole-2-carbonyl)piperidin-1-yl)-2-phenylbutyl)benzamide Combine N-methyl-N-(4-(4-(1-(1-benzylimidazol-2-ylmethyl)-1H-benzimidazole-2-carbonyl)piperidin-1-yl)-2-phenylbutyl)benzamide (5 mmol) and 10% palladium-on-carbon (1.5 g) in methanol (50 mL). Add anhydrous ammonium formate (25 mmol). Heat to reflux. After 18 hours, filter, rinse with dichloromethane, and evaporate the filtrate in vacuo to give the title compound.

PREPARATION 12

Synthesis of 4-(1-(2-ethoxyethyl)-1H-benzimidazole)-4-hydroxypiperidine

Combine 1-(2-ethoxyethyl)-1H-benzimidazole (2.0 g, 10.51 mmol) and tetrahydrofuran (20 mL). Cool to −78° C. using a dry-ice/acetone bath. Add dropwise a solution of lithium diisopropylamide (4.62 mL, 2.5 M in hexane, 11.56 mmol). After 1 hour, add dropwise a solution of 1-(t-butoxycarbonyl)piperidin-4-one (2.09 g, 10.51 mmol) in tetrahydrofuran (10 mL). Warm to ambient temperature over 3 hours. Add water and separate the layers. Extract the aqueous layer three times with ethyl acetate. Dry the combined organic layers over $Na_2SO_4$, filter, and evaporate in vacuo to give a residue. Chromatograph the residue on silica gel eluting with 1/1 ethyl acetate/hexane to give 1-(t-butoxycarbonyl)-4-(1-(2-ethoxyethyl)-1H-benzimidazole)-4-hydroxypiperidine: $R_f$=0.25 (silica gel, 1/1 ethyl acetate/hexane).

Cool 1-(t-butoxycarbonyl)-4-(1-(2-ethoxyethyl)-1H-benzimidazole)-4-hydroxypiperidine (2.05 g) using an ice bath. Add dropwise trifluoroacetic acid (25 mL). After 1 hour, add diethyl ether (100 mL) and evaporate in vacuo to give a residue. Add dichloromethane and a 5% potassium carbonate solution. Stir vigorously. After 3 hours, separate the layers and extract the aqueous layer three times with dichloromethane. Combine the organic layers and dry over $K_2cO_3$, filter, and evaporate in vacuo to give the title compound: $R_f$=0.18 (silica gel, 2% triethylamine/ethyl acetate).

EXAMPLE 32

N-Methyl-N-(4-(4-(1-(2-ethoxyethyl)-1H-benzimidazole)-4-hydroxpiperidin-1-yl)-2-phenylbutyl)benzamide

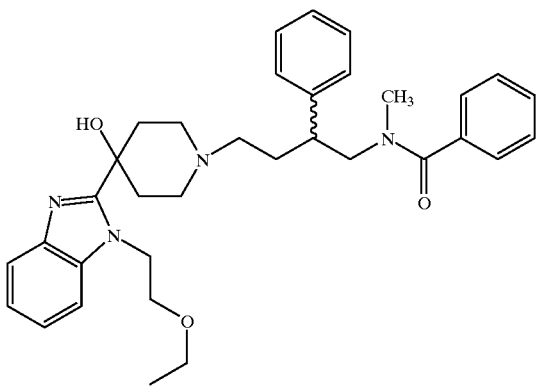

32.1 Synthesis of N-methyl-N-(4-(4-(1-(2-ethoxyethyl)-1H-benzimidazole)-4-hydroxypiperidin-1-yl)-2-phenylbutyl)benzamide Prepare by the method of Example 1.7 using N-methyl-N-(2-phenyl-4-methanesulfonylbutyl)benzamide and 4-(1-(2-ethoxyethyl)-1H-benzimidazole)-4-hydroxypiperidine to give the title compound.

PREPARATION 13

Synthesis of 2-methoxy-5-(1H-tetrazol-1-yl)benzoyl chloride

Combine 2-hydroxy-5-nitrobenzoic acid (21.5 g, 117 mmol), potassium carbonate (162.3 g, 1.174 mol), and methyl iodide (136.8 g, 96.4 mmol) in acetone (500 mL). Heat to reflux. After 18 hours, cool the reaction mixture to ambient temperature and add methyl iodide (136.8 g, 96.4 mmol). Again, heat to reflux. After 56 hours, cool the reaction mixture to ambient temperature and filter, rinse with acetone, and evaporate the filtrate in vacuo to give a residue. Recrystallize the residue from ethanol to give a second residue. Combine the second residue and chloroform (about 100 mL), filter and evaporate the filtrate in vacuo to give methyl 2-methoxy-5-nitrobenzoate. $R_f$=0.38 (silica gel, ethyl acetate/hexane 1/1).

Combine methyl 2-methoxy-5-nitrobenzoate (13.3 g, 63 mmol) and methanol. Add 5% palladium-on-carbon (0.66 g). Hydrogenate on a pressure apparatus at 50 psi. After 17 hours, filter through celite to remove the catalyst and evaporate the filtrate invacuo to give a residue. Combine the residue and dichloromethane and extract with water. Dry the organic layer over $Na_2SO_4$, filter, and evaporate invacuo to give methyl 2-methoxy-5-aminobenzoate. $R_f$=0.18 (silica gel, ethyl acetate/methanol 1/1). Elemental Analysis calculated for $C_9H_{11}NO_3$: C, 59.66; H, 6.12; N, 7.73. Found: C, 59.44; H, 6.04; N, 7.62.

Combine methyl 2-methoxy-5-aminobenzoate (3.94 g, 21.7 mmol) and triethyl orthoformate (12.8 g, 86.7 mmol) in glacial acetic acid (20 mL). After 20 hours, concentrate the reaction mixture invacuo to remove ethanol. Add glacial acetic acid (20 mL) and sodium azide (5.64 g, 86.7 mmol). Heat to 70° C. After 1 hour, add glacial acetic acid (10 mL) and continue to heat to 70° C. After an additional hour, cool the reaction mixture to ambient temperature, dilute with water (500 mL). Collect the solid by filtration, rinse with water, and dry to give methyl 2-methoxy-5-(1H-tetrazol-1-yl)benzoate.

Combine methyl 2-methoxy-5-(1H-tetrazol-1-yl) benzoate (2.86 g, 12.2 mmol) and a 1 M aqueous solution of sodium hydroxide (13.43 mL, 13.43 mmol) in methanol/water (100 mL, 5:1 vol./vol.). Heat to reflux. After 4 hours, concentrate in vacuo to remove most of the methanol, add water (50 mL), and adjust the pH to about 4 using a 1 M aqueous hydrochloric acid solution. Evaporate in vacuo to give a solid, slurry the solid with water, filter, and dry to give 2-methoxy-5-(1H-tetrazol-1-yl)benzoic acid.

Alternately, combine methyl 2-methoxy-5-(1H-tetrazol-1-yl)benzoate (13.3 g, 56.8 mmol) and methanol (150 mL). Add 1 M aqueous solution of sodium hydroxide (62.5 mL, 62.5 mmol). Heat to reflux. After 30 minutes, add methanol (50 mL) and water (50 mL) and continue the heat at reflux. After 1 hour, concentrate in vacuo to remove most of the solvent. Adjust the pH to about 1 to 2 using a 1 M aqueous hydrochloric acid solution to give a solid. Collect the solid by filtration, rinse with water, and dry to give 2-methoxy-5-(1H-tetrazol-1-yl)benzoic acid.

Combine 2-methoxy-5-(1H-tetrazol-1-yl)benzoic acid (1.2 g, 5.5 mmol) and dichloromethane (40 mL). Add dropwise oxalyl chloride (0.72 mL, 8.25 mmol) followed by dimethylformamide (3 drops). After 4 hours, evaporate in vacuo and dry to give the title compound.

EXAMPLE 33

N-Methyl-N-(4-(4-(1H-benzimidazole-2-carbonyl)piperidin-1-yl)-2-(4-fluorophenyl)butyl)-2-methoxy-5-(1H-tetrazol-1-yl)benzamide

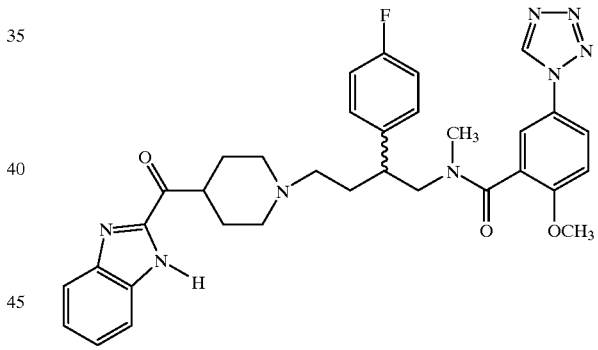

33.1 Synthesis of N-(2-(4-fluorophenyl)-4-(t-butyldimethylsilyloxy)butyl)-2-methoxy-5-(1H-tetrazol-1-yl)benzamide Combine 2-(4-fluorophenyl)-4-(t-butyldimethylsilyloxy)-butylamine (5.0 g, 16.8 mmol) and sodium bicarbonate (7.0 g, 83 mmol) in acetone (50 mL) and water (50 mL). Add 2-methoxy-5-(1H-tetrazol-1-yl)benzoyl chloride (3.3 g, 14.55 mmol). After 18 hours, dilute the reaction mixture with ethyl acetate, separate the layers, and extract the organic layer with a saturated aqueous solution of sodium bicarbonate, water, and then with brine. Dry the organic layer over $MgSO_4$, filter, and concentrate in vacuo to obtain a residue. Chromatograph the residue on silica gel eluting sequentially with 50% ethyl acetate/hexane and then 75% ethyl acetate/hexane to give, after drying, the title compound: $R_f$=0.58 (silica gel, ethyl acetate).

33.2 Synthesis of N-methyl-N-(2-(4-fluorophenyl)-4-(t-butyldimethylsilyloxy)butyl)-2-methoxy-5-(1H-tetrazol-1-yl)benzamide Combine N-(2-(4-fluorophenyl)-4-(t-butyldimethylsilyloxy)butyl)-2-methoxy-5-(1H-tetrazol-1-yl)benzamide (3.57 g, 7.13 mmol) in tetrahydrofuran (20 mL). Cool in a dry-ice/acetone bath. Add a solution of secbutyllithium (7.2 mL, 1.3 M in cyclohexane, 9.5 mmol). After 30 minutes, add iodomethane (2.0 mL, 32.1 mmol). Warm to ambient temperature and then heat to reflux. After 18 hours, Cool, dilute the reaction mixture with ethyl acetate, and extract with a saturated aqueous solution of sodium bicarbonate and then brine. Dry the organic layer over $Na_2SO_4$, filter, and concentrate in vacuo to give a residue. Chromatograph the residue on silica gel eluting with 3/7 ethyl acetate/hexane to give, after drying, the title compound: $R_f$=0.63 (silica gel, ethyl acetate).

33.3 Synthesis of N-methyl-N-(2-(4-fluorophenyl)-4-hdroxybutyl)-2-methox-5-(1H-tetrazol-1-yl)benzamide Prepare by the method of Example 1.5 using N-methyl-N-(2-(4-fluorophenyl)-4-(t-butyldimethylsilyloxy)butyl)-2-methoxy-5-(1H-tetrazol-1-yl)benzamide to give the title compound: $R_f$=0.18 (silica gel, ethyl acetate).

33.4 Synthesis of N-methyl-N-(2-(4-fluorophenyl)-4-methanesulfonylbutyl)-2-methoxy-5-(1H-tetrazol-1-yl)benzamide Prepare by the method of Example 1.6 using N-methyl-N-(2-(4-fluorophenyl)-4-hydroxybutyl)-2-methoxy-5-(1H-tetrazol-1-yl)benzamide to give the title compound.

33.5 Synthesis of N-methyl-N-(4-(4-(1H-benzimidazole-2-carbonyl)piperidin-1-yl)-2-(4-fluorophenyl)butyl)-2-methoxy-5-(1H-tetrazol-1-yl)benzamide Prepare by the method of Example 1.7 using N-methyl-N-(2-(4-fluorophenyl)-4-methanesulfonylbutyl)-2-methoxy-5-(1H-tetrazol-1-yl)benzamide and 4-(1H-benzimidazole-2-carbonyl)piperidine hydriodic acid salt to give the title compound.

EXAMPLE 34

N-Methyl-N-(4-(4-(1H-benzimidazole-2-carbonyl)piperidin-1-yl)-2-(3,4-dichlorophenyl)butyl)-2-methoxy-5-(1H-tetrazol-1-yl)benzamide

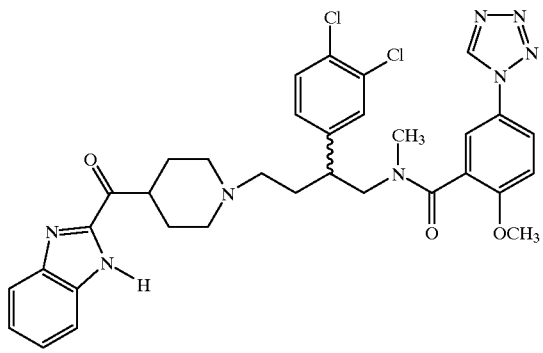

34.1 Synthesis of N-(2-(3,4-dichlorophenyl)-4-(t-butyldimethylsilyloxy)butyl)-2-methoxy-5-(1H-tetrazol-1-yl)benzamide Prepare by the method of Example 33.1 using 2-(3,4-dichlorophenyl)-4-(t-butyldimethylsilyloxy)butylamine (5.0 g, 16.8 mmol) to give the title compound.

34.2 Synthesis of N-methyl-N-(2-(3,4-dichlorophenyl)-4-(t-butyldimethylsilyloxy)butyl)-2-methoxy-5-(1H-tetrazol-1-yl)benzamide Prepare by the method of Example 1.4 using N-(2-(3,4-dichlorophenyl)-4-(t-butyldimethylsilyloxy)butyl)-2-methoxy-5-(1H-tetrazol-1-yl)benzamide to give the title compound.

34.3 Synthesis of N-methyl-N-(2-(3,4-dichlorophenyl)-4-hydroxybutyl)-2-methoxy-5-(1H-tetrazol-1-yl)benzamide Prepare by the method of Example 1.5 using N-methyl-N-(2-(3,4-dichlorophenyl)-4-(t-butyldimethylsilyloxy)butyl)-2-methoxy-5-(1H-tetrazol-1-yl)benzamide to give the title compound.

34.4 Synthesis of N-methyl-N-(2-(3,4-dichlorophenyl)-4-methanesulfonylbutyl)-2-methoxy-5-(1H-tetrazol-1-yl)benzamide Prepare by the method of Example 1.6 using N-methyl-N-(2-(3,4-dichlorophenyl)-4-hydroxybutyl)-2-methoxy-5-(1H-tetrazol-1-yl)benzamide to give the title compound.

34.5 Synthesis of N-methyl-N-(4-(4-(1H-benzimidazole-2-carbonyl)piperidin-1-yl)-2-(3,4-dichlorophenyl)butyl)-2-methoxy-5-(1H-tetrazol-1-yl)benzamide Prepare by the method of Example 1.7 using N-methyl-N-(2-(3,4-dichlorophenyl)-4-methanesulfonylbutyl)-2-methoxy-5-(1H-tetrazol-1-yl)benzamide and 4-(1H-benzimidazole-2-carbonyl)piperidine hydriodic acid salt to give the title compound.

PREPARATION 14

Synthesis of 2,2,2-trifluoroethyl trifluoromethanesulfonate

Combine 2,2,2-trifluoroethanol (12.4 mL g, 170 mmol), pyridine (13.6 mL, 170 mmol), and dichloromethane (40 mL). Cool in an ice bath. Add trifluoromethanesulfonic anhydride (50 g, 196 mmol) over about 45 minutes. After 15 minutes, add water, separate the layers and extract the organic layer with water. Dry the organic layer over $MgSO_4$, filter, and concentrate through a short path distillation apparatus to give the title compound: bp 89–91° C.

EXAMPLE 35

N-Methyl-N-(4-(4-(1-(2,2,2-trifluoroethyl)-1H-benzimidazole-2-carbonyl)piperidin-1-yl)-2-(4-fluorophenyl)butyl)-2-methoxy-5-(1H-tetrazol-1-yl)benzamide

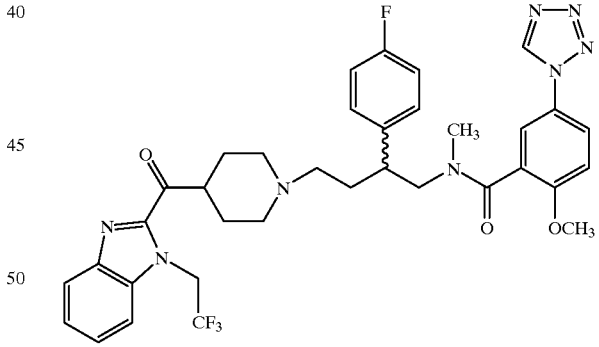

35.1 Synthesis of N-methyl-N-(4-(4-(1-(2,2,2-trifluoroethyl)-1H-benzimidazole-2-carbonyl)piperidin-1-yl)-2-(4-fluorophenyl)butyl)-2-methoxy-5-(1H-tetrazol-1-yl)benzamide Prepare by the method of Example 21.1 using 2,2,2-trifluorethyl trifluoromethanesulfonate to give the title compound.

PREPARATION 15

Synthesis of 4-(1-allyl-1H-benzimidazole-2-carbonyl)piperidine

Prepare by the method of Preparation 8 using allyl alcohol to give the title compound.

EXAMPLE 36

N-Methyl-N-(4-(4-(1-allyl-1H-benzimidazole-2-carbonyl)piperidin-1-yl)-2-(3,4-dichlorophenyl)butyl)-2-methoxy-5-(1H-tetrazol-1-yl)benzamide

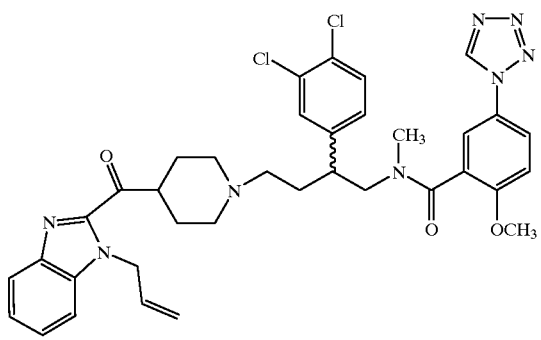

36.1 Synthesis N-methyl-N-(4-(4-(1-allyl-1H-benzimidazole-2-carbonyl)piperidin-1-yl)-2-(3,4-dichlorophenyl)butyl)-2-methoxy-5-(1H-tetrazol-1-yl)benzamide Prepare by the method of Example 1.7 using N-methyl-N-(2-(3,4-dichlorophenyl)-4-methanesulfonylbutyl)-2-methoxy-5-(1H-tetrazol-1-yl)benzamide and 4-(1-allyl-1H-benzimidazole-2-carbonyl)piperidine to give the title compound.

PREPARATION 16

Synthesis of 2-methoxy-5-(4H-triazol-4-yl)benzoyl chloride

According to the method of *J. Chem. Soc.* (C), 1664 (1967), combine methyl 2-methoxy-5-aminobenzoate (2.0 g, 11 mmol), N,N-dimethylformamide azine (1.56 g, 11 mmol), p-toluenesulfonic acid (190 mg) in toluene (25 mL). Fit the reaction vessel with a gas inlet such that the head space of the vessel is swept with argon and scrub the effluent through dilute aqueous hydrochloric acid solution. Heat to reflux. After 20 hours, concentrate the reaction mixture in vacuo to give a residue. Partition the residue between dichloromethane and a saturated aqueous sodium bicarbonate solution. Extract the aqueous layer twice with dichloromethane. Combine the organic layers, dry over $MgSO_4$, filter, and evaporate in vacuo to give a residue. Chromatograph the residue on silica gel eluting sequentially with 70% ethyl acetate/dichloromethane and then 5% methanol/dichloromethane to give a residue. Recrystallize the residue form ethyl acetate/hexane to give methyl 2-methoxy-5-(4H-triazol-4-yl)benzoate: mp; 191–195.5° C.

Alternately, according to the method of *J. Med. Chem.*, 21, 1100 (1978), combine methyl 2-methoxy-5-aminobenzoate (1.8 g, 10 mmol), diformyl hydrazine (0.97 g, 11 mmol), and phosphorous pentoxide (1.84 g, 13 mmol). Heat to 160° C. After 1.5 hours, cool the reaction mixture and add a saturated aqueous solution of sodium bicarbonate. Extract three times with dichloromethane. Dry the combined organic layers over $MgSO_4$, filter, and evaporate in vacuo to give a residue. Chromatograph the residue on silica gel eluting sequentially with 40% ethyl acetate/dichloromethane and then 5% methanol/dichloromethane to give methyl 2-methoxy-5-(4H-triazol-4-yl)benzoate: mp; 179–182° C. Combine methyl 2-methoxy-5-(4H-triazol-4-yl)benzoate (56 mmol) and methanol (200 mL) and water (50 mL). Add 1 M aqueous solution of sodium hydroxide (62.5 mL, 62.5 mmol). Heat to reflux. After 8 hour, concentrate in vacuo to remove most of the solvent. Adjust the pH to about 1 to 2 using a 1 M aqueous hydrochloric acid solution, extract with dichloromethane. Dry the organic layer over $MgSO_4$, filter, and evaporate invacuo to give 2-methoxy-5-(4H-triazol-4-yl)benzoic acid.

Combine 2-methoxy-5-(4H-triazol-4-yl)benzoic acid (5 mmol) and dichloromethane (40 mL). Add dropwise oxalyl chloride (0.72 mL, 8.25 mmol) followed by dimethylformamide (3 drops). After 4 hours, evaporate in vacuo and dry to give the title compound.

EXAMPLE 37

N-Methyl-N-(4-(4-(1-(pyrid-2-ylmethyl)-1H-benzimidazole-2-carbonyl)piperidin-1-yl)-2-(4-fluoroohenyl)butyl)-2-methoxy-5-(4H-triazol-4-yl)benzamide

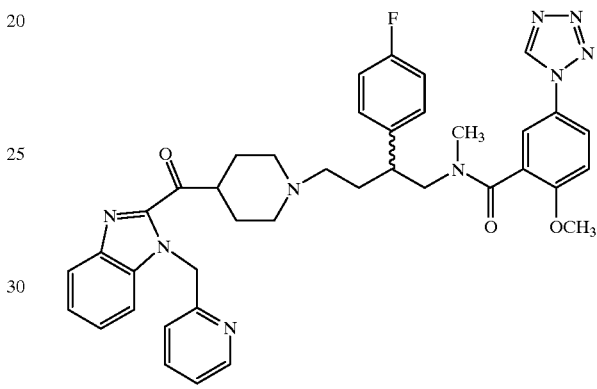

37.1 Synthesis of N-(2-(4-fluorophenyl)-4-(t-butyldimethylsilyloxy)butyl)-2-methoxy-5-(4H-triazol-4-yl)benzamide Prepare by the method of Example 33.1 using 2-(4-fluorophenyl)-4-(t-butyldimethylsilyloxy)butylamine and 2-methoxy-5-(4H-triazol-4-yl)benzoyl chloride to give the title compound.

37.2 Synthesis of N-methyl-N-(2-(4-fluorophenyl)-4-(t-butyldimethylsilyloxy)butyl)-2-methoxy-5-(4H-triazol-4-yl)benzamide Prepare by the method of Example 1.4 using N-(2-(4-fluorophenyl)-4-(t-butyldimethylsilyloxy)butyl)-2-methoxy-5-(4H-triazol-4-yl)benzamide to give the title compound.

37.3 Synthesis of N-methyl-N-(2-(4-fluorophenyl)-4-hydroxybutyl)-2-methoxy-5-(4H-triazol-4-yl)benzamide Prepare by the method of Example 1.5 using N-methyl-N-(2-(4-fluorophenyl)-4-(t-butyldimethylsilyloxy)butyl)-2-methoxy-5-(4H-triazol-4-yl)benzamide to give the title compound.

37.4 Synthesis of N-methyl-N-(2-(4-fluorophenyl)-4-methanesulfonylbutyl)-2-methoxy-5-(4H-triazol-4-yl)benzamide Prepare by the method of Example 1.6 using N-methyl-N-(2-(4-fluorophenyl)-4-hydroxybutyl)-2-methoxy-5-(4H-triazol-4-yl)benzamide to give the title compound.

37.5 Synthesis of N-methyl-N-(4-(4-(1-(pyrid-2-ylmethyl)-1H-benzimidazole-2-carbonyl)piperidin-1-yl)-2-(4-fluorophenyl)butyl)-2-methoxy-5-(4H-triazol-4-yl)benzamide Prepare by the method of Example 1.7 using N-methyl-N-(2-(4-fluorophenyl)-4-methanesulfonylbutyl)-2- methoxy-5-(4H-triazol-4-yl)benzamide and 4-(1-(pyrid-2-ylmethyl)-1H-benzimidazole-2-carbonyl)piperidine hydriodic acid salt to give the title compound.

PREPARATION 18

Synthesis of 2-methoxy-5-trifluoromethoxybenzoyl chloride

Combine 2-methoxy-5-trifluoromethoxybenzene (1.0 g, 5.2 mmol) and trifluoroacetic acid (200 mL). Add slowly portionwise hexamethylenetetraamine (26 g, 185.7 mmol). Heat at 60° C. After 24 hours, cool to ambient temperature and pour the reaction mixture into a 2 M aqueous solution of sulfuric acid (500 mL). Cool and extract ten times with diethyl ether. Dry the combined organic layers over $Na_2SO_4$, filter, and evaporate in vacuo to give a residue. Chromatograph the residue on silica gel eluting with 1/4 ethyl acetate/hexane to give 2-methoxy-5-trifluoromethoxybenzaldehyde.

According to the method of *Heterocycles*, 16, 2091 (1981), combine 2-methoxy-5-trifluoromethoxybenzaldehyde (0.58 g, 2.65 mmol) and 2-methylbut-2-ene (37 mL) in t-butanol (16 mL). Add dropwise a solution of sodium dihydrogen phosphate hydrate (0.92 g) and sodium chlorite (0.42 g, 4.7 mmol) in water (10 mL). After 4 hours, adjust the pH of the reaction mixture to about 8 to 9 using a 1 M aqueous sodium hydroxide solution. Evaporate the reaction mixture in vacuo at about ambient temperature to remove most of the t-butanol. Add water (40 mL) and extract three times with hexane (10 mL). Adjust the pH of the aqueous layer to about 1 using a 1 M aqueous hydrochloric acid solution and extract five times with diethyl ether. Combine the organic layers, dry over $Na_2SO_4$, filter, and evaporate in vacuo to give a residue. Chromatograph the residue on silica gel eluting with 1/1 ethyl acetate/hexane containing 0.5% acetic acid to give 2-methoxy-5-trifluoromethoxybenzoic acid: $R_f$=0.34 (silica gel, 1/1 ethyl acetate/hexane containing 0.5% acetic acid).

Combine 2-methoxy-5-trifluoromethoxybenzoic acid (0.6 g, 2.53 mmol) and dichloromethane (10 mL). Cool in an ice bath. Add dropwise oxalyl chloride (0.64 mL, 5.0 mmol) followed by dimethylformamide (1 drop). Warm to ambient temperature. After 3 hours, evaporate in vacuo and dry to give the title compound.

EXAMPLE 38

N-Methyl-N-(4-(4-(1H-benzimidazole-2-carbonyl)piperidin-1-yl)-2-(3,4-dichlorophenyl)butyl)-2-methoxy-5-trifluoromethoxybenzamide

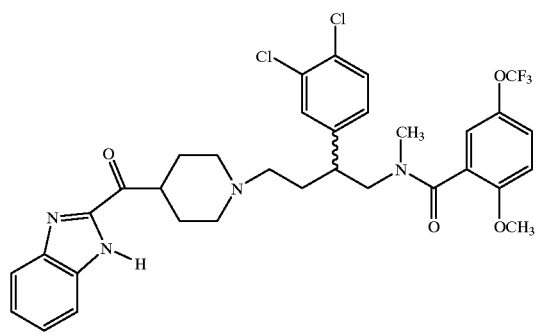

38.1 Synthesis of N-(2-(3,4-dichlorophenyl)-4-(t-butyldimethylsilyloxy)butyl)-2-methoxy-5-trifluoromethoxybenzamide Prepare by the method of Example 33.1 using 2-(3,4-dichlorophenyl)-4-(t-butyldimethylsilyloxy)butylamine (5.0 g, 16.8 mmol) and 2-methoxy-5-trifluoromethoxybenzoyl chloride to give the title compound.

38.2 Synthesis of N-methyl-N-(2-(3,4-dichlorophenyl)-4-(t-butyldimethylsilyloxy)butyl)-2-methoxy-5-trifluoromethoxybenzamide Prepare by the method of Example 1.4 using N-(2-(3,4-dichlorophenyl)-4-(t-butyldimethylsilyloxy)butyl)-2-methoxy-5-trifluoromethoxybenzamide to give the title compound.

38.3 Synthesis of N-methyl-N-(2-(3,4-dichlorophenyl)-4-hydroxybutyl)-2-methoxy-5-trifluoromethoxybenzamide Prepare by the method of Example 1.5 using N-methyl-N-(2-(3,4-dichlorophenyl)-4-(t-butyldimethylsilyloxy)butyl)-2-methoxy-5-trifluoromethoxybenzamide to give the title compound.

38.4 Synthesis of N-methyl-N-(2-(3,4-dichlorophenyl)-4-methanesulfonylbutyl)-2-methoxy-5-trifluoromethoxybenzamide Prepare by the method of Example 1.6 using N-methyl-N-(2-(3,4-dichlorophenyl)-4-hydroxybutyl)-2-methoxy-5-trifluoromethoxybenzamide to give the title compound.

38.5 Synthesis of N-methyl-N-(4-(4-(1H-benzimidazole-2-carbonyl)piperidin-1-yl)-2-(3,4-dichlorophenyl)butyl)-2-methoxy-5-trifluoromethoxybenzamide Prepare by the method of Example 1.7 using N-methyl-N-(2-(3,4-dichlorophenyl)-4-methanesulfonylbutyl)-2-methoxy-5-trifluoromethoxybenzamide and 4-(1H-benzimidazole-2-carbonyl)piperidine hydriodic acid salt to give the title compound.

EXAMPLE 39

N-Methyl-N-(4-(4-(1-(2-ethoxyethyl)-1H-benzimidazole-2-carbonyl)piperidin-1-yl)-2-(3,4-dichlorophenyl)butyl)-2-methoxy-5-trifluoromethoxybenzamide

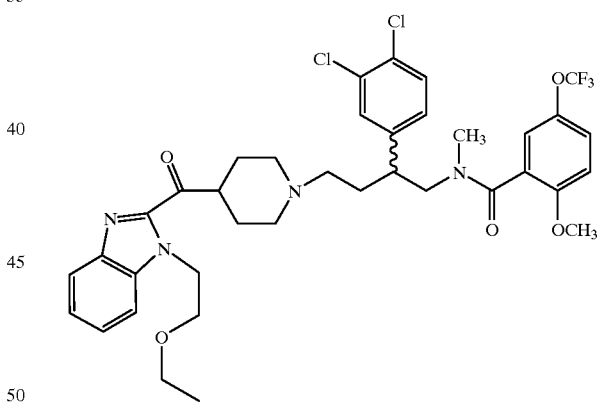

39.1 Synthesis of N-methyl-N-(4-(4-(1-(2-ethoxyethyl)-1H-benzimidazole-2-carbonyl)piperidin-1-yl)-2-(3,4-dichlorophenyl)butyl)-2-methoxy-5-trifluoromethoxybenzamide Prepare by the method of Example 21.1 using N-methyl-N-(4-(4-(1H-benzimidazole-2-carbonyl)piperidin-1-yl)-2-(3,4-dichlorophenyl)butyl)-2-methoxy-5-trifluoromethoxybenzamide amd 2-chloroethyl ethyl ether to give the title compound.

PREPARATION 17

Synthesis of 4-(1-(2-(2,2,2-trifluoroethoxy)ethyl)-1H-benzimidazole-2-carbonyl)piperidine hydriodic acid salt According to the procedure of *Tet. Lett.*, 35, 5997–6000 (1994), combine 1-hydroxy-2-tetrahydropyran-2- yloxyethane (*J. Chem. Soc. Chem. Commun.*, 1766 (1990)) (5.0 mmol), 1,1-diethylazodicarboxylate (10 mmol), 2,2,2-trifluuoroethanol (100 mmol), and tributylphosphine (10 mmol) in benzene (100 mL). After 6 hours, concentrate in vacuo to give a residue. Chromatograph on silica gel to give 2-tetrahydropyran-2-yloxyethyl 2,2,2-trifluorethyl ether.

Combine 2-tetrahydropyran-2-yloxyethyl but-2-en-1-yl ether (2 mmol) and magnesium bromide (6 mmol) in diethyl ether (10 mL). After 24 hours, extract with water and then brine. Dry the organic layer over $Na_2SO_4$, filter, and concentrate in vacuo to give 2-hydroxyethyl 2,2,2-trifluorethyl ether.

Prepare by the method of Preparation 9 using 2-hydroxyethyl 2,2,2-trifluorethyl ether and 1-(t-butoxycarbonyl)-4-(1H-benzimidazole-2-carbonyl) piperidine (2.0 g, 6.1 mmol) to give 1-(t-butoxycarbonyl)-4-(1-(2-(2,2,2-trifluoroethoxy)ethyl)-1H-benzimidazole-2-carbonyl)piperidine.

Combine 1-(t-butoxycarbonyl)-4-(1-(2-(2,2,2-trifluoroethoxy)ethyl)-1H-benzimidazole-2-carbonyl) piperidine (5.0 mmol) and dichloromethane (150 mL). Cool to 0° C. using an ice bath. Add hydriodic acid (gas) until the solution is saturated and stir. After 30 minutes, again add hydriodic acid (gas) until the solution is saturated. After 2 hours, evaporate in vacuo to give, after drying, the title compound.

EXAMPLE 40

N-Methyl-N-(4-(4-(1-(2-(2,2,2-trifluoroethoxy) ethyl)-1H-benzimidazole-2-carbonyl)piperidin-1-yl)-2-(4-fluorophenyl)butyl)-2-methoxy-5-(1H-tetrazol-1-yl)benzamide

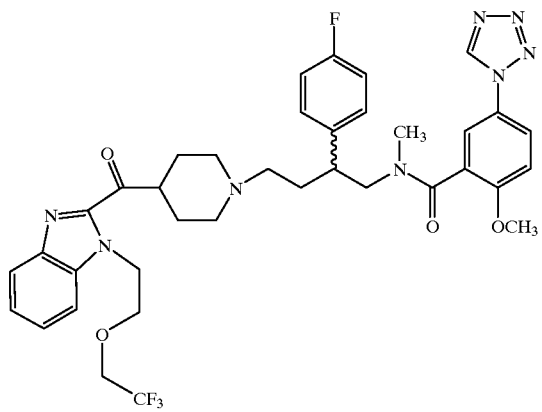

40.1 Synthesis of N-methyl-N-(4-(4-(1-(2-(2,2,2-trifluoroethoxy)ethyl)-1H-benzimidazole-2-carbonyl) piperidin-1-yl)-2-(4-fluorophenyl)butyl)-2-methoxy-5-(1H-tetrazol-1-yl)benzamide Prepare by the method of Example 1.7 using N-methyl-N-(2-(4-fluorophenyl)-4-methanesulfonylbutyl)-2-methoxy-5-(1H-tetrazol-1-yl)benzamide and 4-(1-(2-(2,2,2-trifluoroethoxy)ethyl)-1H-benzimidazole-2-carbonyl) piperidine hydriodic acid salt to give the title compound.

The tachykinins are a class of neuropeptides which share a common C-terminus sequence, Phe-Xaa-Gly-Leu-Met-$NH_2$. The tachykinins are widely distributed in the peripheral and central nervous systems where they bind to at least three receptor types. Among the tachykinin receptors, the $NK_1$, $NK_2$, and $NK_3$ receptors are defined by the preferred binding affinity of substance P, neurokinin A (NKA), and neurokinin B (NKB), respectively.

The use of tachykinin antagonists is indicated as therapy for a variety of tachykinin-mediated diseases and conditions, including: hypersensitivity reactions; adverse immunological reactions; asthma; bronchitis; allergic rhinitis, including seasonal rhinitis and sinusitis; allergies; contact dermatitis; atopic dermatitis; inflammatory bowel diseases, including Crohn's disease and ulcerative colitis; and emesis.

It is understood that tachykinin-mediated diseases and conditions are those diseases and conditions in which the tachykinins are involved, either in whole or in part, in their clinical manifestation(s). Moreover, the tachykinins involvement is not necessarily causative of a particular tachykinin-mediated disease and condition. Tachykinin antagonists are useful in controlling or providing therapeutic relief of those tachykinin-mediated diseases and conditions.

The present invention provides new and useful tachykinin antagonists of formula (1) or stereoisomers or pharmaceutically acceptable salts thereof.

In a further embodiment, as tachykinin antagonists the present invention provides a method of treating tachykinin-mediated diseases and conditions, including: hypersensitivity reactions; adverse immunological reactions; asthma; bronchitis; allergic rhinitis, including seasonal rhinitis and sinusitis; allergies; contact dermatitis; atopic dermatitis; inflammatory bowel diseases, including Crohn's disease and ulcerative colitis; and emesis in a patient in need thereof comprising administering to said patient a therapeutically effective amount of a compound of formula (1).

Immediate hypersensitivity can occur when an IgE antibody response is directed against innocuous antigens, such as pollen. During such a response there is generally a subsequent release of pharmacological mediators, such as histamine, by IgE-sensitized mast cells resulting in an acute inflammatory reaction. The characteristics of the response are determined by the tissue in which the reaction occurs and gives rise to allergic diseases including: allergic rhinitis, including seasonal rhinitis and sinusitis; pulmonary diseases, such as asthma; allergic dermatisis, such as urticaria, angioedema, eczema, atopic dermatitis, and contact dermatitis; gastrointestinal allergies, such as those caused by food or drugs; cramping; nausea; vomiting; diarrhea; and ophthalmic allergies.

Histamine, producing its effects via activation of the $H_1$ receptor, is an important mediator of the above responses involved in immediate hypersensitivity. In the acute phase of allergic rhinitis, histamine $H_1$ receptor antagonists have been shown to effectively inhibit the nasal itchiness, rhinorrhea, and sneezing associated with that condition. However, histamine $H_1$ receptor antagonists are less effective in relieving nasal congestion. The acute response to allergen in rhinitis is often followed by a chronic inflammatory response during which the inflamed mucosa becomes hypersensitive to both antigens and nonspecific irritants. Histamine $H_1$ receptor antagonists are also ineffective in attenuating the symptoms of the chronic phase of the response.

The present invention provides new and useful histamine antagonists of formula (1) or stereoisomers or pharmaceutically acceptable salts thereof.

In a further embodiment, as histamine antagonists the present invention provides a method of treating allergic diseases, including: allergic rhinitis, including seasonal rhinitis and sinusitis; pulmonary diseases, such as asthma; allergic dermatosis, such as urticaria, angioedema, eczema, atopic dermatitis, and contact dermatitis; allergic conjuctivitis; gastrointestinal allergies, such as those caused by food or drugs; cramping; nausea; vomiting; diarrhea; and ophthalmic allergies and uveitis; in a patient in need thereof comprising administering to said patient a therapeutically effective amount of a compound of formula (1).

In addition to histamine, the tachykinins, particularly substance P, are also important contributors to the allergic response and produce some symptoms distinct from those produced by a histamine response. This occurs because sensory nerves of trigeminal origin, located around blood vessels and within the nasal mucosal lining, upon stimulation by irritants or inflammatory mediators, such as histamine, will release tachykinins.

Patients with allergic rhinitis have been shown to have higher nasal levels of substance P when their rhinitis symptoms are present. Mosimann et al. *J. Allergy Clin. Immunol.* 92, 95 (1993); Takeyama et al., *J. Pharm. Pharmacol.* 46, 41 (1994); and Wantanabe et al., *Ann. Otol. Rhinol. and Laryngol.*, 102, 16 (1993). In humans, topical or intravenous administration of tachykinins induces nasal obstruction, recruitment of inflammatory cells, glandular secretion, and microvascular leakage in allergic rhinitis. The nasal obstruction produced by substance P was found to be $NK_1$ receptor mediated. Braunstein et al., *Am. Rev. Respir. Dis.*, 144, 630 (1991); Devillier et al., *Eur. Respir. J.* 1, 356 (1988). Furthermore, sensory nerve-mediated effects, such as nasal irritability and hyperresponsiveness which occurs in late phase allergic reactions, also result from tachykinin release. Anggard, *Acta Otolaryngol.* 113, 394 (1993). Depletion of tachykinins from nasal sensory nerves after chronic capsaicin administration improved rhinitic symptoms in affected individuals. Lacroix et al., *Clin. and Exper. Allergy*, 21, 595 (1991).

Antagonism of the effects of histamine on the $H_1$ receptor is useful in the treatment of allergic diseases, such as rhinitis. Likewise, antagonism of the effects of the tachykinins, particularly substance P on its preferred receptor, is useful in the treatment of symptoms which are concurrent with allergic diseases. Therefore, the potential benefits of an antagonist with affinity at both the $H_1$ and $NK_1$ receptors would be to reduce or prevent clinical manifestations of allergic diseases which are mediated through both receptors.

More particularly, the present invention provides new and useful compounds of formula (1) or stereoisomers or pharmaceutically acceptable salts thereof which are both tachykinin antagonists and histamine antagonists.

In a further embodiment, as both tachykinin antagonists and histamine antagonists the present invention provides a method of treating allergic diseases, including: allergic rhinitis, including seasonal rhinitis and sinusitis; contact dermatitis; allergic conjictivitis; gastrointestinal allergies, such as those caused by food or drugs; cramping; nausea; vomiting; diarrhea; and ophthalmic allergies and uveitis; and inflammatory bowel diseases, including Crohn's diseases and ulcerative colitis; in a patient in need thereof comprising administering to said patient a therapeutically effective amount of a compound of formula (1).

Various diseases and conditions described to be treated herein, are well known and appreciated by those skilled in the art. It is also recognized that one skilled in the art may affect the associated diseases by treating a patient presently afflicted with the diseases or by prophylactically treating a patient afflicted with the diseases with a therapeutically effective amount of the compounds of formula (1).

As used herein, the term "patient" refers to a warm blooded animal such as a mammal which is afflicted with a particular allergic disease. It is understood that guinea pigs, dogs, cats, rats, mice, horses, cattle, sheep, and humans are examples of animals within the scope of the meaning of the term.

As used herein, the term "therapeutically effective amount" of a compound of formula (1) refers to an amount which is effective in controlling the diseases described herein. The term "controlling" is intended to refer to all processes wherein there may be a slowing, interrupting, arresting, or stopping of the progression of the diseases described herein, but does not necessarily indicate a total elimination of all disease symptoms, and is intended to include prophylactic treatment of the diseases.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are able to be determined by one skilled in the art.

In effecting treatment of a patient afflicted with diseases described above, a compound of formula (1) can be administered in any form or mode which makes the compound bioavailable in an effective amount, including oral, inhalation, and parenteral routes. For example, compounds of formula (1) can be administered orally, by inhalation of an aerosol or dry powder, subcutaneously, intramuscularly, intravenously, transdermally, intranasally, rectally, occularly, topically, and the like. Oral, inhalation, topical, or occular administration is generally preferred for treatment of allergic diseases. Oral, inhalation, or occular administration is more preferred for treatment of allergic diseases. One skilled in the art of preparing formulations can readily select the proper form and mode of administration depending upon the particular characteristics of the compound selected, the disease or condition to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility, and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of formula (1) present in such compositions is such that a suitable dosage will be obtained. Preferred compositions and preparations are able to be determined by one skilled in the art.

The compounds of the present invention may also be administered by inhalation, such as by aerosol or dry powder. Delivery may be by a liquefied or compressed gas or by a suitable pump system which dispenses the compounds of the present invention or a formulation thereof. Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; helating agents such as ethylene diaminetetraacetic acid; uffers such as acetates, citrates or phosphates and agents for the adjustment of tonicity such as sodium chloride or dextrose. The parenteral preparation can be enclosed in ampules, disposable syringes or multiple dose vials made of glass or plastic.

EXAMPLE A

Antagonism of [$^3$H]-pyrilamine binding to histamine $H_1$ receptors by putative antagonists One skilled in the art can measure the $H_1$ receptor affinity of proposed histamine antagonists as evaluated in rat brains or Chinese hamster ovary cells transfected with the human histamine $H_1$ receptor gene (CHOpcDNA3H1R cells). For the studies in rat brain, young male rats are sacrificed by decapitation and the brains are immediately removed. The cortici are dissected and used immediately or stored at −20° C. For the studies in Chinese hamster ovary cells, confluent cells are freshly scraped from culture flasks. The tissues or cells are homogenized with a Polytron (setting no. 6 for 15 seconds) in 20 mL of 50 mM potassium sodium phosphate (pH 7.4, at 4° C.). The homogenate is centrifuged at 48,000×g for 12 minutes at 4° C. The pellet is resuspended using a Polytron (setting no. 6 for 15 seconds) in incubation buffer (50 mM potassium sodium phosphate, pH 7.4, at ambient temperature, containing 0.1% bovine serum albumin) to a concentration of 40 mg/mL and is immediately added to tubes to start the assay. The protein content of the crude membrane suspension can be determined by the method of O. H. Lowery et al., *J. Biol. Chem.*, 193 265 (1951).

The binding assay is carried out in duplicate in 12×75 mm polypropylene tubes in 50 mM potassium sodium phosphate (pH 7.4, at ambient temperature) containing 0.1% bovine serum albumin. The radioligand, [$^3$H]-pyrilamine, is diluted in incubation buffer to a concentration of 2 nM and added to each tube (50 $\mu$L). The test compound is diluted in incubation buffer ($10^{-10}$ M to $10^{-5}$ M) and is added to the appropriate tubes (50 $\mu$L). The assay is started by the addition of 250 $\mu$L of well mixed tissue suspension. The final incubation volume is 0.5 mL. The assay is carried out at ambient temperature for 30 minutes. The incubation is terminated by the addition of 3.5 mL of 0.9% sodium chloride solution (4° C.) and filtration through GF/B filters that have been presoaked overnight in 0.1% polyethyleneimine, using a Brandel cell harvester. The filters are rapidly washed with two 3.5 mL portions of incubation buffer and transferred to scintillation vials. Ecolume (9 mL) is added the the vials. The vials are shaken and allowed to set for 4 hours before being counted by liquid scintillation spectrometry. Specific binding is determined as the difference between tubes containing no test compound and the tubes containing 10 μM promethazine. Total membrane bound radioactivity is generally about 5% of that added to the tubes. Specific binding is generally 75% to 90% of total binding as determined by the method of M. D. DeBacker et al., *Biochem. and Biophys. Res. Commun.*, 197(3) 1601 (1991). The molar concentration of compound that causes 50% inhibition of ligand binding at the screening dose (10 μM) is the $IC_{50}$ value, and is expressed as the cumulative mean (±S.E.M.) for n separate experiments.

EXAMPLE B

Antagonism of iodinated tachykinin binding to $NK_1$ receptors by putative antagonists One skilled in the art can measure the $NK_1$ receptor affinity of proposed tachykinin antagonists as evaluated in guinea pig lungs (Keystone Biologicals, Cleveland, Ohio). Tissues are homogenized with a Polytron in 15 volumes of 50 mM Tris-HCl buffer (pH 7.4, 4° C.) and centrifuged. The pellet is resuspended in Tris-HCl buffer and centrifuged; the pellet is washed twice by resuspension. The final pellet is resuspended at a concentration of 40 mg/ml in incubation buffer and remains at room temperature for at least 15 min prior to use. Receptor binding is initiated by addition of 250 μl membrane preparation in duplicate to 0.1 nM of $^{125}$I-Bolton Hunter Lys-3 labeled substance P in a final volume of 500 μl of buffer containing 50 mM Tris-HCl (pH 7.4 at room temperature), 0.1% bovine serum albumin, 2 mM manganese chloride, 40 μg/ml bacitracin, 4 μg/ml leupeptin and chymostatin, 1 μM thiorphan and various doses of the putative tachykinin antagonists. Incubations are performed at room temperature for 90 min; binding is terminated by addition of 50 mM Tris-HCl buffer (pH 7.4, 4° C.) and filtration under vacuum through GF/B filters presoaked with 0.1% polyethyleneimine. Filter bound radioactivity is quantitated in a gamma counter. Nonspecific binding is defined as binding in the presence of 1 μM substance P.

Specific binding is calculated by subtracting nonspecific binding from total binding. Competition of iodinated substance P binding by test compounds or standards is expressed as a percentage of this maximum competition. $IC_{50}$ values (concentration required to inhibit 50% of receptor binding) are generated for each of the test compounds by nonlinear regression using an iterative curve fitting program (GraphPAD Inplot, San Diego, Calif.).

EXAMPLE C

Histamine ($H_1$) antagonism in guinea pig ileum

One skilled in the art can determine that the compounds of the present invention are $H_1$ receptor antagonists invitro by evaluating the compound's ability to inhibit histamine mediated smooth muscle contraction. Male Hartley guinea pigs, weighing 200–450 grams, are sacrificed by $CO_2$ asphyxiation. A piece of ileum, about 20 cm in length, is removed and cut into 2 cm pieces. Each ileum piece is placed in an organ bath at 37° C. containing Tyrode's solution and is constantly aerated with 95% $O_2$/5% $CO_2$. Tyrode's solution has the composition: sodium chloride 136.9 mM, potassium chloride 2.68 nM, calcium chloride 1.8 mM, sodium dihydrogen phosphate 0.42 mM, sodium bicarbonate 11.9 mM, and dextrose 5.55 mM. Contractions are measured with an isometric transducer (Grass FTO3C), and are recorded on a polygraph recorder and/or a computer. The ileum strips are loaded with 1.0 grams of tension and allowed to equilibrate for a minimum of 30 minutes before starting the experiments. Tissues are preincubated with vehicle or varying concentrations of test compound followed by histamine challenge.

A competitive $H_1$ receptor antagonist produces a parallel shift of the histamine dose-response curve to the right without a depression of the maximal response. The potency of the antagonism is determined by the magnitude of the shift and is expressed as a $pA_2$ value which is the negative logarithm of the molar concentration of antagonist which produces a two-fold shift of the dose response curve to the right. The $pA_2$ value is calculated by using Schild analysis. O. Arunlakshana and H. O. Schild, *Br. J. Pharmacol Chemother.* 14, 48–58 (1958). When the slope of the lines obtained by a Schild analysis are not significantly different from one (1) the compound is acting as a competitive antagonist.

EXAMPLE D

Antagonism of tachykinin-induced phosphatidylinositol (PI) turnover in vitro by putative antagonists One skilled in the art can determine $NK_1$ receptor antagonism by measuring the substance P-induced phosphatidylinositol (PI, inositol phosphate) accumulation in UC11 cells in the presence and absence of $NK_1$ receptor antagonists. Cells are seeded onto 24-well plates at 125,000 cells/well, two or three days prior to the assay. Cells are loaded with 0.5 mL of 0.2 μM myo-[2-$^3$H(N)] inositol (American Radiolabeled Chemicals Inc., specific activity; 20 μCi/mmol) 20–24 hours prior to the assay. Cultured cells are maintained at 37° C. in 5% $CO_2$ environment.

On the day of the assay, media is aspirated and the cells incubated in RPMI-1640 media containing 40 μg/ml bacitracin, 4 μg/ml each of leupeptin and chymostatin, 0.1% bovine serum albumin, 10 μM thiorphan, and 10 mM lithium chloride. After 15 minutes, the test compound is added to the cells in a volume of 0.1 mL. After another 15 min, substance P is added to UC11 cells at various concentrations to start the reaction followed by incubation for 60 min at 37° C. in 5% $CO_2$ environment in a final volume of 1 mL. To terminate the reaction, the media is aspirated and methanol (0.1 mL) is added to each well. Two aliquots of methanol (0.5 mL) are added to the wells to harvest the cells into chloroform resistant tubes. Chloroform (1 mL) is added to each tube followed by doubly distilled water (0.5 mL). Samples are vortexed for 15 seconds and centrifuged at 1700×g for 10 minutes. An aliquot (0.9 mL) of the aqueous (top) phase is removed and added to doubly distilled water (2 mL). The mixture is vortexed and loaded onto a 50% Bio-Rad AG 1-X8 (formate form, 100–200 mesh) exchange column (Bio-Rad Laboratories, Hercules, Calif.). The columns are washed, in order, with: 1) 10 ml doubly distilled water, 2) 5 mL of 5 mM disodium tetraborate/60 mM sodium formate, and 3) 2 mL of 1 M ammonium formate/0.1 M formic acid. The third elution is collected and counted in 9 mL scintillation fluid. A 50 μl aliquot of the organic (bottom) phase is removed, dried in a scintillation vial and counted in 7 mL scintillation fluid. The ratio of DPM in the aqueous phase aliquot (total inositol phosphates) to the DPM in the 50 μl organic phase aliquot (total [$^3$H]inositol incorporated) is calculated for each sample. Data are expressed as a percent of agonist-induced accumulation of [³H]-inositol phosphates over basal levels. The ratios in the presence of test compound and/or standards are compared to the ratios for control samples (i.e. no stimulating agonist).

Dose-response graphs are constructed and the ability of the test compounds to inhibit tachykinin-induced phosphatidyinositol turnover determined with the aid of a computer program. Data is expressed as percent stimulation of total inositol phosphate accumulation over basal levels and normalized to the maximum response produced by substance P. Schild analysis is performed using dose response curves to obtain a value indicative of the strength of a competitive antagonist and is expressed as the $pA_2$, which is the negative logarithm of the molar concentration of antagonist which reduces the effect of a dose of agonist to one-half of that expected at the dose of agonist. The slope of the lines obtained by a Schild analysis are not significantly different from one (1) the compound is acting as a competitive antagonist.

EXAMPLE E

Evaluation of $H_1$ (or $NK_1$) antagonism in vivo

One skilled in the art can determine that the compounds of the present invention mediate the immediate hypersensitivity response in vivo by evaluating the ability of the compounds to inhibit the formation of histamine (or substance P) induced wheals in guinea pigs. Animals are anesthetized with pentobarbitol (i.p.). Dorsal skin is shaved and intradermal injections of histamine (or substance P) are given in the shaved area at appropriate times after the administration of the test compounds. Doses, routes, and times of administration may vary according to experimental design. The design of such experiments is well known and appreciated in the art. Immediately after the intradermal challenges, the animal is given an intravenous injection of 1% Evan's blue dye to make the wheals visible. At an appropriate time after the challenge the animals are sacrificed by $CO_2$ inhalation. The skin is removed and the diameter of each wheal is measured in two perpendicular directions. The wheal response is used an the index of the edema response. The percent of inhibition of the wheal response is calculated by comparing the drug-treated group to a vehicle-treated group. Linear regression of the dose-response inhibition curve is used to determine an $ED_{50}$ value, expressed in mg/kg, which is the dose of compound which inhibits histamine-induced skin wheal by 50%.

EXAMPLE F

Evaluation of $NK_1$ antagonism in vivo

One skilled in the art can also determine that the compounds of the present invention are $NK_1$ receptor antagonists in vivo by evaluating the compound's ability to inhibit substance induced plasma protein extravasation in guinea pig trachea. Substance P-induced protein leakage through postcapillary venules is assessed by measuring Evans Blue dye accumulation in guinea pig trachea.

When putative antagonists are administered intravenously, animals are anesthetized with pentobarbitol then injected with Evans Blue dye (20 mg/kg, i.v., prepared in 0.9% sodium chloride solution). One minute after dye administration, the antagonist is administered (i.v.) followed by substance P (0.3 nmole/kg, i.v.) and, after 5 min, excess dye removed from the circulation by transcardiac perfusion with 50 ml 0.9% sodium chloride solution. The trachea and primary bronchi are removed, blotted dry and weighed.

When the putative antagonist is administered orally, animals are anesthetized with pentobarbitol one hour after dosing and injected with Evans Blue dye (20 mg/kg, i.v., prepared in 0.9% sodium chloride solution). One minute after dye administration, administer substance P (0.3 nmole/kg, i.v.) and, after 5 min, excess dye removed from the circulation by transcardiac perfusion with 50 ml 0.9% sodium chloride solution. The trachea and primary bronchi are removed, blotted dry and weighed.

Dye quantitation is performed spectrophotometrically (620 nm) after extracting tissues in formamide for 24 hr at 50° C. Values are subtracted from background (dye only, no agonist). $ED_{50}$ (dose of compound which inhibits substance P-induced plasma protein extravasation by 50%) is calculated from linear regression analysis.

What is claimed is:

1. A compound of the formula

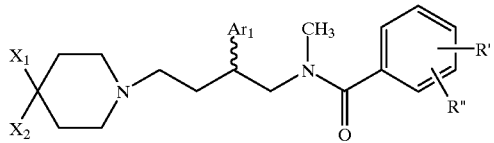

wherein

R' is from 1 to 3 substituents each independently chosen from the group consisting of hydrogen, halogen, $C_1$–$C_6$ alkyl, and $C_1$–$C_6$ alkoxy;

R" is hydrogen or a radical chosen from the group consisting of

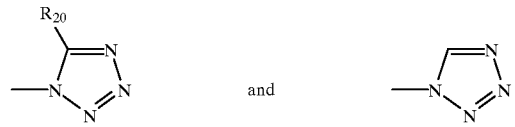

wherein $R_{20}$ is selected from the group consisting of hydrogen, $C_1$–$C_4$ alkyl, and —$CF_3$;

$Ar_1$ is a radical chosen from the group consisting of

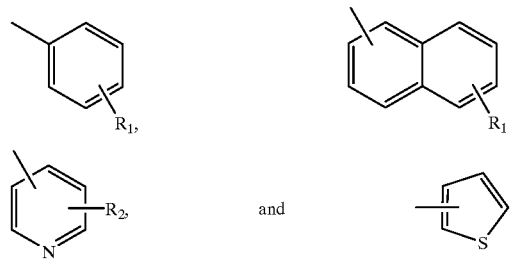

wherein $R_1$ is from 1 to 3 substituents each independently chosen from the group consisting of hydrogen, halogen, hydroxy, —$CF_3$, $C_1$–$C_6$ alkyl, and $C_1$–$C_6$ alkoxy;

$R_2$ is from 1 to 2 substituents each independently chosen from the group consisting of hydrogen, halogen, $C_1$–$C_6$ alkyl, and $C_1$–$C_6$ alkoxy;

$X_1$ and $X_2$ are as defined in one of parts A), B), or C):

A) $X_1$ is hydrogen;

$X_2$ is a radical chosen from the group consisting of

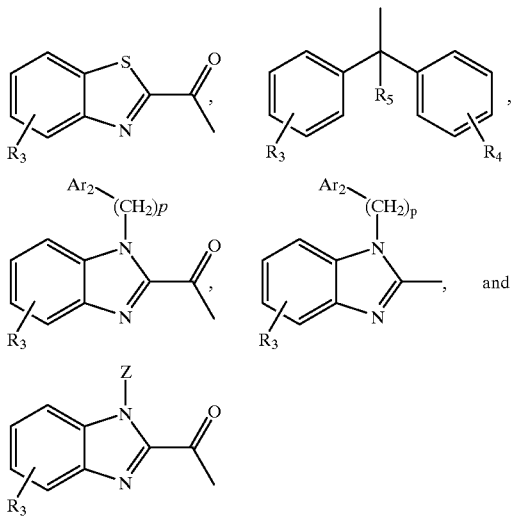

wherein
  p is 1 or 2;
  $R_3$ is from 1 to 3 substituents each independently chosen from the group consisting of hydrogen, halogen, —$CF_3$, $C_1$–$C_6$ alkyl, and $C_1$–$C_6$ alkoxy;
  $R_4$ is from 1 to 3 substituents each independently chosen from the group consisting of hydrogen, halogen, —$CF_3$, $C_1$–$C_6$ alkyl, and $C_1$–$C_6$ alkoxy;
  $R_5$ is hydrogen or hydroxy;
  $Ar_2$ is a radical chosen from the group consisting of

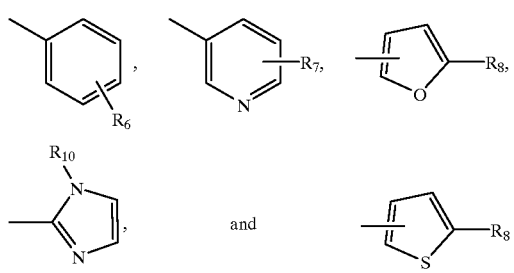

wherein
  $R_6$ is from 1 to 3 substituents each independently chosen from the group consisting of hydrogen, halogen, —$CF_3$, $C_1$–$C_6$ alkyl, $C_1$–$C_6$ alkoxy, and —$CO_2R_9$ wherein $R_9$ is chosen from the group consisting of hydrogen and $C_1$–$C_4$ alkyl;
  $R_7$ is from 1 to 2 substituents each independently chosen from the group consisting of hydrogen, halogen, $C_1$–$C_6$ alkyl, and $C_1$–$C_6$ alkoxy;
  $R_8$ is chosen from the group consisting of hydrogen, —$CH_3$, and —$CH_2OH$;
  $R_{10}$ is chosen from the group consisting of hydrogen, $C_1$–$C_4$ alkyl, and benzyl;
  Z is chosen from the group consisting of hydrogen, $C_1$–$C_6$ alkyl, —$(CH_2)_w$—O—$(CH_2)_t$—Y, —$(CH_2)_f$A, —$(CH_2)_u CO_2 R_{11}$, —$(CH_2)_u C(O)NR_{12}R_{13}$, —$(CH_2)_g C(O)(CH_2)_h CH_3$, —$(CH_2)_w$—O—$Ar_3$, —$CH_2CH_2OCF_3$, —$CH_2CF_3$, —$CH_2CH_2CH_2CF_3$, —$(CH_2)_2CH$=$CH_2$, —$CH_2CH$=$CH_2$, —$CH_2CH$=$CHCH_3$, —$CH_2CH$=$CHCH_2CH_3$, —$CH_2CH$=$C(CH_3)_2$, and —$CH_2OCH_2CH_2Si(CH_3)_3$ wherein
  w is an integer from 2 to 5;
  t is an integer from 1 to 3;
  f is 2 or 3;
  u is an integer from 1 to 4;
  g is an integer from 1 to 3;
  h is an integer from 0 to 3;
  w is an integer from 2 to 4;
  Y is chosen from the group consisting of hydrogen, —$CF_3$, —$CH$=$CH_2$, —$CH$=$C(CH_3)_2$, and —$CO_2R_{14}$ wherein $R_{14}$ is chosen from the group consisting of hydrogen and $C_2$–$C_4$ alkyl;
  A is chosen from the group consisting of —$NR_{15}R_{16}$, acetylamino, and morpholino wherein $R_{15}$ is chosen from the group consisting of hydrogen and $C_1$–$C_4$ alkyl and $R_{16}$ is $C_1$–$C_4$ alkyl;
  $R_{11}$ is chosen from the group consisting of hydrogen and $C_1$–$C_4$ alkyl;
  $R_{12}$ is chosen from the group consisting of hydrogen, $C_1$–$C_4$ alkyl, and benzyl;
  $R_{13}$ is chosen from the group consisting of hydrogen and $C_1$–$C_4$ alkyl;
  $Ar_3$ is a radical chosen from the group consisting of

wherein
  v is an integer from 1 to 3;
  $R_{17}$ is chosen from the group consisting of hydrogen and —$CO_2R_{18}$ wherein $R_{18}$ is chosen from the group consisting of hydrogen and $C_1$–$C_4$ alkyl;
B) $X_1$ is hydroxy;
  $X_2$ is a radical chosen from the group consisting of

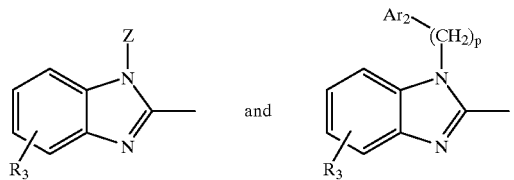

wherein p, $R_3$, Z, and $Ar_2$ are as previously defined;
C) $X_2$ is a radical of the formula;

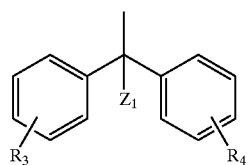

wherein $R_3$ and $R_4$ are as previously defined; and
  $X_1$ and $Z_1$ taken together form a second bond between the carbon atoms bearing $X_1$ and $Z_1$;
and stereoisomers and pharmaceutically acceptable salt thereof.

2. A compound of claim 1 wherein $X_1$ is hydrogen.

3. A compound of claim 2 wherein $X_2$ is a radical of the formula

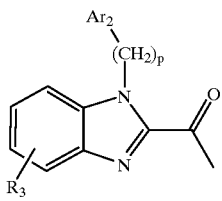

wherein $R_3$, $Ar_2$, and p are as defined in claim 1.

4. A compound of claim 3 wherein $R_3$ is hydrogen, p is 1, and $Ar_2$ is 4-fluorophenyl.

5. A compound of claim 3 wherein $R_3$ is hydrogen, p is 1, and $Ar_2$ is pyrid-2-yl.

6. A compound of claim 3 wherein $R_3$ is hydrogen, p is 1, and $Ar_2$ is fur-2-yl.

7. A compound of claim 3 wherein $R_3$ is hydrogen, p is 1, and $Ar_2$ is fur-3-yl.

8. A compound of claim 2 wherein $X_2$ is a radical of the formula

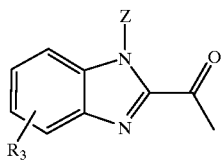

wherein $R_3$ and Z are as defined in claim 1.

9. A compound of claim 8 wherein Z is —$(CH_2)_w$—O—$(CH_2)_t$—Y wherein w, t, and Y are as defined in claim 1.

10. A compound of claim 9 wherein w is 2.

11. A compound of claim 10 wherein Z is 2-ethoxyethyl.

12. A compound of claim 1 wherein $X_1$ is hydroxy.

13. A compound of claim 12 wherein $X_2$ is a radical of the formula

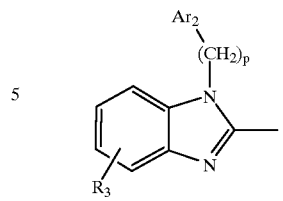

wherein $R_3$, $Ar_2$, and p are as defined in claim 1.

14. A compound of claim 13 wherein $R_3$ is hydrogen, p is 1, and $Ar_2$ is 4-fluorophenyl.

15. A compound of claim 1 wherein the compound is (+)-or (−)-N-methyl-N-(4-(4-(1-(pyrid-2-ylmethyl)-1H-benzimidazole-2-carbonyl)piperidin-1-yl)-2-(4-fluorophenyl)butyl)-3,4,5-trimethoxybenzamide or a mixture thereof.

16. A compound of claim 1 wherein the compound is (+)-or (−)-N-methyl-N-(4-(4-(1-(4-fluorobenzyl)-1H-benzimidazole-2-carbonyl)piperidin-1-yl)-2-(3,4-dichlorophenyl)butyl)benzamide or a mixture thereof.

17. A pharmaceutical composition comprising a compound of claim 1.

18. A pharmaceutical composition comprising a compound of claim 1 in admixture or otherwise in association with one or more inert carriers.

19. A method for inhibiting an allergic response in a patient in need thereof comprising administering to said patient an antihistamic or $NK_1$ antagonistic effective amount of a compound of claim 1.

20. A method of claim 19 wherein the allergic response is in asthma.

21. A method of claim 19 wherein the allergic response is in ophthalmia.

* * * * *